(12) United States Patent
Kim et al.

(10) Patent No.: US 11,078,195 B2
(45) Date of Patent: Aug. 3, 2021

(54) COMPOUND FOR INHIBITING NICOTINAMIDE PHOSPHORIBOSYLTRANSFERASE AND COMPOSITION CONTAINING SAME

(71) Applicant: CHECKMATE THERAPEUTICS INC., Seoul (KR)

(72) Inventors: Hyun Seok Kim, Gyeonggi-do (KR); Gyoon Hee Han, Seoul (KR)

(73) Assignee: Checkmate Therapeutics Inc.

( * ) Notice: Subject to any disclaimer, the term of this patent is extended or adjusted under 35 U.S.C. 154(b) by 239 days.

(21) Appl. No.: 16/085,774

(22) PCT Filed: Mar. 17, 2017

(86) PCT No.: PCT/KR2017/002895
§ 371 (c)(1),
(2) Date: Sep. 17, 2018

(87) PCT Pub. No.: WO2017/160116
PCT Pub. Date: Sep. 21, 2017

(65) Prior Publication Data
US 2020/0247795 A1 Aug. 6, 2020

Related U.S. Application Data

(60) Provisional application No. 62/309,557, filed on Mar. 17, 2016.

(51) Int. Cl.
| | | |
|---|---|---|
| *C07D 401/12* | (2006.01) |
| *C07D 413/12* | (2006.01) |
| *C07D 209/14* | (2006.01) |
| *C07D 213/82* | (2006.01) |
| *C07D 277/82* | (2006.01) |
| *C07D 405/12* | (2006.01) |
| *C07D 417/12* | (2006.01) |
| *C07D 417/14* | (2006.01) |
| *C07D 419/14* | (2006.01) |
| *C07D 471/04* | (2006.01) |
| *C07D 498/04* | (2006.01) |
| *C07D 513/04* | (2006.01) |

(52) U.S. Cl.
CPC ......... *C07D 413/12* (2013.01); *C07D 209/14* (2013.01); *C07D 213/82* (2013.01); *C07D 277/82* (2013.01); *C07D 401/12* (2013.01); *C07D 405/12* (2013.01); *C07D 417/12* (2013.01); *C07D 417/14* (2013.01); *C07D 419/14* (2013.01); *C07D 471/04* (2013.01); *C07D 498/04* (2013.01); *C07D 513/04* (2013.01)

(58) Field of Classification Search
None
See application file for complete search history.

(56) References Cited

U.S. PATENT DOCUMENTS 8,912,184 B1    12/2014   Fleischer et al.

FOREIGN PATENT DOCUMENTS

| WO | WO 99/62885 | 12/1999 | |
|---|---|---|---|
| WO | WO-2004106923 A1 * | 12/2004 | ........... G01N 33/582 |
| WO | WO 2009/019504 | 2/2009 | |
| WO | WO 2012/031197 | 3/2012 | |

OTHER PUBLICATIONS

International Search Report prepared by the Korean Intellectual Property Office dated Aug. 30, 2017, for International Application No. PCT/KR2017/002895.
Chemical Abstract Compound, STN express: RN 309720-32-9, Dec. 19, 2000, 1 page.
Chemical Abstract Compound, STN express: RN 865099-90-7, Oct. 12, 2005, 1 page.
Chemical Abstract Compound, STN express: RN 898099-59-7, Aug. 2, 2006, 1 page.
Ballell et al. "Fueling Open-Source Drug Discovery: 177 Small-Molecule Leads against Tuberculosis," ChemMedChem, 2013, vol. 8, No. 2, pp. 313-321.
Dragovich et al. "Fragment-based design of 3-aminopyridine-derived amides as potent inhibitors of human nicotinamide phosphoribosyltransferase (NAMPT)," Bioorganic & Medicinal Chemistry Letters, 2014, vol. 24, pp. 954-962.
Rada et al. "Antiviral Activity of Benzothiazole and Benzothiazolinethione Derivatives in Cell Cultures," Acta Virol., 1979, vol. 23, No. 3, pp. 203-209.
Yu et al. "NMR and theoretical study on interactions between diperoxovanadate complex and 4-substituted pyridines," Spectrochimica Acta Part A, 2008, vol. 71, No. 2, pp. 644-649.
CAS of compounds from STN International cited in CN 2017800180608 Office Action dated Aug. 3, 2020, 11 pages.
Bukhtiarova et al. "Structure and Antiinflammatory Activity of Isonicotinic and Nicotinic Amides," Pharmaceutical Chemistry Journal, 1997, vol. 31, No. 11, pp. 597-599.
Dunlop et al. "Quantitative Structure-Activity Relationships for Nicotinanilide Molluscicides," Pesticide Science, 1980, vol. 11, pp. 53-60.
Lo et al. "Substituted pyrazoles as novel she antagonist: Investigation of key binding interactions within the catalytic domain," Bioorganic & Medicinal Chemistry Letters, Nov. 2010, vol. 20, No. 20, pp. 6379-6383.
Sam et al. "Hypotensive Agents. Pyridinecarboxamides and Piperidinecarboxamides," Journal of the American Chemical Society, Feb. 1959, vol. 81, No. 3, pp. 710-713.
Shen et al. "Discovery of Inhibitors of Soluble Epoxide Hydrolase: A Target with Multiple Potential Therapeutic Indications," Journal of Medicinal Chemistry, Mar. 2012, vol. 55, No. 5, pp. 1789-1808.
Valenta et al. "Synthesis of Several 4-Hydroxy-3,5-Dimethoxybenzaides, Their O-Substituted Derivatives and Some Related Compounds as Potential Neurotropic Agents," Collection of Czechoslovak Chemical Communications, Feb. 1985, vol. 50, No. 2, pp. 510-518.

(Continued)

*Primary Examiner* — Zinna Northington Davis
(74) *Attorney, Agent, or Firm* — Sheridan Ross P.C.

(57) ABSTRACT

The present invention relates to a novel compounds for inhibiting nicotinamide phosphoribosyltransferase (NamPT), a composition comprising the same, and various uses thereof.

4 Claims, 19 Drawing Sheets

(56) References Cited

OTHER PUBLICATIONS

English Translation of Official Action for China Patent Application No. 2017800180608, dated Aug. 3, 2020, 9 pages.
Partial Supplementary Search Report for European Patent Application No. 17767017.1, dated Aug. 5, 2019, 18 pages.
Extended Search Report for European Patent Application No. 17767017.1, dated Nov. 14, 2019, 14 pages.
Database Registry (STN) RN 1010884-05-5, [online], Mar. 30, 2008, 1 page.
Database Registry (STN) RN 1242834-37-2, [online], Sep. 26, 2010, 1 page.
Database Registry (STN) RN 1144445-03-3, [online], May 8, 2009, 1 page.
Database Registry (STN) RN 896661-48-6, [online], Jul. 28, 2006, 1 page.
Database Registry (STN) RN 879567-42-7, [online], Apr. 7, 2006, 1 page.
Database Registry (STN) RN 839692-98-7, [online], Mar. 1, 2005, 1 page.
Database Registry (STN) RN 712293-08-8, [online], Jul. 19, 2004, 1 page.
Database Registry (STN) RN 865099-90-7, [online], Oct. 12, 2005, 1 page.
Database Registry (STN) RN 1216850-20-2, [online], Apr. 5, 2010, 1 page.
Database Registry (STN) RN 1146934-58-8, [online], May 15, 2009, 1 page.
Database Registry (STN) RN 865100-93-2, [online], Oct. 12, 2005, 1 page.
Database Registry (STN) RN 847848-43-5, [online], Apr. 4, 2005, 1 page.
Database Registry (STN) RN 824419-84-3, [online], Feb. 2, 2005, 1 page.
Database Registry (STN) RN 1331002-95-9, [online], Sep. 11, 2011, 1 page.
Database Registry (STN) RN 1340768-05-9, [online], Nov. 4, 2011, 1 page.
Database Registry (STN) RN 1252474-73-9, [online], Nov. 10, 2010, 1 page.
Databse Registry (STN) RN 302573-52-0, [online], Nov. 13, 2000, 1 page.
Database Registry (STN) RN 943108-17-6, [online], Jul. 22, 2007, 1 page.
Database Registry (STN) RN 930909-24-3, [online], Apr. 19, 2007, 1 page.
Database Registry (STN) RN 1252304-86-1, [online], Nov. 10, 2010, 1 page.
Ballell et al. "Supporting Information—Fueling Open-Source Drug Discovery: 177 Small-Molecule Leads against Tuberculosis," CHemMedChem, 2013, pp. 61 & 83.
Official Action with English Translation for Japan Patent Application No. 2018-548663, dated Feb. 24, 2021, 14 pages.

* cited by examiner

COMPOUND FOR INHIBITING NICOTINAMIDE PHOSPHORIBOSYLTRANSFERASE AND COMPOSITION CONTAINING SAME

CROSS REFERENCE TO RELATED APPLICATIONS

This application is a national stage application under 35 U.S.C. 371 and claims the benefit of PCT Application No. PCT/KR2017/002895 having an international filing date of 17 Mar. 2017, which designated the United States, which PCT application claimed the benefit of the U.S. Provisional Application No. 62/309,557 filed 17 Mar. 2016, the disclosure of each of which are incorporated herein by reference.

TECHNICAL FIELD

The present invention relates to novel compounds for inhibiting nicotinamide phosphoribosyltransferase (NamPT) and a composition comprising the same and various uses thereof.

BACKGROUND ART

NAD+(nicotinamide adenine dinucleotide) is a coenzyme that plays an important role in many physiologically essential processes (Ziegkel, M. Eur. J. Biochem. 267, 1550-1564, 2000). NAD is essential for several signaling pathways including mono-ADP-ribosylation in both the immune system and G-protein-coupled receptor signaling among other poly ADP-ribosylation in DNA repair, and is also essential for the activity of Sirtuin deacetylase (Garten, A. et al., *Trends in Endocrinology and Metabolism*, 20, 130-138, 2008).

Nicotinamide phosphoribosyltransferase (NamPT) is an enzyme catalyzing the phosphorylation of nicotinamide and is a rate-limiting enzyme in one of two pathways that restore NAD.

The evidence is increasing that NamPT inhibitors have efficacy as anticancer agents. Cancer cells have a higher basal turnover of NAD and also require higher energy with comparing to normal cells. Furthermore, increased NamPT expression was reported in colorectal cancer (Van Beijnum, J. R. et al., *Int. J. Cancer* 101, 118-127, 2002), and it has been reported that NamPT is involved in angiogenesis (Kim, S. R. et al., *Biochem. Biophys. Res. Commun.* 357, 150-156, 2007). Small molecule inhibitors of NamPT cause depletion of intracellular NAD+ levels and ultimately induce tumor cell death (Hansen, C M et al., *Anticancer Res.* 20, 42111-4220, 2000), as well as inhibit tumor growth in a xenograft model.

Also, NamPT inhibitors have potential as therapeutic agents in inflammatory and metabolic disorders (Galli, M. et al., *Cancer Res.* 70, 8-11, 2010). For example, NamPT is a predominant enzyme in T and B lymphocytes. In selective inhibition of NamPT, lymphocytes can inhibit the occurrence of autoimmune disease by decreasing NAD+, but cell types with other NAD+ synthesis pathways cannot. The small molecule NamPT inhibitor (FK866) inhibited the proliferation of activated T cells and induced apoptosis and was effective in arthritis animal models (collagen-induced arthritis) (Busso, N. et al., Plos One 3, e2267, 2008). NamPT activity increases NF-kB transcriptional activity in human vascular endothelial cells and induces MMP-2 and MMP-9 activity, suggesting a role for NamPT inhibitors in the prevention of inflammation-mediated complications of obesity and type 2 diabetes (Adya, R. et al., Diabetes Care, 31, 758-760, 2008).

As one of the NamPT inhibitors, (E)-N-[4-(1-benzoylpiperidin-4-yl)butyl]-3-(pyridin-3-yl)-acrylamide (also known as AP0866, FK866, WK175 or WK22.175, hereinafter referred to as 'FK866' [international non-trade name]) is known in particular as an anti-cancer agent. FK866 can be used for the treatment of diseases associated with deregulated apoptosis such as cancer. In the prior art, FK866 has been confirmed to hinder the biosynthesis of nicotinamide adenyl dinucleotides (also known as NAD and also referred to hereinafter) without any DNA damage effect and induce apoptotic cell death.

In addition, FK866 induces apoptosis in HepG2 cells without a major effect on cellular energy metabolism (Hasmann M, Schemainda I. FK866, a Highly Specific Noncompetitive Inhibitor of Nicotinamide Phosphoribosyltransferase, Represents a Novel Mechanism for Induction of Tumor Cell Apoptosis. Cancer Res 2003; 63:7436-7442. [PubMed: 14612543]). Instead of causing immediate cytotoxicity, inhibiting NamPT and depleting NAD in cells suggests that FK866 may be an effectively active agent for cancer cells depending on nicotinamide to synthesize NAD. The crystal structure of the NamPT-FK866 complex indicates that the compound binds to the nicotinamide-binding site of NamPT to inhibit its activity. FK866 was tested in a murine neoplastic cell carcinoma model and has been proved to exhibit antitumor, antimetastasis and antiangiogenic activity (Drevs J, et al., Antiangiogenic potency of FK866/K22.175, a new inhibitor of intracellular NAD biosynthesis, in murine renal cell carcinoma. Anticancer Res 2003; 23:4853-4858. [PubMed:14981935]).

A drug inhibiting NamPT may have a number of uses other than inflammatory diseases or cancer as described above. Deficiency of NamPT expression may strongly affect the development of both T and B lymphocytes. In addition, NamPT can affect endothelial cells in association with high glucose level, oxidative stress and aging, and further, NamPT is known to be able to use excess of glucose productively so that human endothelial cells on the process of the proliferation can be endured from aging and high oxidative stress of glucose and the replicative longevity and angiogenic activity are possible.

DISCLOSURE

Technical Problem

It is an object of the present invention to provide a novel compound capable of inhibiting nicotinamide phospholibosyltransferase (NamPT).

Another object of the present invention is to provide a composition capable of preventing, improving or treating NamPT-related diseases, comprising novel compounds capable of inhibiting NamPT.

It is still another object of the present invention to provide a method of preventing, improving or treating NamPT-related diseases by using a novel compound capable of inhibiting NamPT.

However, the technical problem to be solved by the present invention is not limited to the above-mentioned problems, and other problems not mentioned can be clearly understood by those skilled in the art from the following description.

Technical Solution

The inventors of the present invention have found a novel compound capable of inhibiting the activity of nicotinamide phosphoribosyltransferase (hereinafter, referred to as 'NamPT') and completed the present invention.

An embodiment of the present invention provides a compound selected from a compound represented by the following Chemical Formula 1, a pharmaceutically acceptable salt, an optical isomer, a hydrate and a solvate thereof:

[Chemical Formula 1]

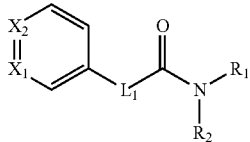

wherein $X_1$ and $X_2$ are each independently N or $C(R_3)$;

$L_1$ is a direct bond or $C_2$-$C_4$ alkenylene group;

$R_1$ and $R_2$ are each independently hydrogen, —$(CH_2)$m-$R_4$ or —N=$C(R_5)(R_6)$, the $R_1$ and $R_2$ are bonded to each other to form heterocycloalkyl ring having nuclear atoms of 5 to 7, heteroaryl ring having nuclear atoms of 5 to 14, or non-aromatic fused heteropolycyclic ring having nuclear atoms of 5 to 14;

$R_3$ is hydrogen or $C_1$-$C_6$ alkyl group;

$R_4$ is -$L_2$-$R_7$;

$L_2$ is a direct bond, $C_6$-$C_{10}$ arylene group or heteroarylene group having nuclear atoms of 5 to 14;

$R_5$ and $R_6$ can be bonded to each other to form non-aromatic fused heteropolycyclic ring having nuclear atoms of 5 to 14;

$R_7$ is selected from the group consisting of $C_1$-$C_6$ alkyl group, heterocycloalkyl group having nuclear atoms of 5 to 7, $C_6$-$C_{14}$ aryl, heteroaryl group having nuclear atoms of 5 to 14, $C_5$-$C_{14}$ non-aromatic fused polycyclic group, non-aromatic fused hetero polycyclic group having nuclear atoms of 5 to 14, —C(=O)—$R_8$, —S(=O)(=O)—$R_9$, —$(CH_2)$n-$N(R_{10})(R_{11})$ and —$(CH_2)$n-O-$(L_3)$-$(R_{12})$;

$R_8$ is selected from the group consisting of $C_1$-$C_6$ alkyl group, $C_1$-$C_6$ alkoxy group, $C_3$-$C_7$ cycloalkoxy group, heterocycloalkyl group having nuclear atoms of 5 to 7, heteroaryl group having nuclear atoms of 5 to 14 and non-aromatic fused hetero polycyclic group having nuclear atoms of 5 to 14;

$R_9$ is heterocycloalkyl having nuclear atoms of 5 to 7;

$R_{10}$ and $R_{11}$ are each independently, hydrogen, $C_1$-$C_6$ alkyl group or —C(=O)—$R_{13}$;

$L_3$ is a direct bond or $C_1$-$C_4$ alkylene group;

$R_{12}$ is $C_6$-$C_{14}$ aryl group or heteroaryl having nuclear atoms of 5 to 14;

$R_{13}$ is -$(L_4)$-$(R_{14})$, $L_4$ is a direct bond or heteroarylene group having nuclear atoms 5 to 14;

$R_{14}$ is $C_6$-$C_{14}$ aryl group or heteroaryl having nuclear atoms 5 to 14;

m and n are each independently integer of 0 to 4;

heterocycloalkyl ring, heteroaryl ring and non-aromatic fused heteropoly ring formed by bonding the $R_1$ and $R_2$ together are each independently unsubstituted or substituted with at least one substituent selected from the group consisting of -$(L_5)$-$(L_6)$-$(R_{15})$ and —NH—C(=O)—$R_{16}$, and when they are substituted with a plurality of substituents, they are the same as or different from each other;

$L_5$ is a direct bond or $C_1$-$C_4$ alkylene group;

$L_6$ is a direct bond or heteroarylene group having nuclear atoms of 5 to 14;

$R_{15}$ is $C_6$-$C_{14}$ aryl group or heteroaryl group having nuclear atoms of 5 to 14;

$R_{16}$ is $C_6$-$C_{14}$ aryl group or heteroaryl group having nuclear atoms of 5 to 14;

non-aromatic fused hetero polycyclic ring formed by bonding the $R_5$ and $R_6$ together, is substituted with at least one $C_1$-$C_6$ alkyl group or unsubstituted and when it is substituted with a plurality of substituents, they are the same as or different from each other;

the alkyl group, heterocycloalkyl group, aryl group, heteroaryl group, non-aromatic fused polycyclic ring group and non-aromatic fused hetero polycyclic ring group of $R_7$ are each independently unsubstituted or substituted with at least one substituent selected from the group consisting of halogen, nitro group, $C_1$-$C_6$ alkyl, $C_1$-$C_6$ alkoxy group, $C_6$-$C_{14}$ aryl group and heteroaryl group having nuclear atoms of 5 to 14 and when it is substituted with a plurality of substituents, they are the same as or different from each other;

the aryl group and heteroaryl group of $R_{14}$ are each independently unsubstituted or substituted with at least one substituent selected from the group consisting of halogen, $C_1$-$C_6$ alkyl and $C_1$-$C_6$ alkoxy group, and when it is substituted with a plurality of substituents, they are the same as or different from each other;

aryl group and heteroaryl group of the $R_{15}$ and $R_{16}$ are each independently unsubstituted or substituted with at least one substituent selected from the group consisting of $C_1$-$C_6$ alkyl and $C_1$-$C_6$ haloalkyl and when it is substituted with a plurality of substituents, they are the same as or different from each other.

Another embodiment of the present invention provides a pharmaceutical composition and a pharmaceutical formulation comprising therapeutically effective amount of the compound.

The term 'halogen' as used herein, unless otherwise indicated, means fluorine, chlorine, bromine or iodine.

As used herein, the term of '$C_1$-$C_6$ alkyl' means a linear or branched hydrocarbon residue having carbon atoms of 1 to 6, unless otherwise specified. Examples thereof include methyl, ethyl, propyl, isopropyl, n-butyl, sec-butyl, t-butyl, n-pentyl and n-hexyl, etc., but it is not limited thereto.

As used herein, the term of '$C_1$-$C_6$ alkoxy' means a linear or branched hydrocarbon residue having carbon atoms of 1 to 6, unless otherwise specified, Examples thereof include methoxy, ethoxy, propoxy, isobutoxy, n-butoxy, sec-butoxy, t-butoxy, pentoxy and hexoxy, etc. but it is not limited thereto.

As used herein, the term of '$C_3$-$C_7$ cycloalkoxy' means a cyclic hydrocarbon residue having carbon atoms of 3 to 6 linked to oxygen, unless otherwise specified. Examples thereof include cyclopropoxy, cyclobutoxy, cyclopentoxy, cyclohexoxy and cycloheptoxy, etc., but it is not limited.

As used herein, the term of '$C_3$-$C_7$ cycloalkyl' means a cyclic hydrocarbon residue having carbon atoms of 3 to 7, unless otherwise specified. Examples thereof include cyclopropyl, cyclobutyl, cyclopentyl, cyclohexyl and cycloheptyl, etc., but it is not limited thereto.

As used herein, the term of 'heterocycloalkyl having nuclear atoms of 5 to 7' means a 5 to 7 membered cyclic residue containing from one to three optionally selected from N, O, S, SO and $SO_2$, unless otherwise specified. Examples thereof include tetrahydrofuran-3-yl, tetrahydro-2H-pyran-4-yl, tetrahydro-2H-pyran-3-yl, oxepan-4-yl, oxepan-3-yl, piperadin-1-yl, piperadin-3-yl, piperadin-4-yl, piperazin-1-yl, morpholin-4-yl, thiomorpholin-4-yl, 1,1- dioxido-thiomorpholin-4-yl, pyrrolidin-1-yl, pyrrolidin-3-yl, azepan-1-yl, azepan-3-yl and azepan-4-yl, etc. but it is not limited thereto.

As used herein, the term of '$C_6$-$C_{14}$ aryl' means a mono- or poly-cyclic carbocyclic ring system having carbon atoms of 6 to 14 carbon atoms with at least one fused or non-fused aromatic ring, unless otherwise specified and examples of aryl include phenyl, naphthyl, tetrahydronaphthyl, indenyl and anthracenyl, etc., but it is not limited thereto.

As used herein, the term of heteroaryl having nuclear atoms of 5 to 14' means 5 to 14-membered aromatic group such as monocyclic or bicyclic or more cyclic aromatic group containing at least one, e.g. one to four heteroatoms selected from O, N and S, unless otherwise specified. Examples of monocyclic heteroaryl include thiazolyl, oxazolyl, thiophenyl, furanyl, pyrrolyl, imidazolyl, benzo[d]oxazolyl, isoxazolyl, oxazolopyridinyl, pyrazolyl, triazolyl, thiazolyl, benzo[d]thiazolyl, thiadiazolyl, tetrazolyl, oxadiazolyl, pyridinyl, pyridazinyl, pyrimidinyl, pyrazinyl, quinolinyl, naphthoxazolyl and groups similar thereto, but it is not limited thereto. Examples of bicyclic heteroaryl include indolyl, benzothiophenyl, benzofuranyl, benzimidazolyl, benzoxazolyl, benzisoxazolyl, benzthiadiazolyl, benztriazolyl, quinolinyl, isoquinolinyl, furinyl, furopyridinyl, carbazolyl, dibenzofuranyl, dibenzothiophenyl and groups similar thereof, but it is not limited thereto.

As used herein, the term of '$C_5$-$C_{14}$ non-aromatic fused polycyclic ring' means rings in which at least two rings are condensed with each other and contain only carbon atoms having 6 to 14 as ring forming atoms and have non-aromaticity in the entire molecule. Examples thereof include fluorenyl, etc., but it is not limited thereto.

As used herein, the term of 'non-aromatic fused hetero polycyclic rings having nuclear atoms of 5 to 14' means rings in which at least two rings are condensed with each other and contain at least one, e.g. one to four heteroatom selected from N, O and S, in addition to carbon as ring forming atoms and have non-aromaticity in the entire molecule of member of 5 to 14. Examples of the non-aromatic fused heteropolycyclic ring include indolinyl, isoindolinyl, tetrahydroquinolinyl, tetrahydroisoquinolinyl, 2,3-dihydro-1H-benzo [d]imidazolyl, 2,3-dihydrobenzazo[d]oxazolyl, 2,3-dihydrobenzo[d]thiazolyl, 3,3a-dihydropyrazolo[1,5-a]pyrimidinyl, 2,3,3a,7a-tetrahydrobenzo[d]thiazolyl and 2,3,3a,7a-tetrahydro-1H-isoindolyl, etc., but it is not limited thereto.

As used herein, the term of '$C_2$-$C_4$ alkenylene group' is a divalent residue derived from a hydrogen carbide chain containing at least one carbon-carbon double bond, and the alkenylene group is, for example, alkylene group having carbon atoms of 2 to 4. The alkylene group may be substituted with at least one polymerizable functional group or other substituents, and the hydrocarbon chain may contain a hetero atom such as nitrogen (N) or oxygen (O) in the chain. Examples thereof include ethylenyl, propylenyl and butylenyl, etc., but it is not limited.

As used herein, the term of "fused ring" means a condensed aliphatic ring, a condensed aromatic ring, a condensed heteroaliphatic ring, a condensed heteroaromatic ring, or a combination thereof.

Advantageous Effects

The compound represented by Chemical Formula 1 according to the present invention is excellent effect inhibiting nicotinamide phosphoribosyltransferase (NamPT), and can prevent, improve or treat various diseases associated with NamPT, and further, It can be used particularly useful as a remedy for preventing, improving or treating cancer.

BEST MODE

Figure 1:
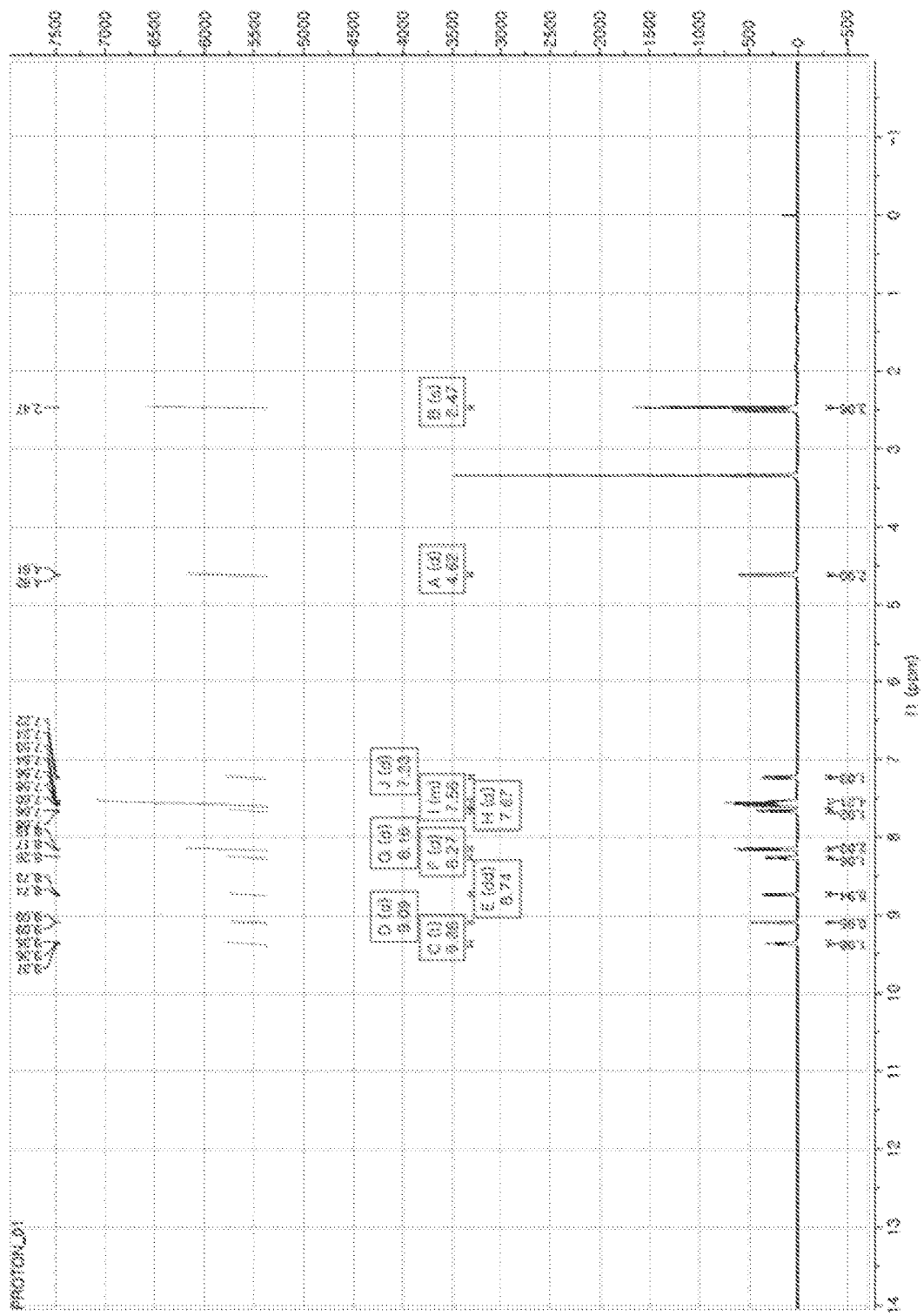
FIG. 1 shows NMR spectrum of N-(4-(6-methylbenzo[d]oxazol-2-yl) benzyl)nicotinamide (A4276) prepared in Synthesis Example 1 according to an example of the present invention.

Hereinafter, the present invention will be described in detail.

An aspect of the present invention provides a compound selected from a compound represented by following Chemical Formula 1, a pharmaceutically acceptable salt, an optical isomer, a hydrate and a solvate thereof:

[Chemical Formula 1]

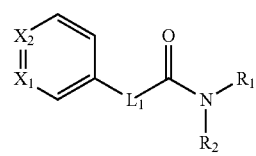

in the Chemical Formula 1,
wherein $X_1$ and $X_2$ are each independently N or $C(R_3)$;
$L_1$ is a direct bond or $C_2$-$C_4$ alkenylene group;
$R_1$ and $R_2$ are each independently hydrogen, —$(CH_2)$m-$R_4$ or —N=$C(R_5)(R_6)$, the $R_1$ and $R_2$ are bonded to each other to form heterocycloalkyl ring having nuclear atoms of 5 to 7, heteroaryl ring having nuclear atoms of 5 to 14, or non-aromatic fused heteropolycyclic ring having nuclear atoms of 5 to 14;
$R_3$ is hydrogen or $C_1$-$C_6$ alkyl;
$R_4$ is -$L_2$-$R_7$;
$L_2$ is a direct bond, $C_6$~$C_{10}$ arylene group or heteroarylene group having nuclear atoms of 5 to 14;
$R_5$ and $R_6$ can be bonded to each other to form non-aromatic fused heteropolycyclic ring having nuclear atoms of 5 to 14;
$R_7$ is selected from the group consisting of $C_1$-$C_6$ alkyl group, heterocycloalkyl group having nuclear atoms of 5 to 7, $C_6$-$C_{14}$ aryl, heteroaryl group having nuclear atoms of 5 to 14, $C_5$-$C_{14}$ non-aromatic fused polycyclic group, non-aromatic fused hetero polycyclic group having nuclear atoms of 5 to 14, —C(=O)—$R_8$, —S(=O)(=O)—$R_9$, —$(CH_2)$n-$N(R_{10})(R_{11})$ and —$(CH_2)$n-O-$(L_3)$-$(R_{12})$;
$R_8$ is selected from the group consisting of $C_1$-$C_6$ alkyl group, $C_1$-$C_6$ alkoxy group, $C_3$-$C_7$ cycloalkoxy group, heterocycloalkyl group having nuclear atoms of 5 to 7, heteroaryl group having nuclear atoms of 5 to 14 and non-aromatic fused hetero polycyclic group having nuclear atoms of 5 to 14;
$R_9$ is heterocycloalkyl having nuclear atoms of 5 to 7;
$R_{10}$ and $R_{11}$ are each independently, hydrogen, $C_1$~$C_6$ alkyl or —C(=O)—$R_{13}$,
$L_3$ is a direct bond or $C_1$~$C_4$ alkylene group;
$R_{12}$ is $C_6$~$C_{14}$ aryl group or heteroaryl having nuclear atoms of 5 to 14;
$R_{13}$ is -$(L_4)$-$(R_{14})$,
$L_4$ is a direct bond or heteroarylene group having nuclear atoms 5 to 14;
$R_{14}$ is $C_6$~$C_{14}$ aryl group or heteroaryl having nuclear atoms 5 to 14;
m and n are each independently integer of 0 to 4;
heterocycloalkyl ring, heteroaryl ring and non-aromatic fused heteropoly ring formed by bonding the $R_1$ and $R_2$ together are each independently unsubstituted or substituted with at least one substituent selected from the group consisting of -($L_5$)-($L_6$)-($R_{15}$) and —NH—C(=O)—$R_{16}$, and when they are substituted with a plurality of substituents, they are the same as or different from each other;

$L_5$ is a direct bond or $C_1$~$C_4$ alkylene group;

$L_6$ is a direct bond or heteroarylene group having nuclear atoms of 5 to 14;

$R_{15}$ is $C_6$~$C_{14}$ aryl group or heteroaryl group having nuclear atoms of 5 to 14;

$R_{16}$ is $C_6$~$C_{14}$ aryl group or heteroaryl group having nuclear atoms of 5 to 14;

non-aromatic fused hetero polycyclic ring formed by bonding the $R_5$ and $R_6$ together, is substituted with at least one $C_1$~$C_6$ alkyl or unsubstituted and when it is substituted with a plurality of substituents, they are the same as or different from each other;

the alkyl group, heterocycloalkyl group, aryl group, heteroaryl group, non-aromatic fused polycyclic ring group and non-aromatic fused hetero polycyclic ring group of $R_7$ are each independently unsubstituted or substituted with at least one substituent selected from the group consisting of halogen, nitro group, $C_1$~$C_6$ alkyl, $C_1$~$C_6$ alkoxy group, $C_6$~$C_{14}$ aryl group and heteroaryl group having nuclear atoms of 5 to 14 and when it is substituted with a plurality of substituents, they are the same as or different from each other;

the aryl group and heteroaryl group of $R_{14}$ are each independently unsubstituted or substituted with at least one substituent selected from the group consisting of halogen, $C_1$~$C_6$ alkyl and $C_1$~$C_6$ alkoxy group, and when it is substituted with a plurality of substituents, they are the same as or different from each other;

aryl group and heteroaryl group of the $R_{15}$ and $R_{16}$ are each independently unsubstituted or substituted with at least one substituent selected from the group consisting of $C_1$~$C_6$ alkyl and $C_1$~$C_6$ haloalkyl and when it is substituted with a plurality of substituents, they are the same as or different from each other.

Hereinafter, the present invention will be described in detail.

The present invention relates to a novel compound having a specific inhibitory activity against nicotinamide phosphoribosyltransferase (hereinafter referred to as 'NamPT'), a pharmaceutically acceptable salt thereof, an optical isomer, a hydrate and a solvate thereof, and a pharmaceutical composition for preventing or treating various diseases related to NamPT, comprising the same.

Specially, an aspect of the present invention provides a compound selected from a compound represented by following Chemical Formula 1, a pharmaceutically acceptable salt, an optical isomer, a hydrate and a solvate thereof:

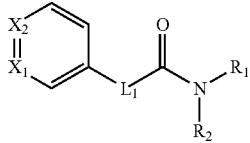

[Chemical Formula 1]

in the Chemical Formula 1, $X_1$ and $X_2$ are each independently N or C($R_3$);

$L_1$ is a direct bond or $C_2$-$C_4$ alkenylene group;

$R_1$ and $R_2$ are each independently hydrogen, —($CH_2$)m-$R_4$ or —N=C($R_5$)($R_6$), the $R_1$ and $R_2$ are bonded to each other to form heterocycloalkyl ring having nuclear atoms of 5 to 7, heteroaryl ring having nuclear atoms of 5 to 14, or non-aromatic fused heteropolycyclic ring having nuclear atoms of 5 to 14;

$R_3$ is hydrogen or $C_1$-$C_6$ alkyl;

$R_4$ is -$L_2$-$R_7$;

$L_2$ is a direct bond, $C_6$~$C_{10}$ arylene group or heteroarylene group having nuclear atoms of 5 to 14;

$R_5$ and $R_6$ can be bonded to each other to form non-aromatic fused heteropolycyclic ring having nuclear atoms of 5 to 14;

$R_7$ is selected from the group consisting of $C_1$-$C_6$ alkyl group, heterocycloalkyl group having nuclear atoms of 5 to 7, $C_6$-$C_{14}$ aryl, heteroaryl group having nuclear atoms of 5 to 14, $C_5$-$C_{14}$ non-aromatic fused polycyclic group, non-aromatic fused hetero polycyclic group having nuclear atoms of 5 to 14, —C(=O)—$R_8$, —S(=O)(=O)—$R_9$, —($CH_2$)n-N($R_{10}$)($R_{11}$) and —($CH_2$)n-O-($L_3$)-($R_{12}$);

$R_8$ is selected from the group consisting of $C_1$-$C_6$ alkyl group, $C_1$-$C_6$ alkoxy group, $C_3$-$C_7$ cycloalkoxy group, heterocycloalkyl group having nuclear atoms of 5 to 7, heteroaryl group having nuclear atoms of 5 to 14 and non-aromatic fused hetero polycyclic group having nuclear atoms of 5 to 14;

$R_9$ is heterocycloalkyl having nuclear atoms of 5 to 7;

$R_{10}$ and $R_{11}$ are each independently, hydrogen, $C_1$~$C_6$ alkyl or —C(=O)—$R_{13}$;

$L_3$ is a direct bond or $C_1$~$C_4$ alkylene group;

$R_{12}$ is $C_6$~$C_{14}$ aryl group or heteroaryl having nuclear atoms of 5 to 14;

$R_{13}$ is -($L_4$)-($R_{14}$);

$L_4$ is a direct bond or heteroarylene group having nuclear atoms 5 to 14;

$R_{14}$ is $C_6$~$C_{14}$ aryl group or heteroaryl having nuclear atoms 5 to 14;

m and n are each independently an integer of 0 to 4;

heterocycloalkyl ring, heteroaryl ring and non-aromatic fused heteropoly ring formed by bonding the $R_1$ and $R_2$ together are each independently unsubstituted or substituted with at least one substituent selected from the group consisting of -($L_5$)-($L_6$)-($R_{15}$) and —NH—C(=O)—$R_{16}$, and when they are substituted with a plurality of substituents, they are the same as or different from each other;

$L_5$ is a direct bond or $C_1$~$C_4$ alkylene group;

$L_6$ is a direct bond or heteroarylene group having nuclear atoms of 5 to 14;

$R_{15}$ is $C_6$~$C_{14}$ aryl group or heteroaryl group having nuclear atoms of 5 to 14;

$R_{16}$ is $C_6$~$C_{14}$ aryl group or heteroaryl group having nuclear atoms of 5 to 14;

non-aromatic fused hetero polycyclic ring formed by bonding the $R_5$ and $R_6$ together, is substituted with at least one $C_1$~$C_6$ alkyl or unsubstituted and when it is substituted with a plurality of substituents, they are the same as or different from each other;

the alkyl group, heterocycloalkyl group, aryl group, heteroaryl group, non-aromatic fused polycyclic ring group and non-aromatic fused hetero polycyclic ring group of $R_7$ are each independently unsubstituted or substituted with at least one substituent selected from the group consisting of halogen, nitro group, $C_1$~$C_6$ alkyl, $C_1$~$C_6$ alkoxy group, $C_6$~$C_{14}$ aryl group and heteroaryl group having nuclear atoms of 5 to 14 and when it is substituted with a plurality of substituents, they are the same as or different from each other;

the aryl group and heteroaryl group of $R_{14}$ are each independently unsubstituted or substituted with at least one substituent selected from the group consisting of halogen, $C_1$~$C_6$ alkyl and $C_1$~$C_6$ alkoxy group, and when it is substituted with a plurality of substituents, they are the same as or different from each other;

aryl group and heteroaryl group of the $R_{15}$ and $R_{16}$ are each independently unsubstituted or substituted with at least one substituent selected from the group consisting of $C_1$~$C_6$ alkyl and $C_1$~$C_6$ haloalkyl and when it is substituted with a plurality of substituents, they are the same as or different from each other.

An aspect of the present invention provides a compound selected from a compound represented by following Chemical Formula 2, a pharmaceutically acceptable salt, an optical isomer, a hydrate and a solvate thereof:

[Chemical Formula 2]

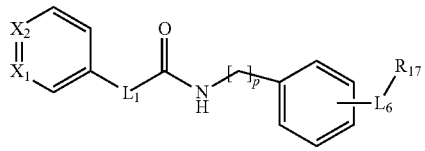

in the Chemical Formula 2,
p is an integer of 0 to 3;
$L_6$ is a direct bond, oxo group(*—C(=O)—*), or sulfonyl group(*—S(=O)(=O)—*);
$R_{17}$ is heterocycloalkyl group having nuclear atoms of 5 to 7, heteroaryl group having nuclear atoms of 5 to 14, —O—$(CH_2)_q$-$R_{18}$ or —$(CH_2)_r$-N($R_{19}$)($R_{20}$);
$R_{18}$ is hydrogen, $C_1$~$C_6$ alkyl group, $C_3$~$C_7$ cycloalkyl or heteroaryl group having nuclear atoms of 5 to 14;
$R_{19}$ and $R_{20}$ are each independently hydrogen or $C_1$~$C_6$ alkyl group;
q and r are each independently an integer of 0 to 2;
the heterocycloalkyl group and heteroaryl group of $R_{17}$ and the alkyl group cycloalkyl group and heteroaryl group of $R_{18}$ are each independently unsubstituted or substituted by at least one substituents selected from the group consisting of halogen, nitro group, $C_1$~$C_6$ alkyl, $C_1$~$C_6$ alkoxy group, $C_6$~$C_{14}$ aryl group and heteroaryl group having nuclear atoms of 5 to 14;
$X_1$, $X_2$ and $L_1$ are each as defined in claim 1.

According to one preferred embodiment of the present invention, in the Chemical Formula 2, the $X_1$ may be N and $X_2$ may be C($R_3$).

According to one preferred embodiment of the present invention, in the Chemical Formula 2, both $X_1$ and $X_2$ may be C($R_3$).

According to one preferred embodiment of the present invention, in the Chemical Formula 2, the $L_1$ may be a direct bond or $C_2$-$C_3$ alkenylene group and more preferably a direct bond.

According to one preferred embodiment of the present invention, in the Chemical Formula 2, the p may be an integer of 0 to 2 and more preferably an integer of 0 or 1.

According to one preferred embodiment of the present invention, in the Chemical Formula 2, the q may be an integer of 0 or 1.

According to one preferred embodiment of the present invention, in the Chemical Formula 2, heterocycloalkyl and heteroaryl group of the $R_{17}$ may be each independently unsubstituted or substituted with at least one substituent selected from the group consisting of halogen, nitro group, $C_1$~$C_6$ alkyl group, $C_1$~$C_6$ alkoxy group and $C_6$~$C_{14}$ aryl group.

According to one preferred embodiment of the present invention, in the Chemical Formula 2, the $R_{17}$ may be substituent represented by the following Chemical Formula 3:

[Chemical Formula 3]

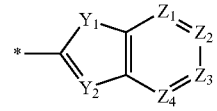

in the Chemical Formula 3,
* is a bonding site;
$Y_1$ is O or S;
$Y_2$ is N or C($R_{21}$);
$Z_1$ to $Z_4$ are each independently N or C($R_{22}$);
$R_{21}$ is hydrogen or $C_1$~$C_6$ alkyl group;
in case that $R_{22}$ is plural, they are the same or different from each other, and selected from the group consisting of hydrogen, halogen, nitro group, $C_1$~$C_6$ alkyl, $C_1$~$C_6$ alkoxy group, $C_6$~$C_{14}$ aryl group and heteroaryl group having nuclear atoms of 5 to 14 or in case that $R_{22}$ is plural, $R_{22}$ adjacent to each other can form fused ring by bonding with each other.

According to one preferred embodiment of the present invention, in the Chemical Formula 3, the $Y_1$ may be O and $Y_2$ may be N or C($R_{21}$) and more preferably the $Y_1$ may be O and the $Y_2$ may be N.

According to one preferred embodiment of the present invention, in the Chemical Formula 3, the $Y_1$ may be S and the $Y_2$ may be N.

According to one preferred embodiment of the present invention, in the Chemical Formula 3, the $Z_1$ to $Z_4$ may be all C($R_{22}$), and a plurality of $R_{22}$ may be the same as or different from each other.

According to one preferred embodiment of the present invention, in the Chemical Formula 3, at least one of the $Z_1$ to $Z_4$ is N and the others are C($R_{22}$), and a plurality of $R_{22}$ may be the same as or different from each other.

According to one preferred embodiment of the present invention, in the Chemical Formula 3, any one of the $Z_1$ to $Z_4$ is N and the others are C($R_{22}$), and a plurality of $R_{22}$ may be the same as or different from each other.

According to one preferred embodiment of the present invention, in the Chemical Formula 3, at least one of the $Z_1$ to $Z_4$ is C($R_{22}$) and a plurality of $R_{22}$ may be the same as or different from each other.

According to one preferred embodiment of the present invention, the Chemical Formula 3 may be represented by any one of the following Chemical Formulas a1 to a8, but it is not limited thereto:

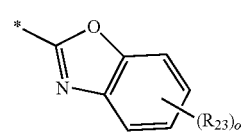

a1

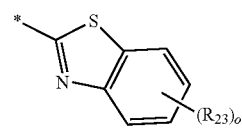

a2

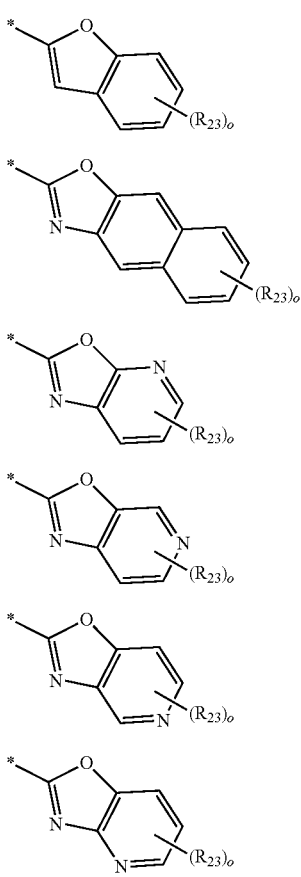

in Chemical Formula a1 to a8,

* is a bonding site;

o is an integer of 0 to 2;

$R_{23}$ can be selected from the group consisting of halogen, nitro group, $C_1$~$C_6$ alkyl, $C_1$~$C_6$ alkoxy group, $C_6$~$C_{14}$ aryl group and heteroaryl group having nuclear atoms of 5 to 14, in case that the $R_{23}$ is plural, they can be the same as or different from each other.

According to one preferred embodiment of the present invention, in the Chemical Formula a1 to a8, the o may be an integer of 0 or 1.

According to a preferred embodiment of the present invention, in Chemical Formula 2, $R_{17}$ may be a substituent represented by the following Chemical Formula 4:

[Chemical Formula 4]

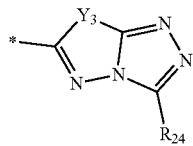

the Chemical Formula 4,

* is a bonding site;

$Y_3$ is O or S, $R_{24}$ may be hydrogen, $C_1$~$C_6$ alkyl group or $C_6$~$C_{14}$ aryl group.

According to one preferred embodiment of the present invention, in the Chemical Formula 4, the $Y_3$ may be S.

According to one preferred embodiment of the present invention, in the Chemical Formula 4, the $R_{24}$ may be hydrogen or $C_1$~$C_6$ alkyl group.

According to one preferred embodiment of the present invention, in the Chemical Formula 2, the $R_{17}$ may be —$(CH_2)r$-$N(R_{19})(R_{20})$, wherein the r may be an integer of 0 to 2, $R_{19}$ and $R_{20}$ may be each independently hydrogen or $C_1$~$C_6$ alkyl group.

According to one preferred embodiment of the present invention, in the Chemical Formula 2, the $R_{17}$ may be —$(CH_2)r$-$N(R_{19})(R_{20})$, wherein the r may be 0 or 1, $R_{19}$ and $R_{20}$ may be each independently $C_1$~$C_6$ alkyl group.

According to one preferred embodiment of the present invention, in the Chemical Formula 2, the $R_{17}$ may be heterocycloalkyl group having nuclear atoms of 5 to 7, and more preferably piperidinyl, piperazinyl, morpholinyl or thiomorpholinyl.

According to one preferred embodiment of the present invention, in the Chemical Formula 2, the $R_{17}$ may be heteroaryl group having nuclear atoms of 5 to 6, and heteroaryl group of the $R_{17}$ may be unsubstituted or substituted with at least one $C_1$~$C_6$ alkyl group, and when it is substituted with a plurality of substituents, they can be the same as or different from each other.

According to one preferred embodiment of the present invention, in the Chemical Formula 2, the $R_{17}$ may be pyrrolyl, imidazolyl or triazolyl, and the pyrrolyl, imidazolyl or triazolyl of the $R_{17}$ may be each independently unsubstituted substituted with at least one $C_1$-$C_6$ alkyl group, and when it is substituted with a plurality of substituents, they can be the same as or different from each other.

According to one preferred embodiment of the present invention, in the Chemical Formula 2, the $R_{17}$ may be —O—$(CH_2)q$-$R_{18}$.

According to one preferred embodiment of the present invention, in the Chemical Formula 2, the $R_{17}$ may be —O—$(CH_2)q$-$R_{18}$, q may be an integer of 0 to 2, and $R_{18}$ may be heteroaryl group having nuclear atoms of 5 to 14.

According to one preferred embodiment of the present invention, in the Chemical Formula 2, the $R_{17}$ may be —O—$(CH_2)q$-$R_{18}$, q may be an integer of 1 or 2, and $R_{18}$ may be pyridinyl, pyrimidinyl or triazinyl.

According to one preferred embodiment of the present invention, in the Chemical Formula 2, the $L_6$ may be oxo group, the $R_{17}$ may be —O—$(CH_2)q$-$R_{18}$ or heteroaryl group having nuclear atoms of 5 to 14, and more preferably the $L_6$ may be oxo group, the $R_{17}$ may be $C_1$~$C_6$ alkoxy group, $C_3$~$C_6$ cycloalkoxy group or heteroaryl group having nuclear atoms 5 to 10.

According to one preferred embodiment of the present invention, in the Chemical Formula 2, the $L_6$ may be sulfonyl group, the $R_{17}$ may be heterocycloalkyl having nuclear atoms 5 to 7, and more preferably the $L_6$ may be sulfonyl group and the $R_{17}$ may be piperidinyl, piperazinyl, morpholinyl or thiomorpholinyl.

According to a preferred embodiment of the present invention, the compound may be selected from a compound represented by the following Chemical Formula 5, a pharmaceutically acceptable salt, an optical isomer, a hydrate and a solvate thereof:

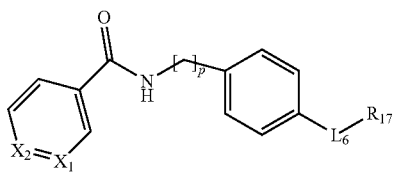

the Chemical Formula 5, $X_1$, $X_2$, $R_3$, p, $L_6$ and $R_{17}$ are each as defined in the Chemical Formula 2.

According to one preferred embodiment of the present invention, in the Chemical Formula 5, $X_1$ and $X_2$ are each independently N or $C(R_3)$, $R_3$ is hydrogen or $C_1$~$C_6$ alkyl group;

p, $L_6$ and $R_{17}$ are each as defined in the Chemical Formula 2.

According to an embodiment of the present invention, in the Chemical Formula 1, the $R_1$ and $R_2$ are bonded with each other to form heterocycloalkyl ring having nuclear atoms of 5 to 7 or non-aromatic fused heteropolycyclic ring having nuclear atoms of 5 to 14, and heterocycloalkyl ring and non-aromatic fused hetero polycyclic ring formed by bonding with the $R_1$ and $R_2$ are each independently unsubstituted or substituted by -($L_5$)-($L_6$)-($R_{15}$) or —NH—C(=O)—$R_{16}$, and the $L_5$, $L_6$, $R_{15}$ and $R_{16}$ are each as defined in the Chemical Formula 1.

According to one preferred embodiment of the present invention, the compound may be selected from a compound represented by following Chemical Formula 6, a pharmaceutically acceptable salt, an optical isomer, a hydrate and a solvate thereof:

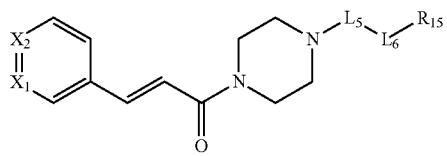

in the Chemical Formula 6, $X_1$, $X_2$, $L_5$, $L_6$ and $R_{15}$ are each as defined in the Chemical Formula 1.

According to a preferred embodiment of the present invention, in the Chemical Formula 6, one of the $X_1$ and $X_2$ may be N and the other may be $C(R_3)$, and more preferably $X_1$ may be N, and $X_2$ may be $C(R_3)$.

According to one preferred embodiment of the present invention, in the Chemical Formula 6, the $L_5$ may be $C_1$~$C_4$ alkylene group, more preferably $C_1$~$C_3$ alkylene group.

According to one preferred embodiment of the present invention, in the Chemical Formula 6, the $L_6$ may be heteroarylene group having nuclear atoms of 5 to 14, more preferably heteroarylene group having nuclear atoms 5 to 10.

According to one preferred embodiment of the present invention, in the Chemical Formula, the $L_6$ may be thiazolyl, oxazolyl or thiophenyl, and more preferably thiazolyl, but it is not limited thereto.

According to one preferred embodiment of the present invention, in the Chemical Formula 6, the $R_{15}$ may be heteroaryl group having nuclear atoms of 5 to 14, and more preferably heteroaryl group having nuclear atoms of 5 to 10.

According to one preferred embodiment of the present invention, in the Chemical Formula 6, the $R_{15}$ may be thiophenyl, furanyl or pyrrolyl, and more preferably furanyl, but it is not limited thereto.

According to one preferred embodiment of the present invention, the compound may be selected from a compound represented by following Chemical Formula 7, a pharmaceutically acceptable salt, an optical isomer, a hydrate and a solvate thereof:

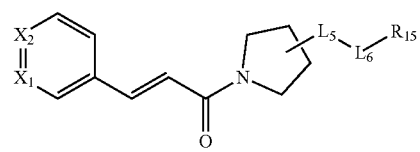

the Chemical Formula 7, $X_1$, $X_2$, $L_5$, $L_6$ and $R_{15}$ are each as defined in the Chemical Formula 1.

According to one preferred embodiment of the present invention, in Chemical Formula 7, one of the $X_1$ and $X_2$ may be N and the other may be $C(R_3)$, more preferably X1 may be N and $X_2$ may be $C(R_3)$.

According to one preferred embodiment of the present invention, in the Chemical Formula 7, at least one of the $L_5$ and $L_6$ may be a direct bond, and preferably $L_5$ and $L_6$ may all be a direct bond.

According to one preferred embodiment of the present invention, in the Chemical Formula 7, the $R_{15}$ may be heteroaryl group having nuclear atoms of 5 to 14, heteroaryl group of the $R_{15}$ may be unsubstituted or substituted by at least one substituents selected from the group consisting of $C_1$~$C_6$ alkyl group and $C_1$~$C_6$ haloalkyl, and when it is substituted with a plurality of substituents, they can be the same as or different from each other.

According to one preferred embodiment of the present invention, in the Chemical Formula 7, the $R_{15}$ may be indolizinyl, pyrazolopyrimidinyl, pyrrolopyrimidinyl or pyrazolopyridinyl, and more preferably may be pyrazolopyrimidinyl, but it is not limited thereto.

According to one preferred embodiment of the present invention, the compound may be selected from a compound represented by the following Chemical Formula 8, a pharmaceutically acceptable salt, an optical isomer, a hydrate and a solvate thereof:

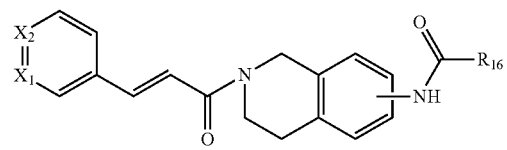

the Chemical Formula 8, $X_1$, $X_2$ and $R_{16}$ are each as defined in the Chemical Formula 1.

According to one preferred embodiment of the present invention, in the Chemical Formula 8, one of the $X_1$ and $X_2$ may be N and the other may be C($R_3$), more preferably $X_1$ may be N and $X_2$ may be C($R_3$).

According to one preferred embodiment of the present invention, in the Chemical Formula 8, the $R_{16}$ may be $C_6$~$C_{14}$ aryl group or heteroaryl group having nuclear atoms of 5 to 14, more preferably phenyl group, a pyridinyl group, a pyrimidinyl group or a triazinyl group, but it is limited thereto.

According to one preferred embodiment of the present invention, the Chemical Formula 8, the $R_{16}$ may be heteroaryl group having nuclear atoms of 5 to 14, more preferably pyridinyl group, a pyrimidinyl group or a triazinyl group, but it is not limited thereto.

According to an embodiment of the present invention, in Chemical Formula 1, the $R_1$ may be hydrogen, the $R_2$ may be —(CH$_2$)m-$R_4$.

According to one preferred embodiment of the present invention, in the Chemical Formula 1, the $R_1$ may be hydrogen, and the $R_2$ may be —(CH$_2$)m-$R_4$;

the m is an integer of 0 to 4, more preferably an integer of 0 to 3;

the $R_4$ is -$L_2$-$R_7$;

$L_2$ is a direct bond;

$R_7$ may be $C_5$~$C_{14}$ non-aromatic fused polycyclic group or non-aromatic fused hetero polycyclic group having nuclear atoms of 5 to 14.

According to one preferred embodiment of the present invention, in the Chemical Formula 1, the $R_2$ may be indolinyl, isoindolinyl, tetrahydroquinolinyl or tetrahydroisoquinolinyl, and more preferably indolinyl, but it is not limited thereto.

According to one preferred embodiment of the present invention, the compound may be selected from a compound represented by following Chemical Formula 9, a pharmaceutically acceptable salt, an optical isomer, a hydrate and a solvate thereof:

[Chemical Formula 9]

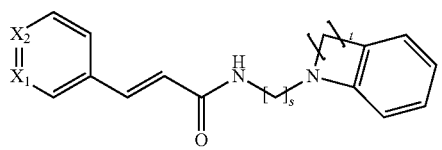

the Chemical Formula 9, s and t are each independently an integer of 0 to 4;

$X_1$ and $X_2$ are each as defined in the Chemical Formula 1.

According to one preferred embodiment of the present invention, in the Chemical Formula 9, one of the $X_1$ and $X_2$ may be N, and the other may be C($R_3$), and more preferably $X_1$ may be N and $X_2$ may be C($R_3$).

According to an embodiment of the present invention, in the Chemical Formula 1, the $R_1$ may be hydrogen and the $R_2$ may be —N=C($R_5$)($R_6$).

According to one preferred embodiment of the present invention, in the Chemical Formula 1, $R_1$ may be hydrogen and $R_2$ may be —N=C($R_5$)($R_6$);

the $R_5$ and $R_6$ are bonded with each other to form non-aromatic fused hetero polycyclic ring having nuclear atoms of 5 to 10; and non-aromatic fused hetero polycyclic ring formed by bonding with $R_5$ and $R_6$ to each other is unsubstituted or substituted by at least one $C_1$~$C_6$ alkyl group, and when it is with a plurality of substituents which are the same as or different to each other.

According to one preferred embodiment of the present invention, the compound may be selected from a compound represented by following Chemical Formula 10, a pharmaceutically acceptable salt, an optical isomer, a hydrate and a solvate thereof:

[Chemical Formula 10]

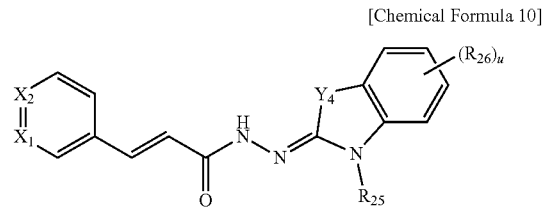

in the Chemical Formula 10, $Y_4$ is N($R_{27}$), O or S;

$R_{25}$ and $R_{27}$ are each independently hydrogen, $C_1$~$C_6$ alkyl group or $C_6$~$C_{14}$ aryl group;

u is an integer of 0 to 2;

$R_{26}$ is $C_1$~$C_6$ alkyl group or $C_6$~$C_{14}$ aryl group, when the $R_{26}$ is plural, they can be the same as or different from to each other;

$X_1$ and $X_2$ are each as defined in claim 1.

According to one preferred embodiment of the present invention, in the Chemical Formula 10, the $Y_4$ may be O or S and more preferably S.

According to one preferred embodiment of the present invention, in the Chemical Formula 10, the $R_{25}$ may be hydrogen or $C_1$~$C_6$ alkyl group.

According to an embodiment of the present invention, the compound may be selected from a compound represented by following Chemical Formula 11, a pharmaceutically acceptable salt, an optical isomer, a hydrate and a solvate thereof:

[Chemical Formula 11]

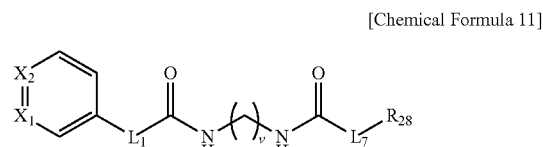

the Chemical Formula 11, v is an integer of 0 to 4;

$L_7$ is a direct bond or heteroarylene group having nuclear atoms of 5 to 14;

$R_{28}$ is $C_6$~$C_{14}$ aryl group or heteroaryl group having nuclear atoms of 5 to 14;

aryl group and heteroaryl group of the $R_{28}$ are each independently unsubstituted or substituted by at least one substituents selected from the group consisting of halogen, $C_1$~$C_6$ alkyl and $C_1$~$C_6$ alkoxy group, when they are substituted by a plurality of substituents which are the same as or different to each other;

$X_1$, $X_2$ and $L_1$ are each as defined in claim 1.

According to one preferred embodiment of the present invention, in the Chemical Formula 11, one of the $X_1$ and $X_2$ may be N and the other may be C($R_3$), and more preferably $X_1$ may be N and $X_2$ may be C($R_3$).

According to one preferred embodiment of the present invention, in the Chemical Formula 11, the $L_1$ may be a direct bond.

According to one preferred embodiment of the present invention, in the Chemical Formula 11, the v may be an integer of 0 to 3, more preferably an integer of 1 or 2.

According to one preferred embodiment of the present invention, in the Chemical Formula 11, the $L_7$ may be a direct bond or selected from the group consisting of furanyl group, isoxazolyl group, oxazolyl group and an oxadiazolyl group, and more preferably oxadiazolyl group.

According to the preferred embodiment of the present invention, the compound may be selected from a compound represented by following Chemical Formula 12, a pharmaceutically acceptable salt, an optical isomer, a hydrate and a solvate thereof:

[Chemical Formula 12]

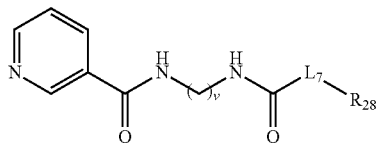

in the Chemical Formula 12, v, $L_7$ and $R_{28}$ are each as defined in the Chemical Formula 11.

According to one preferred embodiment of the present invention, in the Chemical Formula 12, the v may be an integer of 0 to 3, more preferably an integer of 1 or 2.

According to one preferred embodiment of the present invention, in the Chemical Formula 12, the $R_{28}$ may be selected from the group consisting of phenyl group, pyridinyl group, pyrimidinyl group, triazinyl group, naphthalenyl group, pyrrolyl group, furanyl group, thiophenyl group, quinolinyl group, isoquinolinyl group, cinnolinyl group, quinazolinyl group, phthalazinyl group, indenyl group, benzimidazolyl group, benzoxazolyl group, benzothiazolyl group, indolyl group, benzofuranyl group and benzothiophenyl group, phenyl group, pyridinyl group, pyrimidinyl group, triazinyl group, naphthalenyl group, pyrrolyl group, furanyl group, thiophenyl group, quinolinyl group, isoquinolinyl group, cinnolinyl group, quinazolinyl group, phthalazinyl group, indenyl group, benzimidazolyl group, benzoxazolyl group, benzothiazolyl group, indolyl group, benzofuranyl group and benzothiophenyl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is a direct bond, the $R_{28}$ is heteroaryl group having nuclear atoms of 5 to 14, heteroaryl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is a direct bond, the $R_{28}$ may be selected from the group consisting of naphthalenyl group, quinolinyl group, isoquinolinyl group, cinnolinyl group, quinazolinyl group, phthalazinyl group, indenyl group, benzimidazolyl group, benzoxazolyl group, benzothiazolyl group, indolyl group, benzofuranyl group and benzothiophenyl group, and the naphthalenyl group, quinolinyl group, isoquinolinyl group, cinnolinyl group, quinazolinyl group, phthalazinyl group, indenyl group, benzimidazolyl group, benzoxazolyl group, benzothiazolyl group, indolyl group, benzofuranyl group and benzothiophenyl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is a direct bond, the $R_{28}$ may be selected from the group consisting of quinolinyl group, isoquinolinyl group, cinnolinyl group, quinazolinyl group, phthalazinyl group, benzimidazolyl group, benzoxazolyl group and benzothiazolyl group, and the quinolinyl group, isoquinolinyl group, cinnolinyl group, quinazolinyl group, phthalazinyl group, benzimidazolyl group, benzoxazolyl group and benzothiazolyl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is heteroarylene group having nuclear atoms of 5 to 14, the $R_{28}$ is $C_6$~$C_{14}$ aryl group or heteroaryl group having nuclear atoms of 5 to 14, the aryl group and heteroaryl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is selected from the group consisting of furanyl group, isoxazolyl group, oxazolyl group and oxadiazolyl group, the $R_{28}$ is $C_6$~$C_{14}$ aryl group or heteroaryl group having nuclear atoms of 5 to 14, the aryl group and heteroaryl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, in the Chemical Formula 12, the $L_7$ is selected from the group consisting of furanyl group, isoxazolyl group, oxazolyl group and oxadiazolyl group, the $R_{28}$ is selected from the group consisting of phenyl group, naphthalenyl group, pyrrolyl group, furanyl group, thiophenyl group, quinolinyl group and isoquinolinyl group, and the phenyl group, naphthalenyl group, pyrrolyl group, furanyl group, thiophenyl group, quinolinyl group and isoquinolinyl group of the $R_{28}$ may be each independently unsubstituted or substituted by at least one substituents selected from the group consisting of halogen, $C_1$~$C_6$ alkyl group and $C_1$~$C_6$ alkoxy group, and when it is substituted with a plurality of substituents, they can be the same as or different from each other.

According to one preferred embodiment of the present invention, the compound may be selected from a compound represented by following Chemical Formula 13, a pharmaceutically acceptable salt, an optical isomer, a hydrate and a solvate thereof:

[Chemical Formula 13]

in the Chemical Formula 13, v and $R_{28}$ may be each as defined in the Chemical Formula 11.

According to one preferred embodiment of the present invention, in the Chemical Formula 13, the v may be an integer of 0 to 3, more preferably an integer of 1 or 2.

According to one preferred embodiment of the present invention, in the Chemical Formula 13, the $R_{28}$ is $C_6$-$C_{10}$ aryl group or heteroaryl group having nuclear atoms of 5 to 10, the $R_{28}$ aryl group and heteroaryl group may be each independently unsubstituted or substituted by at least one substituents selected from the group consisting of halogen, $C_1$-$C_6$ alkyl group and $C_1$-$C_6$ alkoxy group, and when it is substituted with a plurality of substituents, they can be the same as or different from each other.

According to one preferred embodiment of the present invention, in the Chemical Formula 13, the $R_{28}$ may be selected from the group consisting of phenyl group, naphthalenyl group, pyrrolyl group, furanyl group, thiophenyl group, quinolinyl group and isoquinolinyl group, the phenyl group, naphthalenyl group, pyrrolyl group, furanyl group, thiophenyl group, quinolinyl group and isoquinolinyl group of the $R_{28}$ may be each independently unsubstituted or substituted by at least one substituents selected from the group consisting of halogen, $C_1$-$C_6$ alkyl group and $C_1$-$C_6$ alkoxy group, and when it is substituted with a plurality of substituents, they can be the same as or different from each other.

According to an embodiment of the present invention, the compound may be selected from a compound represented by following Chemical Formula 14, a pharmaceutically acceptable salt, an optical isomer, a hydrate and a solvate thereof:

[Chemical Formula 14]

in the Chemical Formula 14, $R_{29}$ is $C_1$-$C_6$ alkyl group;

$X_1$ and $X_2$ are each as defined in the Chemical Formula 1.

According to one preferred embodiment of the present invention, in the Chemical Formula 14, one of the $X_1$ and $X_2$ may be N, and the other may be $C(R_3)$, and more preferably $X_2$ may be N and $X_1$ may be $C(R_3)$.

According to one preferred embodiment of the present invention, in the Chemical Formula 14, the $X_1$ and $X_2$ are all $C(R_3)$, and at this time, the $R_3$ may be hydrogen or $C_1$-$C_6$ alkyl group.

According to an embodiment of the present invention, the compound may be selected from a compound represented by following Chemical Formula 15, a pharmaceutically acceptable salt, an optical isomer, a hydrate and a solvate thereof:

[Chemical Formula 15]

in the Chemical Formula 15, $L_8$ is heteroarylene group having nuclear atoms of 5 to 14;

$R_{30}$ is $C_6$-$C_{14}$ aryl group or heteroaryl group having nuclear atoms of 5 to 14;

the aryl group and heteroaryl group of the $R_{30}$ are each independently unsubstituted or substituted by at least one substituents selected from the group consisting of $C_1$-$C_6$ alkyl group, when it is substituted with a plurality of substituents and they are the same as or different from each other;

$X_1$, $X_2$ and $L_1$ are each as defined in claim 1.

According to one preferred embodiment of the present invention, in the Chemical Formula 15, one of $X_1$ and $X_2$ may be N, the other may be $C(R_3)$, and more preferably $X_1$ may be N and $X_2$ may be $C(R_3)$.

According to one preferred embodiment of the present invention, in the Chemical Formula 15, $L_1$ may be a direct bond.

According to one preferred embodiment of the present invention, the Chemical Formula 15 may be a linker represented by the following Chemical Formula 16:

[Chemical Formula 16]

in the Chemical Formula 16,

* is a bonding site;

$Y_5$ is O or S;

$Z_5$ is N or $C(R_{31})$;

$R_{31}$ is hydrogen or $C_1$-$C_6$ alkyl group.

According to one preferred embodiment of the present invention, in the Chemical Formula 15, the $R_{30}$ may be selected from the group consisting of phenyl group, pyridinyl group, pyrimidinyl group, triazinyl group, naphthalenyl group, quinolinyl group, isoquinolinyl group, cinnolinyl group, quinazolinyl group and phthalazinyl group, the phenyl group, pyridinyl group, pyrimidinyl group, triazinyl group, naphthalenyl group, quinolinyl group, isoquinolinyl group, cinnolinyl group, quinazolinyl group and phthalazinyl group of the $R_{30}$ may be each independently unsubstituted or substituted by at least one substituents selected from the group consisting of $C_1$-$C_6$ alkyl group, and when it is substituted with a plurality of substituents, they can be the same as or different from each other.

According to one preferred embodiment of the present invention, the compound may be selected from a compound represented by following Chemical Formula 17, a pharmaceutically acceptable salt, an optical isomer, a hydrate and a solvate thereof:

[Chemical Formula 17]

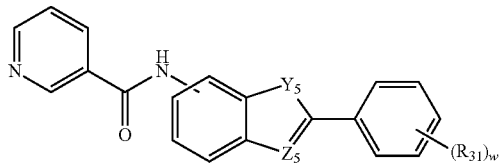

in the Chemical Formula 17,
$Y_5$ is O or S;
$Z_5$ is N or $C(R_{32})$;
w is an integer of 0 to 3;
$R_{31}$ is $C_1$~$C_6$ alkyl group, when the $R_{31}$ is a plural, they are same as or different to each other;
$R_{32}$ is hydrogen or $C_1$~$C_6$ alkyl group.

An embodiment of the present invention may be methyl 4-(2-(imidazo[1,2-a]pyridine-6-carboxamido)ethyl)benzoate represented by the following Chemical Formula 18:

[Chemical Formula 18]

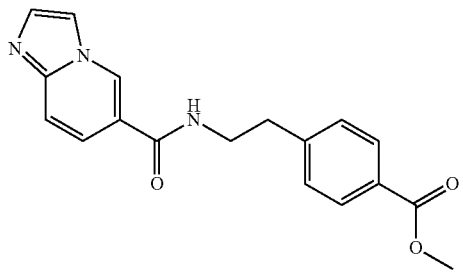

Preferred examples of the compound according to the present invention include, but are not limited to:
1) N-(4-(benzo[d]oxazol-2-yl)benzyl)nicotinamide;
2) N-(4-(6-methylbenzo[d]oxazol-2-yl)benzyl)nicotinamide;
3) N-(4-(6-methylbenzo[d]oxazol-2-yl)benzyl)benzamide;
4) N-(4-(5-methylbenzo[d]oxazol-2-yl)benzyl)nicotinamide;
5) N-(4-(5-ethylbenzo[d]oxazol-2-yl)benzyl)nicotinamide;
6) N-(4-(6-ethylbenzo[d]oxazol-2-yl)benzyl)nicotinamide;
7) N-(4-(5-isopropylbenzo[d]oxazol-2-yl)benzyl)nicotinamide;
8) N-(4-(6-(tert-butyl)benzo[d]oxazol-2-yl)benzyl)nicotinamide;
9) N-(4-(5-methoxybenzo[d]oxazol-2-yl)benzyl)nicotinamide;
10) N-(4-(6-chlorobenzo[d]oxazol-2-yl)benzyl)nicotinamide;
11) N-(4-(6-nitrobenzo[d]oxazol-2-yl)benzyl)nicotinamide;
12) N-(4-(5-phenylbenzo[d]oxazol-2-yl)benzyl)nicotinamide;
13) N-(4-(naphtho[2,3-d]oxazol-2-yl)benzyl)nicotinamide;
14) N-(4-(oxazolo[5,4-b]pyridin-2-yl)benzyl)nicotinamide;
15) N-(4-(oxazolo[4,5-c]pyridin-2-yl)benzyl)nicotinamide;
16) N-(4-(oxazolo[4,5-b]pyridin-2-yl)benzyl)nicotinamide;
17) N-(4-(benzo[d]thiazol-2-yl)benzyl)nicotinamide;
18) N-(4-(5-isopropylbenzo[d]oxazol-2-yl)phenyl)nicotinamide;
19) methyl 4-(nicotinamido)benzoate;
20) isopropyl 4-(nicotinamido)benzoate;
20) cyclohexyl 4-(nicotinamido)benzoate;
21) N-(4-(benzofuran-2-carbonyl)phenyl)nicotinamide;
22) N-(4-(piperidin-1-ylsulfonyl)benzyl)nicotinamide;
23) N-(4-(morpholinosulfonyl)benzyl)nicotinamide;
24) N-(4-([1,2,4]triazolo[3,4-b][1,3,4]thiadiazol-6-yl)phenyl)nicotinamide;
25) N-(4-(3-methyl-[1,2,4]triazolo[3,4-b][1,3,4]thiadiazol-6-yl)phenyl)nicotinamide;
26) N-(4-(3-ethyl-[1,2,4]triazolo[3,4-b][1,3,4]thiadiazol-6-yl)phenyl)nicotinamide;
27) N-(4-([1,2,4]triazolo[3,4-b][1,3,4]thiadiazol-6-yl)benzyl)nicotinamide;
28) N-(4-(3-methyl-[1,2,4]triazolo[3,4-b][1,3,4]thiadiazol-6-yl)benzyl)nicotinamide;
29) N-(4-(3-ethyl-[1,2,4]triazolo[3,4-b][1,3,4]thiadiazol-6-yl)benzyl)nicotinamide;
30) N-(4-((diethylamino)methyl)benzyl)nicotinamide;
31) N-(4-(piperidin-1-yl)benzyl)nicotinamide;
32) N-(4-(2-methyl-1H-imidazol-1-yl)benzyl)nicotinamide;
33) N-(4-(pyridin-2-ylmethoxy)benzyl)nicotinamide;
34) N-ethyl-N-(4-(nicotinamidomethyl)benzyl)ethanaminium;
35) (E)-N-(3-(indolin-1-yl)propyl)-3-(pyridin-3-yl)acrylamide;
36) (2E, N'Z)—N'-(3-methylbenzo[d]thiazol-2(3H)-ylidene)-3-(pyridin-3-yl)acrylohydrazide;
37) (E)-1-(44(2-(furan-2-yl)thiazol-4-yl)methyl)piperazin-1-yl)-3-(pyridin-3-yl)prop-2-en-1-one;
38) (E)-N-(2-(3-(pyridin-3-yl)acryloyl)-1,2,3,4-tetrahydroisoquinolin-7-yl)isonicotinamide;
39) (S, E)-1-(3-(5-isopropyl-7-(trifluoromethyl)pyrazolo[1,5-a]pyrimidin-2-yl)pyrrolidin-1-yl)-3-(pyridin-3-yl)prop-2-en-1-one;
40) N-(2-(nicotinamido)ethyl)-3-(p-tolyl)-1,2,4-oxadiazole-5-carboxamide;
41) 3-(4-chlorophenyl)-N-(2-(nicotinamido)ethyl)-1,2,4-oxadiazole-5-carboxamide;
42) N-(2-(nicotinamido)ethyl)-3-(thiophen-2-yl)-1,2,4-oxadiazole-5-carboxamide;
43) 3-(4-methoxyphenyl)-N-(2-(nicotinamido)ethyl)-1,2,4-oxadiazole-5-carboxamide;
44) N-(2-(nicotinamido)ethyl)quinoline-7-carboxamide;
45) N-(2-(nicotinamido)ethyl)isoquinoline-3-carboxamide;
46) N-(2-(nicotinamido)ethyl)quinoline-3-carboxamide;
47) N-methylisonicotinamide;
48) N,4-dimethylbenzamide;
49) N-(2-(3,4-dimethylphenyl)benzo[d]oxazol-5-yl)nicotinamide;
50) methyl 4-(2-(imidazo[1,2-a]pyridine-6-carboxamido)ethyl)benzoate;
51) N-(2-(nicotinamido)ethyl)quinoline-2-carboxamide; and
52) N-(2-(nicotinamido)ethyl)benzo[d]thiazole-2-carboxamide.

In the present invention, the compounds represented by Chemical Formula 1 and Chemical Formula 18 can be prepared by the following Reaction Scheme 1, but are not limited thereto:

[Reaction Scheme 1]

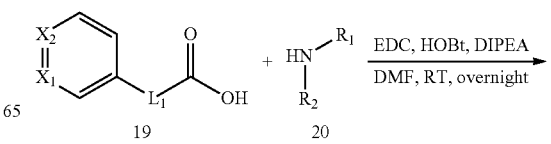

-continued

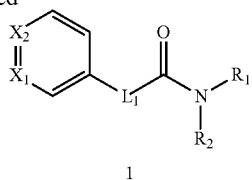

1

In the Reaction Scheme 1, $X_1$, $X_2$, $L_1$, $R_1$ and $R_2$ are each as defined in the Chemical Formula 1.

As a specific example, a compound represented by Chemical Formula 1 are synthesized by dissolving an acid represented by the Chemical Formula 19 and an amine compound represented by the Chemical Formula 20 in a solvent such as DMF (dimethylformamide) in the presence of EDC (1-(3-dimethylaminopropyl)-3-ethylcarbodiimide hydrochloride), HOBt (1-hydroxybenzotriazole monohydrate) and DIPEA (N,N-diisopropylethylamine) and refluxing for 12 to 36 hours.

Also, in the present invention, the compounds represented by Chemical Formula 2 can be prepared by the following Reaction Scheme 2, but are not limited thereto:

[Reaction Scheme 2]

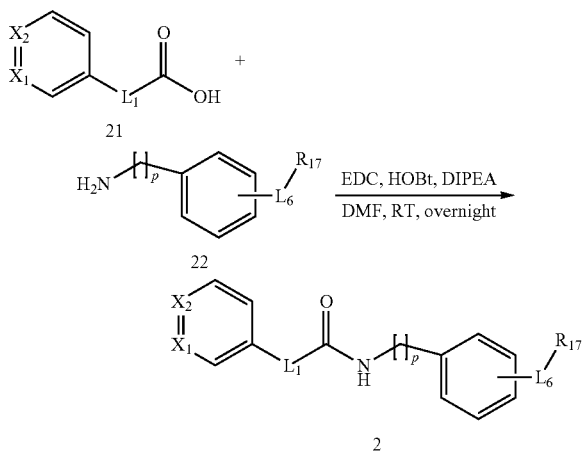

In the Reaction Scheme 2, $X_1$, $X_2$, $L_1$, $L_6$, p and $R_{17}$ are each as defined in the Chemical Formula 2.

As a specific example, a compound represented by Chemical Formula 2 are synthesized by dissolving an acid represented by the Chemical Formula 21 and an amine compound represented by the Chemical Formula 22 in a solvent such as DMF (dimethylformamide) in the presence of EDC (1-(3-dimethylaminopropyl)-3-ethylcarbodiimide hydrochloride), HOBt (1-hydroxybenzotriazole monohydrate) and DIPEA (N,N-diisopropylethylamine) and refluxing for 12 to 36 hours.

In the present invention, the compound represented by Chemical Formula 1 or Chemical Formula 18 can prevent, improve or treat the NamPT-related diseases by effectively inhibiting the activity of nicotinamide phospholibosyl transferase (NamPT).

In the present invention, the NamPT-related diseases are at least one selected from the group consisting of cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosis, multiple sclerosis, psoriatic arthritis, ankylosing spondylitis, graft-versus-host disease, Alzheimer's disease, cerebrovascular accident, atherosclerosis, diabetes, glomerulonephritis, and metabolic syndrome, and preferably, it may be a cancer.

In the present invention, the cancer is at least on selected from the group consisting of liver cancer, biliary cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, lymphoma, squamous cell cancer, kidney cancer, urethral cancer, bladder cancer, head and neck cancer, brain cancer and central nervous system cancer, preferably it may be lung cancer or gastric cancer.

The present invention also provides a pharmaceutically acceptable salt of a compound represented by the Chemical Formula 1 or Chemical Formula 18. Pharmaceutically acceptable salts should be low in toxicity to humans and should not adversely affect the biological activity and physicochemical properties of the parent compound. Pharmaceutically acceptable salts include, pharmaceutically acceptable free acids and acid addition salts of basic compounds of Chemical Formula 1, but are not limited thereto.

Preferred salts of the compounds according to the invention include salts with inorganic or organic acids. The inorganic acid may be hydrochloric acid, sulfuric acid, nitric acid, phosphoric acid, perchloric acid, bromic acid, etc. Also, the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, citric acid, gluconic acid, tartaric acid, salicylic acid, malic acid, oxalic acid, benzoic acid, embonic acid, aspartic acid, glutamic acid, etc. Organic bases that can be used in the production of organic base addition salts include tris(hydroxymethyl)methylamine, dicyclohexylamine, and the like. Amino acids that can be used in the production of amino acid addition salts are natural amino acids such as alanine and glycine, etc. It will be apparent to those skilled in the art that other acid or base other than the exemplified inorganic acids, organic acids, organic bases and amino acids may be used.

The salt may be prepared by conventional methods. For example, the salt may be prepared by dissolving the compound of the Chemical Formula 1 or the Chemical Formula 18 in a solvent which can be mixed with water, such as methanol, ethanol, acetone, or 1,4-dioxane, and then adding free acid or free base followed by crystallizing.

Meanwhile, the compounds according to the present invention may have an asymmetric carbon center, and thus may be R or S isomers or racemic compounds, and all these optical isomers and mixtures may be included in the scope of the present invention.

In addition, the hydrate or solvate forms of the compounds of Chemical Formula 1 may be included within the scope of the present invention.

The present invention provides a pharmaceutical composition comprising a compound selected from the compounds represented by Chemical Formula 1 or Chemical Formula 18, a pharmaceutically acceptable salt thereof, an optical isomer, a hydrate and a solvate, as an active ingredient.

In the pharmaceutical composition according to the present invention, the compound represented by Chemical Formula 1 or Chemical Formula 18 can prevent, improve or treat the NamPT-related diseases by effectively inhibiting the activity of nicotinamide phospholibosyl transferase (NamPT).

In the present invention, the NamPT-related diseases are at least one selected from the group consisting of cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosis, multiple sclerosis, psoriatic arthritis, ankylosing spondylitis, graft-versus-host disease, Alzheimer's disease, cerebrovascular accident, atherosclerosis, diabetes, glomerulonephritis, and metabolic syndrome, and preferably, it may be a cancer.

In the present invention, the cancer is at least on selected from the group consisting of liver cancer, biliary cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, lymphoma, squamous cell cancer, kidney cancer, urethral cancer, bladder cancer, head and neck cancer, brain cancer and central nervous system cancer, preferably it may be lung cancer or gastric cancer.

The pharmaceutical composition of the present invention can provide a synergistic effect to NamPT inhibition by further comprising a compound represented by the following Chemical Formula 23:

[Chemical Formula 23]

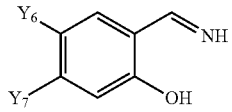

in the Chemical Formula 23,
$Y_6$ is hydrogen or halogen;
$Y_7$ is hydrogen or hydroxyl group (—OH).

According to one preferred embodiment of the present invention, in the Chemical Formula 23, $Y_6$ may be hydrogen and $Y_7$ may be hydroxyl group.

According to one preferred embodiment of the present invention, in the Chemical Formula 23, $Y_6$ may be halogen and $Y_7$ may be hydrogen.

According to one preferred embodiment of the present invention, the pharmaceutical composition of the present invention may comprise a compound represented by Chemical Formula 1 and the Chemical Formula 23.

According to one preferred embodiment of the present invention, the pharmaceutical composition of the present invention may comprise a compound represented by Chemical Formula 14 and the Chemical Formula 23.

According to one preferred embodiment of the present invention, the pharmaceutical composition according to the present invention comprises a compound represented by the Chemical Formula 14 and further comprises a compound represented by the Chemical Formula 23. In the Chemical Formula 14, the $X_2$ may be N, the $X_1$ may be C(H), the $R_{29}$ may be $C_1$-$C_3$ alkyl group and in the Chemical Formula 23, the $Y_6$ may be hydrogen and the $Y_7$ may be hydroxyl group.

According to one preferred embodiment of the present invention, the pharmaceutical composition according to the present invention comprises a compound represented by the Chemical Formula 14 and further comprises a compound represented by the Chemical Formula 23. In the Chemical Formula 14, the $X_2$ may be N, the $X_1$ may be C(H), the $R_{29}$ may be $C_1$-$C_3$ alkyl group and in the Chemical Formula 23, the $Y_6$ may be halogen and the $Y_7$ may be hydrogen.

According to one preferred embodiment of the present invention, the pharmaceutical composition according to the present invention comprises a compound represented by the Chemical Formula 14 and further comprises a compound represented by the Chemical Formula 23. In the Chemical Formula 14, the $X_2$ may be C($R_3$), the $X_1$ may be C(H), the $R_3$ and the $R_{29}$ may be each independently $C_1$-$C_3$ alkyl group and in the Chemical Formula 23, the $Y_6$ may be hydrogen and the $Y_7$ may be hydroxyl group.

According to one preferred embodiment of the present invention, the pharmaceutical composition according to the present invention comprises at least one compound selected from N-methylisonicotinamide, N,4-dimethylbenzamide, 4-chloro-2-(iminoethyl)phenol and 4-(iminoethyl)benzene-1,3-diol.

According to one preferred embodiment of the present invention, the pharmaceutical composition according to the present invention comprises a compound represented by the Chemical Formula 14 and comprises at least one selected from 4-chloro-2-(iminoethyl)phenol and 4-(iminoethyl)benzene-1,3-diol.

According to one preferred embodiment of the present invention, the pharmaceutical composition according to the present invention comprises at least one from N-methyl isonicotinamide and N,4-dimethylbenzamide, and further comprises at least one from 4-chloro-2-(iminoethyl)phenol and 4-(iminoethyl)benzene-1,3-diol.

According to one preferred embodiment of the present invention, the pharmaceutical composition according to the present invention comprises N-methyl isonicotinamide, and further comprises at least one from 4-chloro-2-(iminoethyl)phenol and 4-(iminoethyl)benzene-1,3-diol.

According to one preferred embodiment of the present invention, the pharmaceutical composition according to the present invention comprises N,4-dimethylbenzamide, and further may comprise at least one from 4-chloro-2-(iminoethyl)phenol and 4-(iminoethyl)benzene-1,3-diol, and more preferably 4-(iminoethyl)benzene-1,3-diol.

According to one preferred embodiment of the present invention, the pharmaceutical composition of the present invention may contain the compound represented by the Chemical Formula 14 and the compound represented by the Chemical Formula 23 in a weight ratio of 1:100 to 100:1, more preferably in a weight ratio of 40:60 to 60:40. In the present invention, when the two compounds are included beyond the weight ratio, the NamPT inhibitory effect may be significantly lowered.

In the present invention, "treatment" and "improvement" can include, without limitation, any action to improve or conducive to a NamPT related disease using a pharmaceutical composition.

In the present invention, "prevention" can include, without limitation, any action to block the symptoms or to suppress or delay the symptoms of NamPT related disease using a pharmaceutical composition.

The pharmaceutical composition of the present invention can be administered in combination with other anticancer drugs, thereby further enhancing the effect of radiation therapy on cancer stem cells.

Herein, the anticancer agents include at least one selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, olaparib, navelbine, fadrozole, tamoxifen, toremifene, testolactone, anastrozole, letrozole, vorozole, bicalutamide, lomustine, vorinostat, entinostat and carmustine, but it is not limited thereto.

According to the present invention, the pharmaceutical composition may be in the form of capsules, tablets, granules, injections, ointments, powders or beverages, and the pharmaceutical composition may be targeted to humans.

The pharmaceutical composition of the present invention is not limited to, but may be used as a formulation in the form of an oral preparation such as powders, granules, capsules, tablets, aqueous suspensions, etc., an external preparation, a suppository and a sterilized injection solution. The pharmaceutical composition of the present invention may include a pharmaceutically acceptable carrier. The pharmaceutically acceptable carrier may be a binder, a lubricant, a disintegrant, an excipient, a solubilizing agent, a dispersing agent, a stabilizer, a suspending agent, a pigment, a perfume or the like for oral administration and a buffer, a preservative, an analgesic agent, a solubilizer, an isotonic agent, a stabilizer and the like may be mixed and used for injections, and a base, an excipient, a lubricant, a preservative and the like may be used for topical administration. Formulations of the pharmaceutical compositions of the present invention may be prepared in a variety of ways by mixing with a pharmaceutically acceptable carrier as described above. For example, it can be prepared in the form of tablets, troches, capsules, elixirs, suspensions, syrups, wafers and the like in the case of oral administration. Injections may be prepared in the form of unit dosage ampoules or multiple doses. It may be formulated as other solutions, suspensions, tablets, capsules, sustained-release preparations and the like.

Meanwhile, Examples of carriers, excipients and diluents suitable for formulation include lactose, dextrose, sucrose, sorbitol, mannitol, xylitol, erythritol, malditol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil, etc. Further, it may further include fillers, anti-coagulants, lubricants, wetting agents, perfumes, emulsifiers, preservatives and the like.

The route of administration of the pharmaceutical compositions according to the present invention may be, but is not limited to, oral, intravenous, intramuscular, intraarterial, intramedullary, intradural, intracardiac, transdermal, subcutaneous, intraperitoneal, intranasal, intestinal, topical, sublingual or rectal. Oral or parenteral administration is preferred.

In the present invention, "parenteral" includes subcutaneous, intradermal, intravenous, intramuscular, intraarticular, intrasynovial, intrasternal, intradural, intralesional and intracranial injection or infusion techniques. The pharmaceutical compositions of the present invention may also be administered in the form of suppositories for rectal administration.

The pharmaceutical composition of the present invention may be changed according to various factors including the activity of the used specific compound, age, body weight, general health, sex, diet, time of administration, route of administration, rate of excretion, drug formulation and severity of specific diseases to be prevented or treated, and the dosage of the pharmaceutical composition varies depending on the condition of the patient, the body weight, the degree of disease, the type of drug, the route of administration, and the period of time, but may be suitably selected by those skilled in the art and is preferably from 0.0001 to 50 mg/kg or 0.001 to 50 mg/kg per a day. The administration may be carried out once a day or divided into several times. The dosage amount is not intended to limit the scope of the invention in any way. The pharmaceutical composition according to the present invention can be formulated into pills, sugar-coated tablets, capsules, solutions, gels, syrups, slurries, suspensions.

The pharmaceutical composition of the present invention can be used alone or in combination with methods using surgery, radiotherapy, hormone therapy, chemotherapy and biological response modifiers.

The present invention provides a food composition comprising a compound selected from a compound represented by the Chemical Formula 1 or the Chemical Formula 18, a pharmaceutically acceptable salt thereof, an optical isomer, a hydrate and a solvate thereof, as an active ingredient.

According to food composition of the present invention, the compound represented by Chemical Formula 1 or Chemical Formula 18 can prevent or improve the NamPT-related diseases by effectively inhibiting the activity of nicotinamide phospholibosyl transferase (NamPT).

In the present invention, the NamPT-related diseases are at least one selected from the group consisting of cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosis, multiple sclerosis, psoriatic arthritis, ankylosing spondylitis, graft-versus-host disease, Alzheimer's disease, cerebrovascular accident, atherosclerosis, diabetes, glomerulonephritis, and metabolic syndrome, and preferably, it may be a cancer.

In the present invention, the cancer is at least on selected from the group consisting of liver cancer, biliary cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, lymphoma, squamous cell cancer, kidney cancer, urethral cancer, bladder cancer, head and neck cancer, brain cancer and central nervous system cancer, preferably it may be lung cancer or gastric cancer.

The food composition of the present invention can provide a synergistic effect to NamPT inhibition by further comprising a compound represented by the Chemical Formula 23.

However, description regarding the compound represented by Chemical Formula 23 is the same as that of the pharmaceutical composition, and details thereof will be omitted below.

The food composition of the present invention may be manufactured in the form of various foods such as beverage, gum, tea, vitamin complex, powder, granule, tablet, capsule, snack, rice cakes, bread and the like. Since the food composition of the present invention is composed of a plant extract having little toxicity and side effects, it can be safely used for long-term use for prophylactic purposes.

When the compound of the present invention is contained in the food composition, the amount thereof may be added 0.1 to 50% of the total weight.

Here, when the food composition is prepared in a beverage form, there are no particular limitations other than containing the food composition in the indicated ratios, and may contain various flavors or natural carbohydrates as an additional ingredient such as general beverages. Namely, as natural carbohydrates, monosaccharide such as glucose, etc., disaccharides such as fructose, etc. and polysaccharides such as sucrose, etc., and typical sugar such as dextrin and cyclodextrin, etc. and sugar alcohols such as xylitol, sorbitol and erythritol, etc. can be included. Examples of the flavoring agents include natural flavoring agents (thaumatin and stevia extract (e.g. rebaudioside A and glycyrrhizin, etc.) and synthetic flavorings (e.g. saccharin and aspartame, etc.) and the like.

In addition, the food composition of the present invention can contain various nutrients, vitamins, minerals (electrolytes), a flavoring agent such as synthetic flavoring agents and natural flavoring agents, coloring agents, pectic acid and its salts, alginic acid and its salts, organic acid, protective colloid thickener, a pH adjusting agent, a stabilizer, a preservative, a glycerin, an alcohol, a carbonating agent used in a carbonated drink, and the like.

These ingredients can be used independently or in combination. The proportion of such additives is not so critical, but is generally selected in the range of 0.1 to about 50 parts by weight per 100 parts by weight of the composition of the present invention.

The present invention provides a cosmetic composition comprising a compound selected from a compound represented by Chemical Formula 1 or Chemical Formula 18, a pharmaceutically acceptable salt thereof, an optical isomer, a hydrate and a solvate, as an active ingredient.

In the cosmetic composition according to the present invention, the compound represented by Chemical Formula 1 or Chemical Formula 18 can prevent or improve the NamPT-related diseases by effectively inhibiting the activity of nicotinamide phospholibosyl transferase (NamPT).

In the present invention, the NamPT related diseases may be dermatitis, atopic dermatitis or psoriasis.

The cosmetic composition of the present invention can provide a synergistic effect to NamPT inhibition by further comprising a compound represented by the Chemical Formula 23.

However, description regarding the compound represented by Chemical Formula 23 is the same as that of the pharmaceutical composition, and details thereof will be omitted below.

The cosmetic composition according to the present invention can be prepared in the form of toner, nutrition lotion, nutrition essence, massage cream, cosmetic bath additives, body lotion, body milk, bath oil, baby oil, baby powder, shower gel, shower cream, sunscreen lotion, sunscreen cream, suntan cream, skin lotion, skin cream, UV protection cosmetic, cleansing milk, hair loss treatment agent (cosmetic), face and body lotion, face and body cream, skin whitening cream, hand lotion, hair lotion, cosmetic cream, jasmine oil, bath soap, water soap, beauty soap, shampoo, hand cleaner, medicinal soap (non-medical), cream soap, facial wash, body cleansing agent, scalp detergent, hair conditioner, cosmetic soap, tooth whitening gel, toothpaste, and the like. For this, the composition of the present invention may further comprise a solvent commonly used in the production of a cosmetic composition, or a suitable carrier, excipient or diluent.

The type of the solvent that can be further added to the cosmetic composition of the present invention is not particularly limited and for example, water, saline, DMSO or a combination thereof can be used. Examples of the carrier, excipient or diluent include purified water, oil, wax, fatty acids, fatty alcohols, fatty acid esters, surfactants, humectants, thickeners, antioxidants, viscosity stabilizers, chelating agents, buffers, and lower alcohols, etc., but they are not limited thereto. In addition, it may contain a whitening agent, a moisturizer, a vitamin, an ultraviolet screening agent, a perfume, a dye, an antibiotic, an antibacterial agent and an antifungal agent, if necessary.

As the oil, hydrogenated vegetable oil, castor oil, cottonseed oil, olive oil, palm oil, jojoba oil and avocado oil may be used and examples of the wax include beewax, spermaceti wax, carnauba, candelilla, montan, ceresin, liquid paraffin, lanolin.

As the fatty acid, stearic acid, linoleic acid, linolenic acid and oleic acid may be used. As the fatty acid alcohol, cetyl alcohol, octyldodecanol, oleyl alcohol, panthenol, lanolin alcohol, stearyl alcohol and hexadecanol may be used. As the fatty acid ester, isopropyl myristate, isopropyl palmitate and butyl stearate may be used. As the surfactant, cationic surfactants, anionic surfactants and nonionic surfactants known in the art can be used, and as far as possible, surfactants derived from natural materials are preferable.

In addition, a moisture absorbent, a thickener, an antioxidant and the like widely known in the field of cosmetics can be included, and the kind and amount thereof are well known in the art.

The present invention also relates to a method of preventing or treating NamPT-related diseases comprising a step of administering a compound selected from a compound of the Chemical Formula 1 or Chemical Formula 18 of the present invention, a pharmaceutically acceptable salt, an optical isomer, a hydrate and a solvate thereof, to a subject in need of administration (e.g. humans) in a pharmaceutically effective amount.

In the present invention, the NamPT-related diseases are at least one selected from the group consisting of cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosis, multiple sclerosis, psoriatic arthritis, ankylosing spondylitis, graft-versus-host disease, Alzheimer's disease, cerebrovascular accident, atherosclerosis, diabetes, glomerulonephritis, and metabolic syndrome, and preferably, it may be a cancer.

In the present invention, the cancer is at least on selected from the group consisting of liver cancer, biliary cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, lymphoma, squamous cell cancer, kidney cancer, urethral cancer, bladder cancer, head and neck cancer, brain cancer and central nervous system cancer, preferably it may be lung cancer or gastric cancer.

The "administration" in the present invention means providing a certain compound of the present invention to a subject in any suitable manner.

The "subject" in which the administration is required in the present invention may include both mammals and non-mammals. Here, examples of the mammals include humans, non-human primates such as chimpanzees, and other apes and monkey species; livestock animals such as cattle, horses, sheep, goats, pigs; breeding animals such as rabbits, dogs and cats; laboratory animals such as rodents, e.g. rats, mice and guinea pigs, and the like, but it is not limited thereto. Also, examples of non-mammals in the present invention include birds and fishes, and the like, but it is not limited thereto.

The formulation of the compound to be administered as described above is not particularly limited and may be administered in the form of a solid form, a liquid formulation or an aerosol formulation for aspiration and a solid form preparation intended to be converted to a liquid form preparation for oral or parenteral administration immediately prior to use, for example, oral formulation such as powders, granules, capsules, tablets, aqueous suspensions, etc., and formulation in the form of external preparations, suppositories and sterile injectable solutions, but it is not limited thereto.

In addition, in the administration of the present invention, a pharmaceutically acceptable carrier may be further administered together with the compound of the present invention. Here, the pharmaceutically acceptable carrier may be a binder, a lubricant, a disintegrant, an excipient, a solubilizing agent, a dispersing agent, a stabilizer, a suspending agent, a pigment, a perfume or the like for oral administration and a buffer, a preservative, an analgesic agent, a solubilizer, an isotonic agent, a stabilizer and the like may be mixed and used for injections, and a base, an excipient, a lubricant, a preservative and the like may be used for topical administration. Formulations of the compound of the present invention may be prepared in a variety of ways by mixing with a pharmaceutically acceptable carrier as described above. For example, it can be prepared in the form of tablets, troches, capsules, elixirs, suspensions, syrups, wafers and the like in the case of oral administration. Injections may be prepared in the form of unit dosage ampoules or multiple doses. It may be formulated as other solutions, suspensions, tablets, capsules, sustained-release preparations and the like.

Meanwhile, Examples of carriers, excipients and diluents suitable for formulation include lactose, dextrose, sucrose, sorbitol, mannitol, xylitol, erythritol, malditol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil, etc. Further, it may further include fillers, anti-coagulants, lubricants, wetting agents, perfumes, emulsifiers, preservatives and the like.

The route of administration of the pharmaceutical compositions according to the present invention may be, but is not limited to, oral, intravenous, intramuscular, intraarterial, intramedullary, intradural, intracardiac, transdermal, subcutaneous, intraperitoneal, intranasal, intestinal, topical, sublingual or rectal. Oral or parenteral administration is preferred.

In the present invention, "parenteral" includes subcutaneous, intradermal, intravenous, intramuscular, intraarticular, intrasynovial, intrasternal, intradural, intralesional and intracranial injection or infusion techniques. The pharmaceutical compositions of the present invention may also be administered in the form of suppositories for rectal administration.

In the present invention, "pharmaceutically effective amount" refers to a sufficient amount of an agent to provide a desired biological result. The results may be indicative of a disease, a reduction and/or mitigation in symptoms or causes, or any other desired change in the biological system. For example, "effective amount" for therapeutic use is the amount of a compound disclosed the present invention that is required to provide clinically significant reduction in disease. Appropriate "effective" amounts in any individual case may be determined by one of ordinary skill in the art using routine experiment. Thus, the expression of "effective amount" generally refers to the amount that the active substance has a therapeutic effect. In the present invention, the active substance is an inhibitor of the formation of nicotinamide phosphoribosyl transferase (NAMPT).

The compound of the present invention may be changed according to various factors including the activity of the used specific compound, age, body weight, general health, sex, diet, time of administration, route of administration, rate of excretion, drug formulation and severity of specific diseases to be prevented or treated, and the dosage of the compound varies depending on the condition of the patient, the body weight, the degree of disease, the type of drug, the route of administration, and the period of time, but may be suitably selected by those skilled in the art and is preferably from 0.0001 to 50 mg/kg or 0.001 to 50 mg/kg per a day. The administration may be carried out once a day or divided into several times. The dosage amount is not intended to limit the scope of the invention in any way. The pharmaceutical composition according to the present invention can be formulated into pills, sugar-coated tablets, capsules, solutions, gels, syrups, slurries, suspensions.

The compound of the present invention can be used alone or in combination with methods using surgery, radiotherapy, hormone therapy, chemotherapy and biological response modifiers.

Hereinafter, the present invention will be described in more detail based on the following Synthesis Example and Example, but the present invention is not limited thereto.

EXAMPLE

[Preparation Example 1] Preparation of Intermediate 1((4-(6-methylbenzo[d]oxazol-2-yl)phenyl)methanamine)

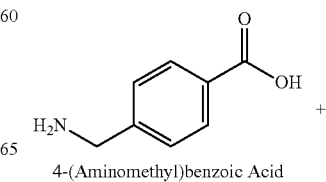

4-(Aminomethyl)benzoic Acid

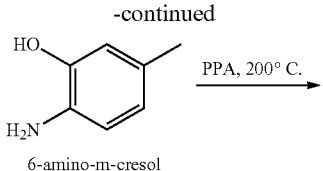

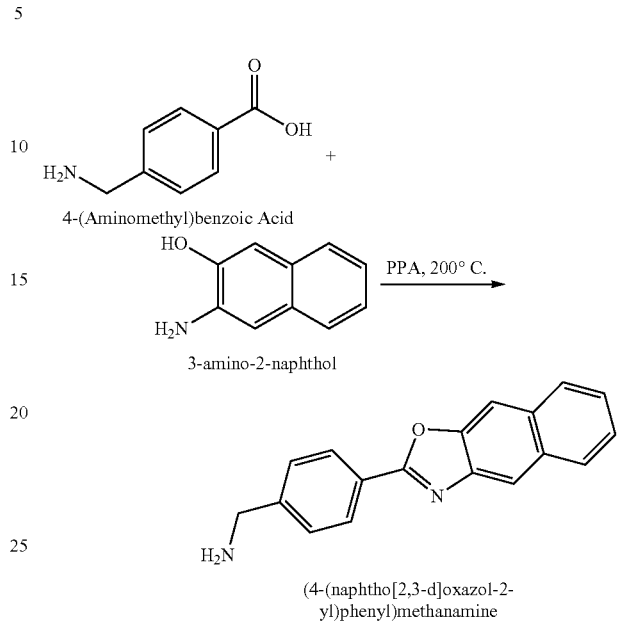

4-(Aminomethyl)benzoic acid (1.99 mmol) and 6-amino-m-cresol (1.99 mmol) were dissolved in polyphosphoric acid (PPA, excess) and refluxed at 200° C. for 12 hours. The reactant was dissolved in an excess of distilled water and precipitated salt was filtered, vacuum dried and used in the next step without further purification.

[Preparation Example 2] Preparation of Intermediate 2((4-(6-chlorobenzo[d]oxazol-2-yl)phenyl)methanamine)

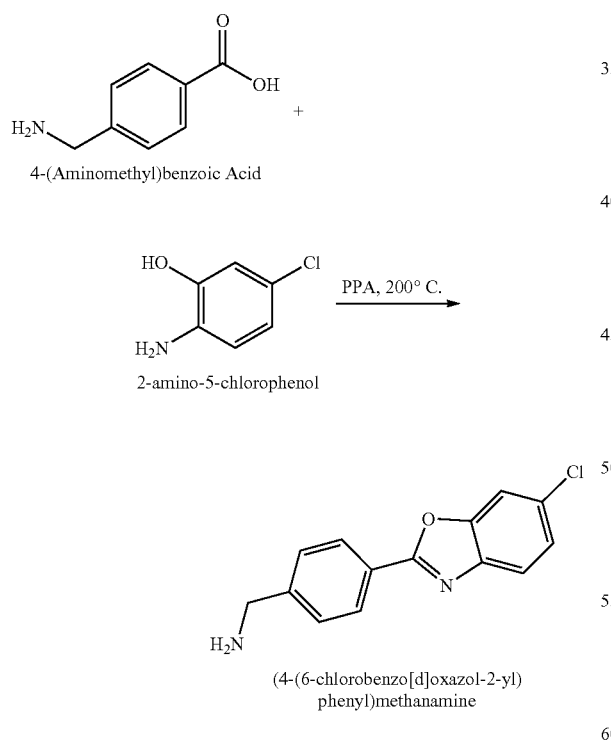

4-(Aminomethyl)benzoic acid (1.32 mmol) and 2-amino-5-chlorophenol (1.32 mmol) were dissolved in polyphosphoric acid (PPA, excess) and refluxed at 200° C. for 12 hours. The reactant was dissolved in an excess of distilled water and precipitated salt was filtered, vacuum dried and used in the next step without further purification.

[Preparation Example 3] Preparation of Intermediate 3(4-(naphtho[2,3-d]oxazol-2-yl)phenyl)methanamine)

4-(Aminomethyl)benzoic acid (1.32 mmol) and 3-amino-2-naphthol (1.32 mmol) were dissolved in polyphosphoric acid (PPA, excess) and refluxed at 200° C. for 12 hours. The reactant was dissolved in an excess of distilled water and precipitated salt was filtered, vacuum dried and used in the next step without further purification.

[Synthesis Example 1] Preparation of N-(4-(6-methylbenzo[d]oxazol-2-yl)benzyl)nicotinamide

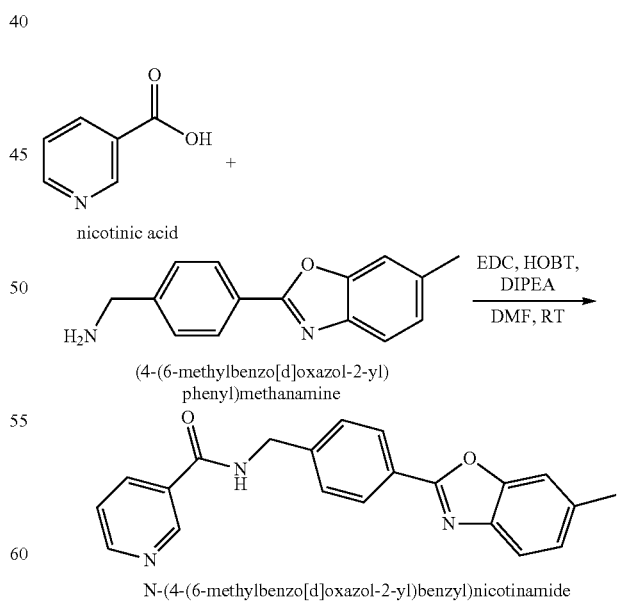

Nicotinic acid (1.06 mmol), (4-(6-methylbenzo[d]oxazol-2-yl)phenyl)methanamine prepared in the Preparation Example 1 (1.06 mmol), EDC (1-(3-dimethylaminopropyl)-3-ethylcarbodiimide hydrochloride, 2.11 mmol), HOBt (1-hydroxybenzotriazole monohydrate, 2.11 mmol) and DIPEA (N,N-diisopropylethylamine, 3.17 mmol) were dissolved in DMF (dimethylformamide, 4 ml) and refluxed overnight at room temperature. Thereafter, the reaction mixture was transferred to a separate funnel, followed by the addition of an aqueous solution of $NH_4Cl$ and three extractions with EA (ethyl acetate). The extract was dried with $Na_2SO_4$ and concentrated under reduced pressure. The reaction residue was treated with dichloromethane (MC) and hexane (HX) to obtain a white solid. NMR spectrum of N-(4-(6-methylbenzo[d]oxazol-2-yl)benzyl)nicotinamide (hereinafter referred to as "A4276") prepared as described above is shown in FIG. 1.

$^1$H NMR (400 MHz, DMSO-$d_6$): δ 9.36 (t, J=5.6 Hz, 1H), 9.09 (d, J=1.2 Hz, 1H), 8.74 (dd, J=4.6, 1.3 Hz, 1H), 8.27 (d, J=8.0 Hz, 1H), 8.16 (d, J=8.2 Hz, 2H), 7.67 (d, J=8.1 Hz, 1H), 7.62-7.51 (m, 4H), 7.23 (d, J=8.0 Hz, 1H), 4.62 (d, J=5.7 Hz, 2H), 2.47 (s, 3H).

[Synthesis Example 2] Preparation of N-(4-(6-chlorobenzo[d]oxazol-2-yl)benzyl)nicotinamide

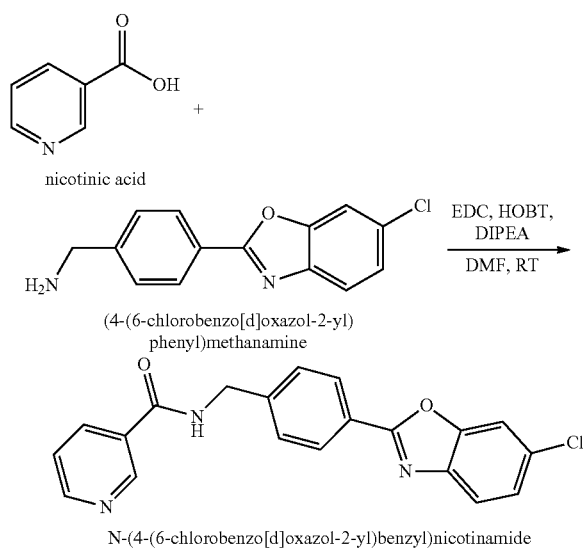

Figure 2:
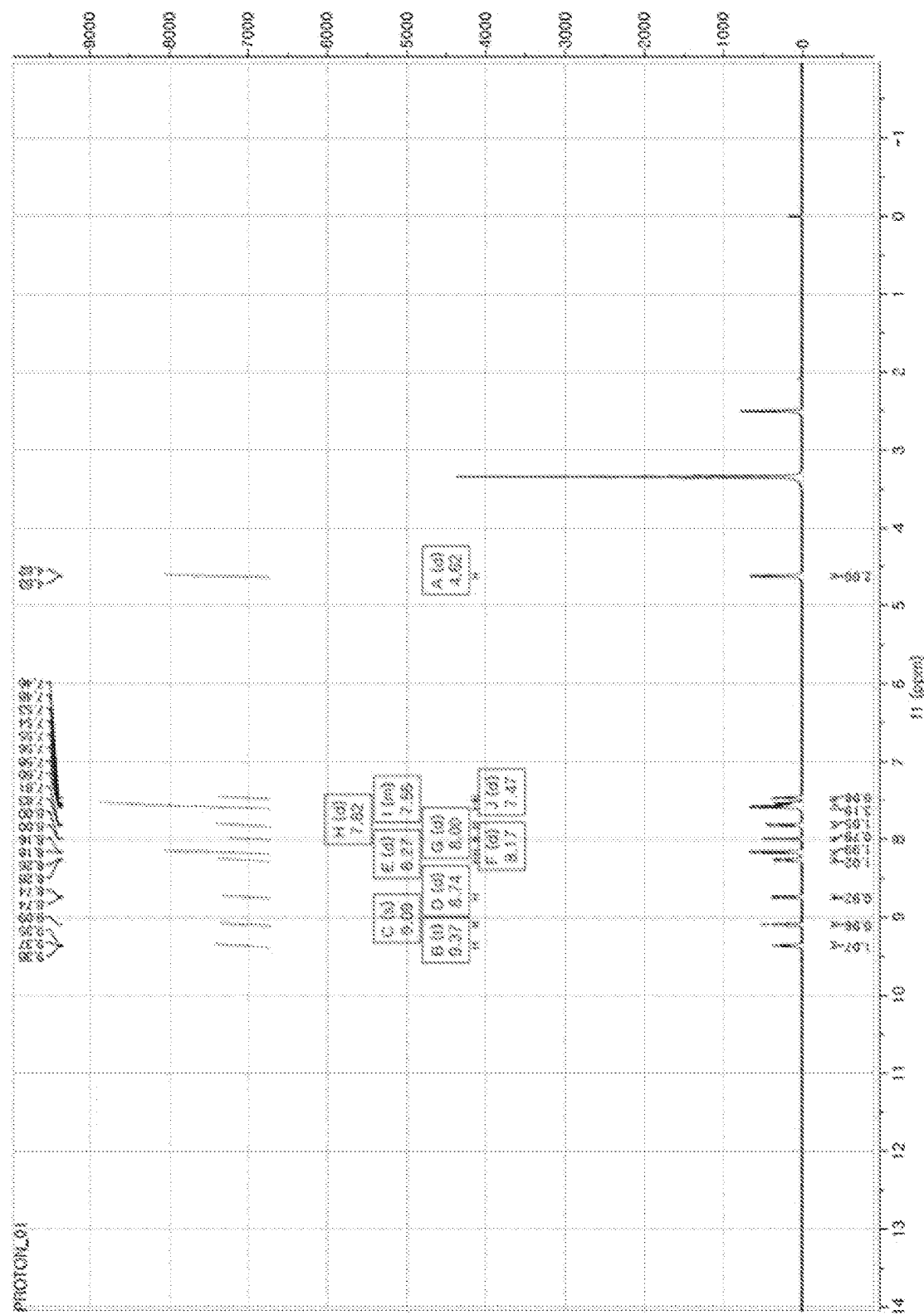
FIG. 2 shows NMR spectrum of N-(4-(6-chlorobenzo[d]oxazol-2-yl) benzyl)nicotinamide (A4266) prepared in Synthesis Example 2 according to an example of the present invention.

Nicotinic acid (0.77 mmol), (4-(6-chlorobenzo[d]oxazol-2-yl)phenyl)methanamine prepared in the Preparation Example 2 (0.77 mmol), EDC (1-(3-dimethylaminopropyl)-3-ethylcarbodiimide hydrochloride, 1.54 mmol), HOBt (1-hydroxybenzotriazole monohydrate, 1.54 mmol) and DIPEA (N,N-diisopropylethylamine, 2.31 mmol) were dissolved in DMF (dimethylformamide, 4 ml) and refluxed overnight at room temperature. Thereafter, the reaction mixture was transferred to a separate funnel, followed by the addition of an aqueous solution of $NH_4Cl$ and three extractions with EA (ethyl acetate). The extract was dried with $Na_2SO_4$ and concentrated under reduced pressure. The reaction residue was treated with dichloromethane (MC) and hexane (HX) to obtain a white solid (hereinafter referred to as "A4266"). NMR spectrum of N-(4-(6-chlorobenzo[d]oxazol-2-yl)benzyl)nicotinamide prepared as described above is shown in FIG. 2.

$^1$H NMR (400 MHz, DMSO-$d_6$): δ 9.37 (t, J=5.6 Hz, 1H), 9.09 (s, 1H), 8.74 (d, J=4.0 Hz, 1H), 8.27 (d, J=7.9 Hz, 1H), 8.17 (d, J=8.1 Hz, 2H), 8.00 (d, J=1.3 Hz, 1H), 7.82 (d, J=8.5 Hz, 1H), 7.62-7.51 (m, 3H), 7.47 (d, J=8.5 Hz, 1H), 4.62 (d, J=5.6 Hz, 2H).

[Synthesis Example 3] Preparation of N-(4-(naphtho[2,3-d]oxazol-2-yl)benzyl)nicotinamide

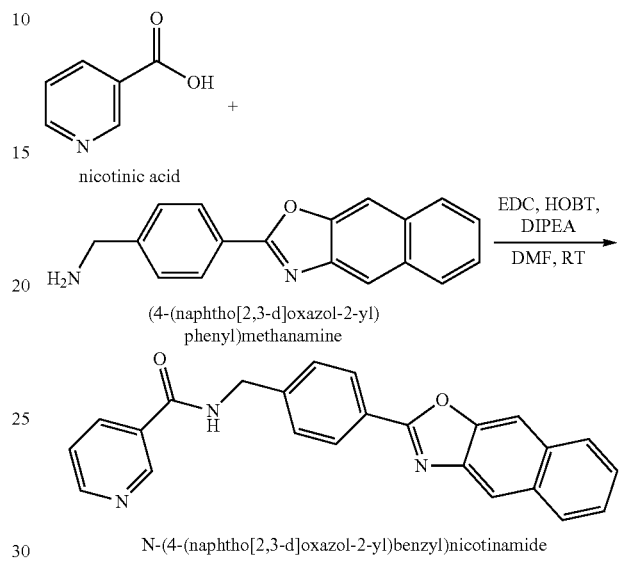

Figure 3:
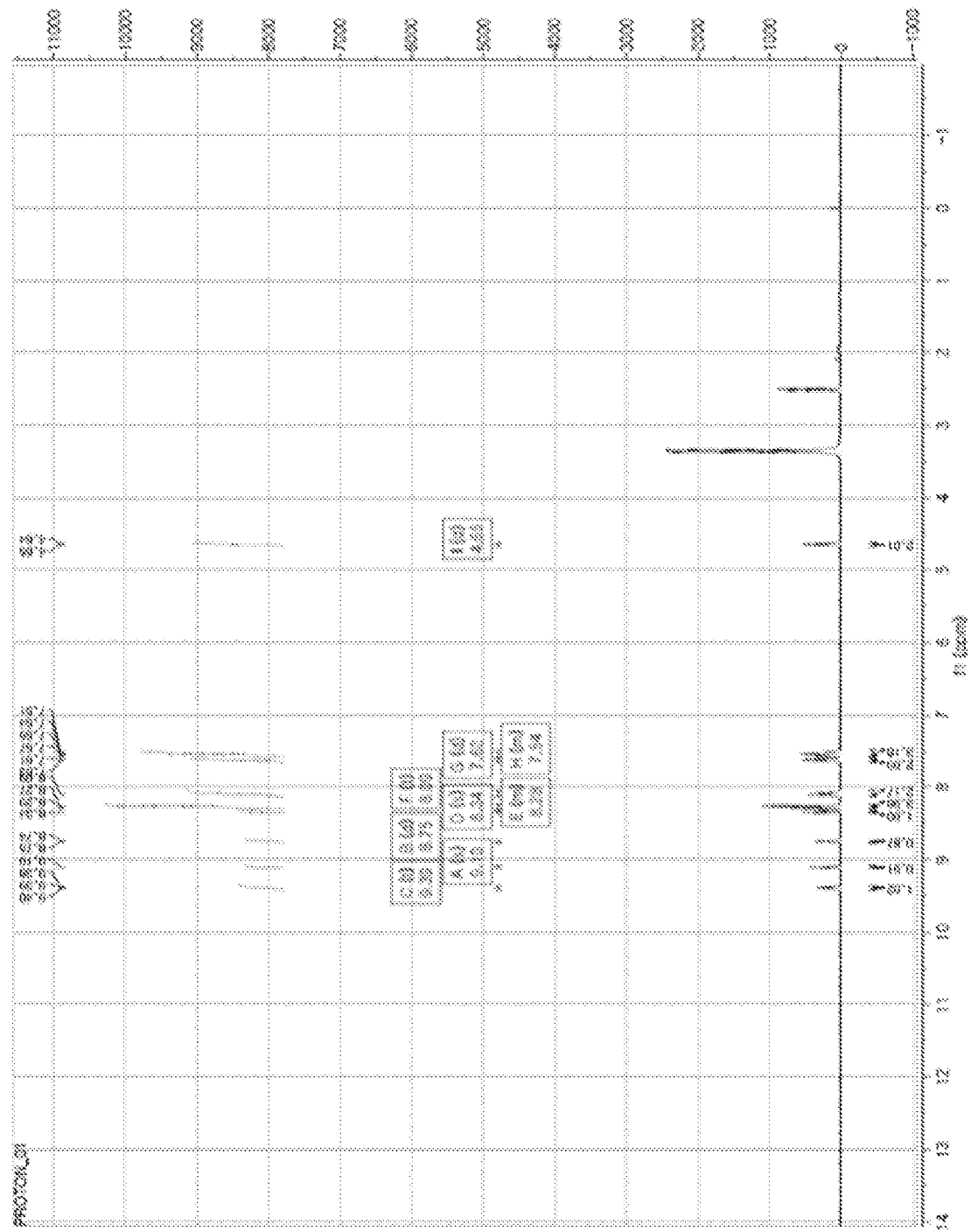
FIG. 3 shows NMR spectrum of N-(4-(6-methylbenzo[d]oxazol-2-yl) benzyl)nicotinamide (A4265) prepared in Synthesis Example 3 according to an example of the present invention.

Nicotinic acid (0.73 mmol), (4-(naphtho[2,3-d]oxazol-2-yl)phenyl)methanamine prepared in the Preparation Example 2 (0.73 mmol), EDC (1-(3-dimethylaminopropyl)-3-ethylcarbodiimide hydrochloride, 1.46 mmol), HOBt (1-hydroxybenzotriazole monohydrate, 1.46 mmol) and DIPEA (N,N-diisopropylethylamine, 2.19 mmol) were dissolved in DMF (dimethylformamide, 4 ml) and refluxed overnight at room temperature. Thereafter, the reaction mixture was transferred to a separate funnel, followed by the addition of an aqueous solution of $NH_4Cl$ and three extractions with EA (ethyl acetate). The extract was dried with $Na_2SO_4$ and concentrated under reduced pressure. The reaction residue was treated with dichloromethane (MC) and hexane (HX) to obtain a white solid (hereinafter referred to as "A4265"). NMR spectrum of N-(4-(naphtho[2,3-d]oxazol-2-yl)benzyl)nicotinamide prepared as described above is shown in FIG. 3.

$^1$H NMR (400 MHz, DMSO-$d_6$): δ 9.39 (t, J=5.5 Hz, 1H), 9.10 (s, 1H), 8.75 (d, J=3.4 Hz, 1H), 8.34 (s, 1H), 8.31-8.24 (m, 4H), 8.09 (t, J=8.6 Hz, 2H), 7.62 (d, J=8.1 Hz, 2H), 7.58-7.49 (m, 3H), 4.65 (d, J=5.5 Hz, 2H).

[Synthesis Example 4] Preparation of N-(4-(oxazolo[4,5-c]pyridin-2-yl)benzyl)nicotinamide

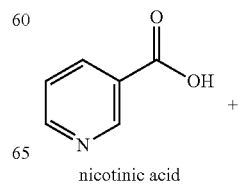

J=5.5 Hz), 8.29-8.25 (m, 1H), 8.22 (d, 2H, J=8.3 Hz), 7.91 (dd, 1H, J=5.5, 0.7 Hz), 7.61 (d, 2H, J=8.3 Hz), 7.55 (dd, 1H, J=7.9, 4.9 Hz), 4.63 (d, 2H, J=5.8 Hz).

Synthesis Example 5 to 33

[Reaction Scheme 3]

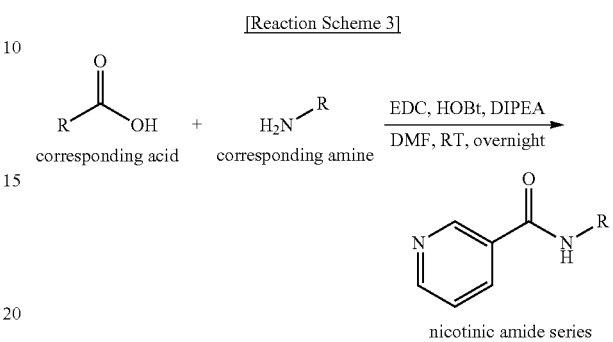

nicotinic amide series

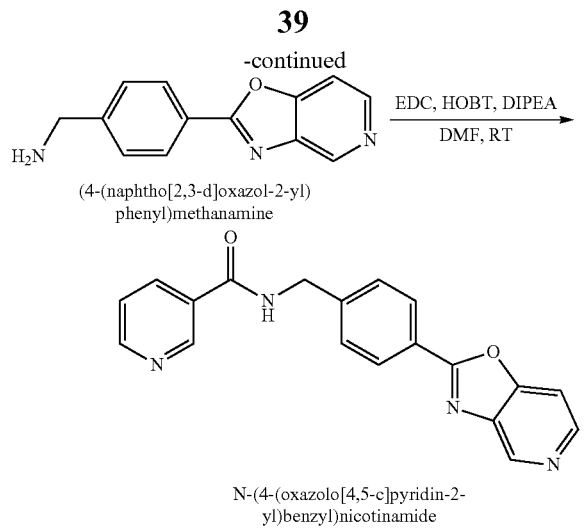

Figure 4:
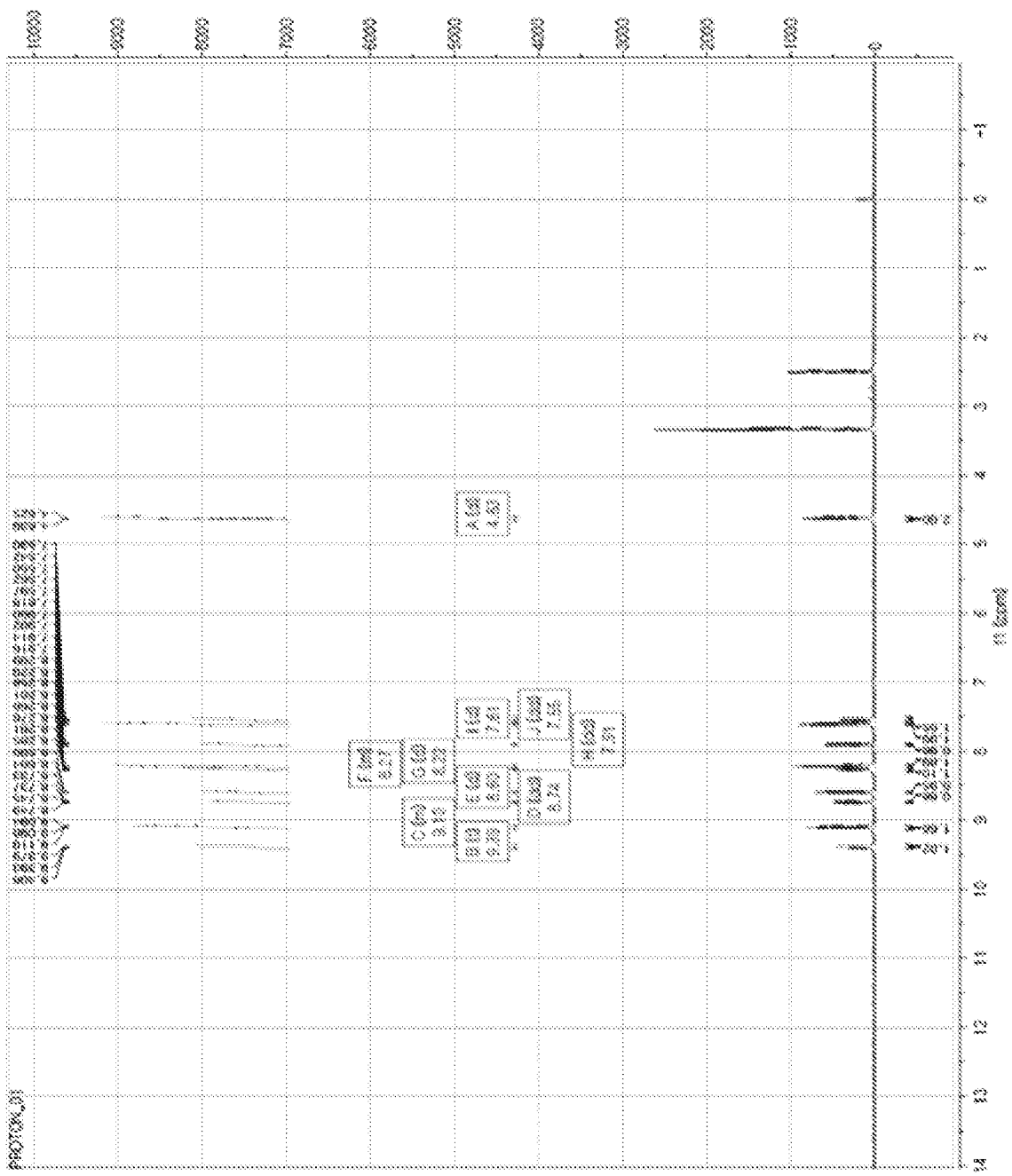
FIG. 4 shows NMR spectrum of N-(4-(oxazolo[4,5-c]pyridin-2-yl)benzyl)nicotinamide (B1471) prepared in Synthesis Example 4 according to an example of the present invention.

Nicotinic acid (2.44 mmol), (4-(naphtho[2,3-d]oxazol-2-yl)phenyl)methanamine (2.44 mmol), EDC (1-(3-dimethylaminopropyl)-3-ethylcarbodiimide hydrochloride, 4.87 mmol), HOBt (1-hydroxybenzotriazole monohydrate, 4.87 mmol) and DIPEA (N,N-diisopropylethylamine, 7.31 mmol) were dissolved in DMF (dimethylformamide, 10 ml) and refluxed overnight at room temperature. Thereafter, the reaction mixture was transferred to a separate funnel, followed by the addition of an aqueous solution of NH$_4$Cl and three extractions with EA (ethyl acetate). The extract was dried with Na$_2$SO$_4$ and concentrated under reduced pressure. The reaction residue was treated with dichloromethane (MC) and hexane (HX) to obtain a white solid (hereinafter referred to as "B1471"). NMR spectrum of N-(4-(oxazolo[4,5-c]pyridin-2-yl)benzyl)nicotinamide prepared as described above is shown in FIG. 4.

$^1$H NMR (400 MHz, DMSO-d$_6$): δ 9.39 (t, 1H, J=5.8 Hz), 9.14-9.08 (m, 2H), 8.74 (dd, 1H, J=4.8, 1.5 Hz), 8.60 (d, 1H,

According to the above Reaction Scheme 3, acid (2.44 mmol) and amine (2.44 mmol) of the following Table 1, EDC (1-(3-dimethylaminopropyl)-3-ethylcarbodiimide hydrochloride, 4.87 mmol), HOBt (1-Hydroxybenzotriazole monohydrate, 4.87 mmol) and DIPEA (N,N-diisopropylethylamine, 7.31 mmol) were dissolved in DMF (dimethylformamide, 10 ml) and refluxed overnight at room temperature. Thereafter, the reaction mixture was transferred to a separate funnel, followed by the addition of an aqueous solution of NH$_4$Cl and three extractions with EA (ethyl acetate). The extract was dried with Na$_2$SO$_4$ and concentrated under reduced pressure. The reaction residue was purified by flash column chromatography (5% methanol in dichloromethane) and dried in a vacuum pump to produce the final compound shown in Table 2 below.

TABLE 1

| Synthesis Example | acid | Amine |
|---|---|---|
| Synthesis Example 5 | nicotinic acid | methyl 4-aminobenzoate |
| Synthesis Example 6 | nicotinic acid | isopropyl 4-aminobenzoate |
| Synthesis Example 7 | nicotinic acid | (4-(3-ethyl-[1,2,4]triazolo[3,4-b][1,3,4]thiadiazol-6-yl)phenyl)methanamine |

TABLE 1-continued

| Synthesis Example | acid | Amine |
|---|---|---|
| Synthesis Example 8 | nicotinic acid | 4-(3-methyl-[1,2,4]triazolo[3,4-b][1,3,4]thiadiazol-6-yl)benzylamine |
| Synthesis Example 9 | nicotinic acid | 4-(benzo[d]thiazol-2-yl)benzylamine |
| Synthesis Example 10 | nicotinic acid | 4-(benzo[d]oxazol-2-yl)benzylamine |
| Synthesis Example 11 | nicotinic acid | 4-(oxazolo[4,5-b]pyridin-2-yl)benzylamine |
| Synthesis Example 12 | nicotinic acid | 4-(5-methoxybenzo[d]oxazol-2-yl)benzylamine |
| Synthesis Example 13 | nicotinic acid | cyclohexyl 4-aminobenzoate |
| Synthesis Example 14 | nicotinic acid | 4-(5-isopropylbenzo[d]oxazol-2-yl)aniline |
| Synthesis Example 15 | nicotinic acid | (4-aminophenyl)(benzofuran-2-yl)methanone |
| Synthesis Example 16 | nicotinic acid | 4-(3-ethyl-[1,2,4]triazolo[3,4-b][1,3,4]thiadiazol-6-yl)aniline |

TABLE 1-continued

| Synthesis Example | acid | Amine |
|---|---|---|
| Synthesis Example 17 | nicotinic acid | 4-([1,2,4]triazolo[3,4-b][1,3,4]thiadiazol-6-yl)aniline |
| Synthesis Example 18 | imidazo[1,2-a]pyridine-6-carboxylic acid | methyl 4-(2-aminoethyl)benzoate |
| Synthesis Example 19 | nicotinic acid | 2-(3,4-dimethylphenyl)-1,3-benzoxazol-5-amine |
| Synthesis Example 20 | nicotinic acid | N-(2-aminoethyl)-3-(4-chlorophenyl)-1,2,4-oxadiazole-5-carboxamide |
| Synthesis Example 21 | nicotinic acid | N-(2-aminoethyl)-3-(4-methylphenyl)-1,2,4-oxadiazole-5-carboxamide |
| Synthesis Example 22 | nicotinic acid | N-(2-aminoethyl)-3-(thiophen-2-yl)-1,2,4-oxadiazole-5-carboxamide |
| Synthesis Example 23 | nicotinic acid | N-(2-aminoethyl)-3-(4-methoxyphenyl)-1,2,4-oxadiazole-5-carboxamide |
| Synthesis Example 24 | nicotinic acid | N-(2-aminoethyl)quinoline-2-carboxamide |

TABLE 1-continued

| Synthesis Example | acid | Amine |
| --- | --- | --- |
| Synthesis Example 25 | nicotinic acid | H₂N-CH₂CH₂-NH-C(=O)-benzothiazol-2-yl |
| Synthesis Example 26 | isonicotinic acid | 7-amino-2-[(E)-3-(pyridin-3-yl)acryloyl]-1,2,3,4-tetrahydroisoquinoline |
| Synthesis Example 27 | nicotinic acid | 4-(2-methyl-1H-imidazol-1-yl)benzylamine |
| Synthesis Example 28 | nicotinic acid | 4-(morpholin-4-ylsulfonyl)benzylamine |
| Synthesis Example 29 | nicotinic acid | 4-(piperidin-1-yl)benzylamine |
| Synthesis Example 30 | nicotinic acid | 4-(pyridin-2-ylmethoxy)benzylamine |
| Synthesis Example 31 | nicotinic acid | 4-(piperidin-1-ylsulfonyl)benzylamine |
| Synthesis Example 32 | nicotinic acid | 4-[(diethylammonio)methyl]benzylamine |

TABLE 2

| Synthesis Example | Compound name | Final Compound |
|---|---|---|
| Synthesis Example 5 | B1380 | 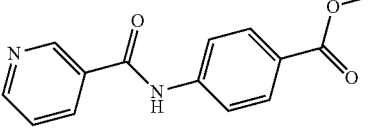<br>methyl 4-(nicotinamido)benzoate |
| Synthesis Example 6 | B1416 | 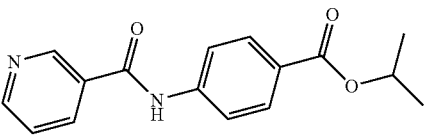<br>isopropyl 4-(nicotinamido)benzoate |
| Synthesis Example 7 | B1423 | 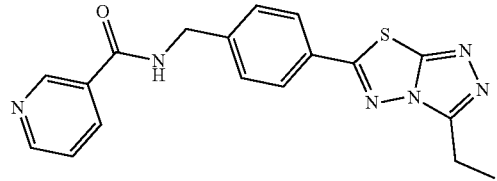<br>N-(4-(3-ethyl-[1,2,4]triazolo[3,4-b][1,3,4]thiadiazol-6-yl)benzyl)nicotinamide |
| Synthesis Example 8 | B1468 | 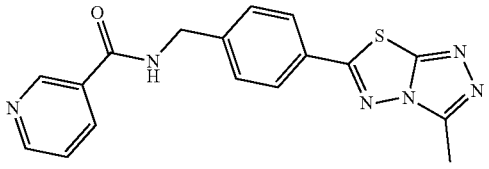<br>N-(4-(3-methyl-[1,2,4]triazolo[3,4-b][1,3,4]thiadiazol-6-yl)benzyl)nicotinamide |
| Synthesis Example 9 | B1469 | 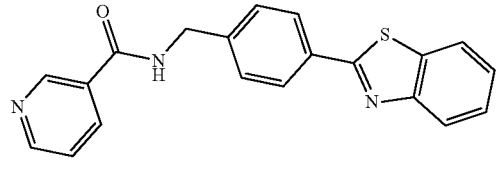<br>N-(4-(benzo[d]thiazol-2-yl)benzyl)nicotinamide |
| Synthesis Example 10 | B1470 | 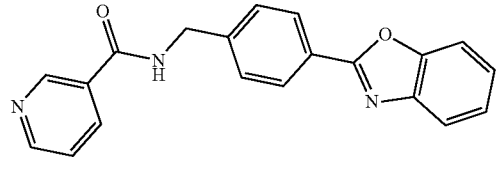<br>N-(4-(benzo[d]oxazol-2-yl)benzyl)nicotinamide |

TABLE 2-continued

| Synthesis Example | Compound name | Final Compound |
|---|---|---|
| Synthesis Example 11 | B1472 | 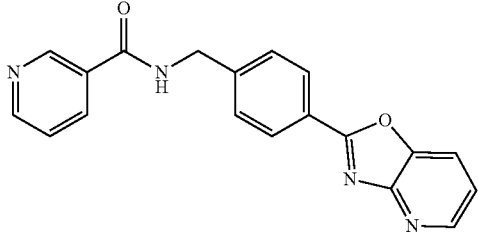<br>N-(4-oxazolo[4,5-b]pyridin-2-yl) benzyl)nicotinamide |
| Synthesis Example 12 | B1474 | 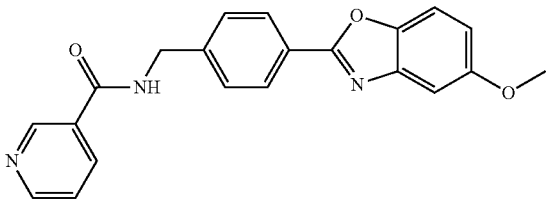<br>N-(4-(5-methoxybenzo[d]oxazol-2-yl)benzyl)nicotinamide |
| Synthesis Example 13 | B1477 | 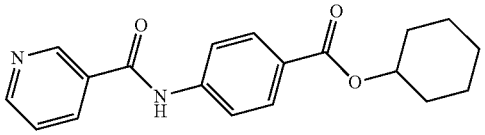<br>cyclohexyl 4-(nicotinamido)benzoate |
| Synthesis Example 14 | B1479 | 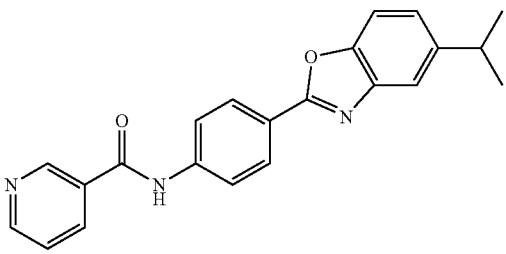<br>N-(4-(5-isopropylbenzo[d]oxazol-2-yl) phenyl)nicotinamide |
| Synthesis Example 15 | B1484 | 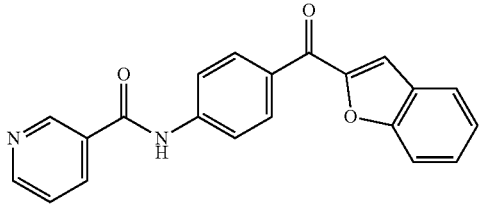<br>N-(4-(benzofuran-2-carbonyl)phenyl)nicotinamide |

TABLE 2-continued

| Synthesis Example | Compound name | Final Compound |
|---|---|---|
| Synthesis Example 16 | B1485 | 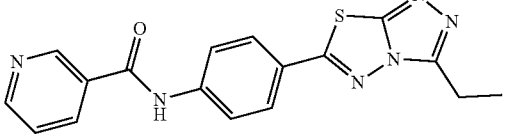<br>N-(4-(3-ethyl-[1,2,4]triazolo[3,4-b][1,3,4]thiadiazol-6-yl)phenyl)nicotinamide |
| Synthesis Example 17 | B1523 | 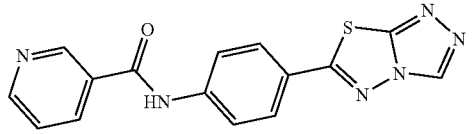<br>N-(4-([1,2,4]triazolo[3,4-b]thiadiazol-6-yl)phenyl)nicotinamide |
| Synthesis Example 18 | B1531 | 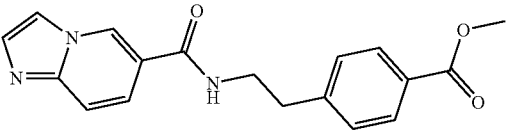<br>methyl 4-(2-(imidazo[1,2-a]pyridine-6-carboxamido)ethyl)benzoate |
| Synthesis Example 19 | B1716 | 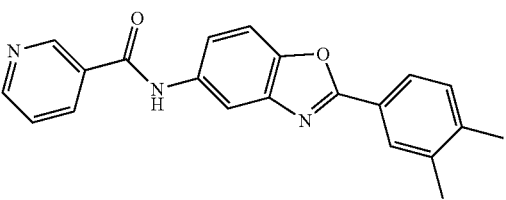<br>N-(2-(3,4-dimethylphenyl)benzo[d]oxazol-5-yl)nicotinamide |
| Synthesis Example 20 | B1856 | 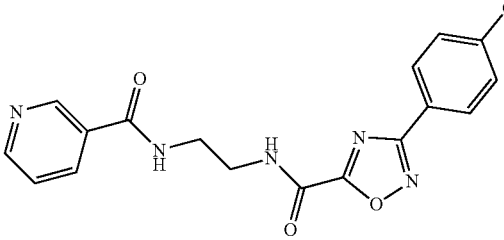<br>3-(4-chlorophenyl)-N-(2-(nicotinamido)ethyl)-1,2,4-oxadiazole-5-carboxamide |

TABLE 2-continued

| Synthesis Example | Compound name | Final Compound |
|---|---|---|
| Synthesis Example 21 | B1857 | 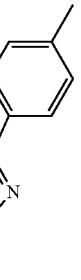<br>N-(2-(nicotinamido)ethyl)-3-(p-tolyl)-1,2,4-oxadiazole-5-carboxamide |
| Synthesis Example 22 | B1863 | 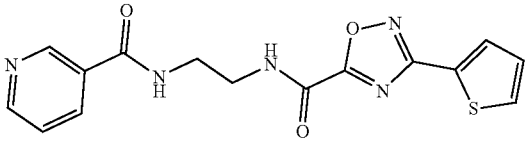<br>N-(2-(nicotinamido)ethyl)-3-(thiophen-2-yl)-1,2,4-oxadiazole-5-carboxamide |
| Synthesis Example 23 | B1866 | 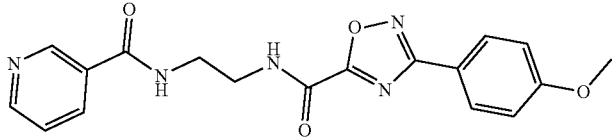<br>3-(4-methoxyphenyl)-N-(2-(nicotinamido)ethyl)-1,2,4-oxadiazole-5-carboxamide |
| Synthesis Example 24 | B1872 | 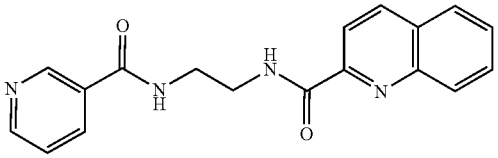<br>N-(2-(nicotinamido)ethyl)quinoline-2-carboxamide |
| Synthesis Example 25 | B1873 | 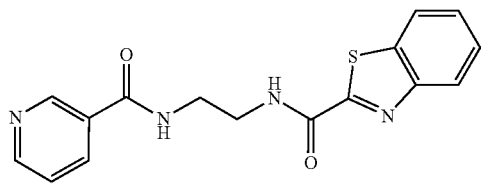<br>N-(2-(nicotinamido)ethyl)benzo[d]thiazole-2-carboxamide |
| Synthesis Example 26 | B1963 | 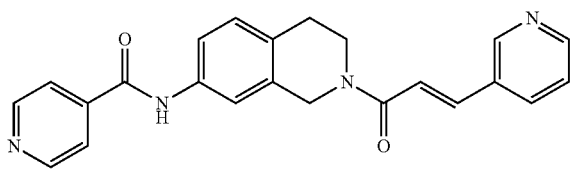<br>(E)-N-(2-(3-(pyridin-3-yl)acryloyl)-1,2,3,4-tetrahydroisoquinolin-7-yl)isonicotinamide |

TABLE 2-continued

| Synthesis Example | Compound name | Final Compound |
|---|---|---|
| Synthesis Example 27 | B1967 | 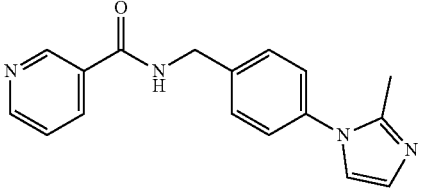<br>N-(4-(2-methyl-1H-imidazol-1-yl)benzyl)nicotinamide |
| Synthesis Example 28 | B1977 | 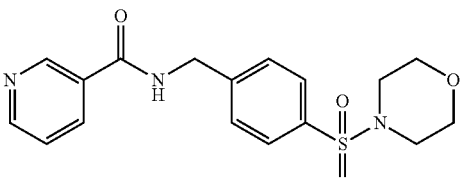<br>N-(4-(morpholinosulfonyl)benzyl)nicotinamide |
| Synthesis Example 29 | B1978 | 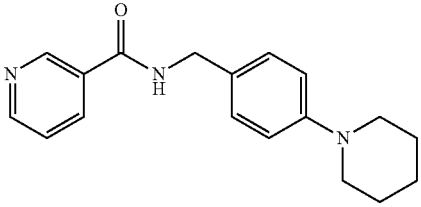<br>N-(4-(piperidin-1-yl)benzyl)nicotinamide |
| Synthesis Example 30 | B1979 | 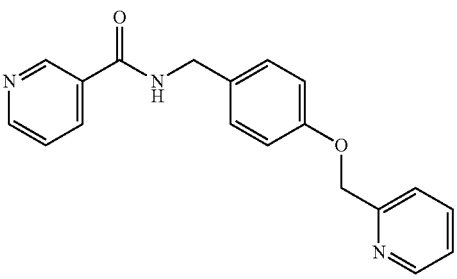<br>N-(4-(pyridin-2-ylmethoxy)benzyl)nicotinamide |
| Synthesis Example 31 | B1981 | 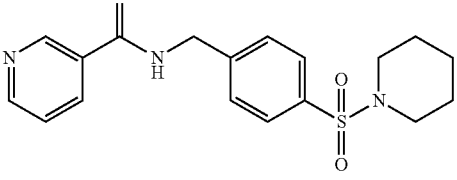<br>N-(4-(piperidin-1-ylsulfonyl)benzyl)nicotinamide |
| Synthesis Example 32 | B1982 | 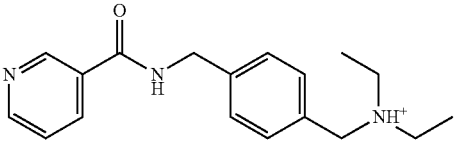<br>N-ethyl-N-(4-nicotinamidomethyl)benzyl)ethanaminium |

[Synthesis Example 33] Preparation of N-(4-(5-ethylbenzo[d]oxazol-2-yl)benzyl)nicotinamide

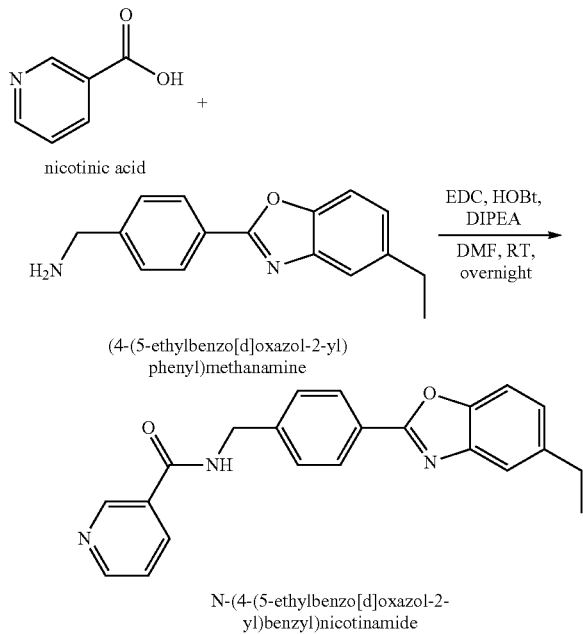

Figure 5:
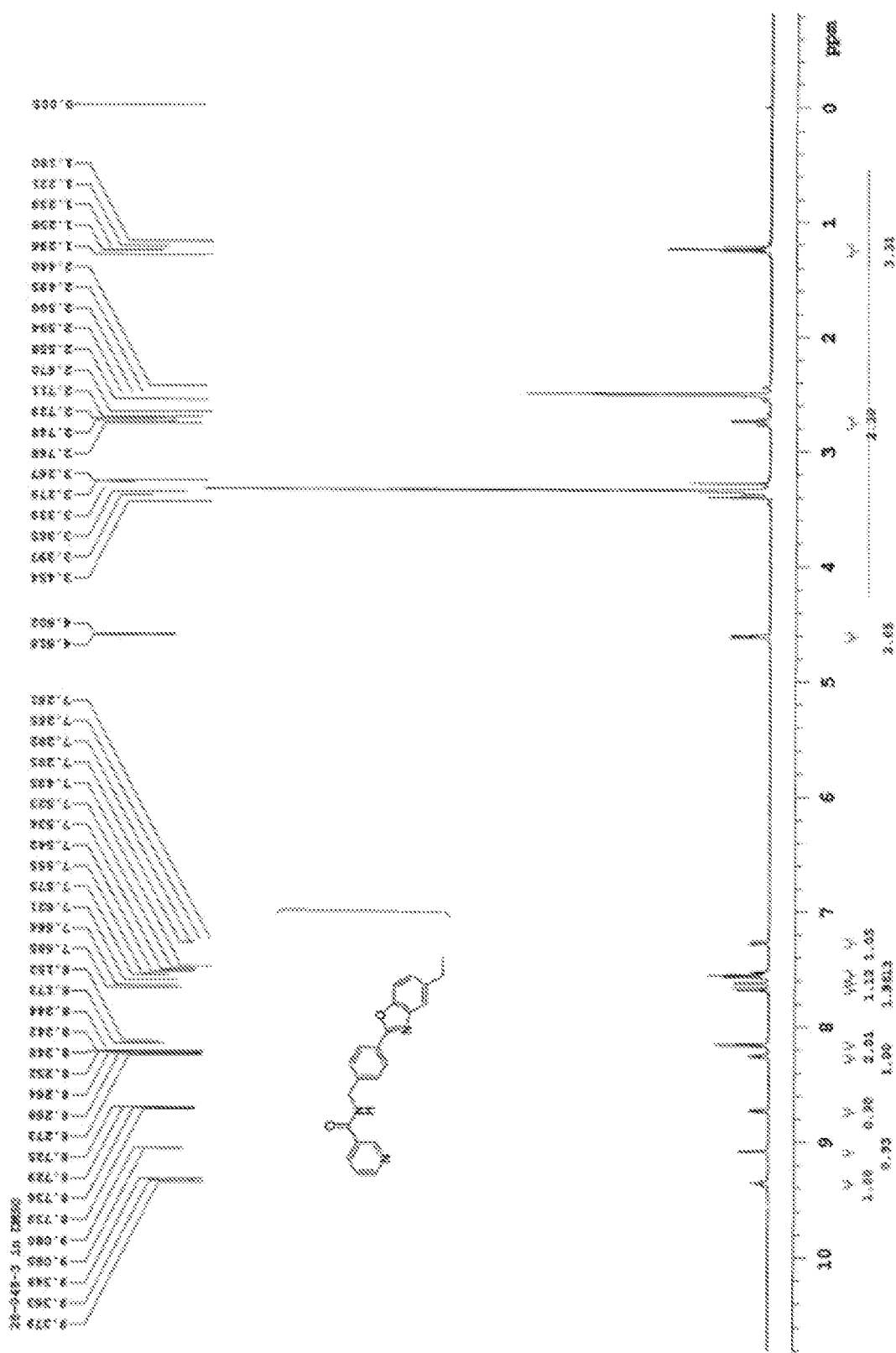
FIG. 5 shows NMR spectrum of N-ethyl-N-(4-(nicotinamidomethyl) benzyl) ethanaminium (Drug 3) prepared in Synthesis Example 33 according to an example of the present invention.
Figure 6:
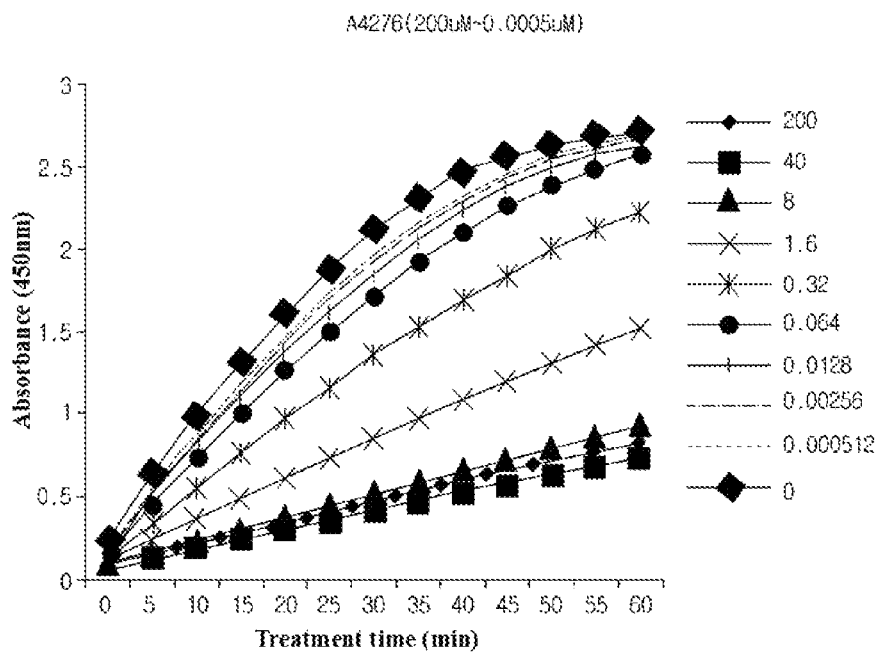
FIG. 6 shows the results measuring the change of absorbance according to the treatment time when the compound (A4276) prepared in Synthesis Example 1 was treated at various concentrations according to an example of the present invention for NamPT in Evaluation Example 1.
Figure 7:
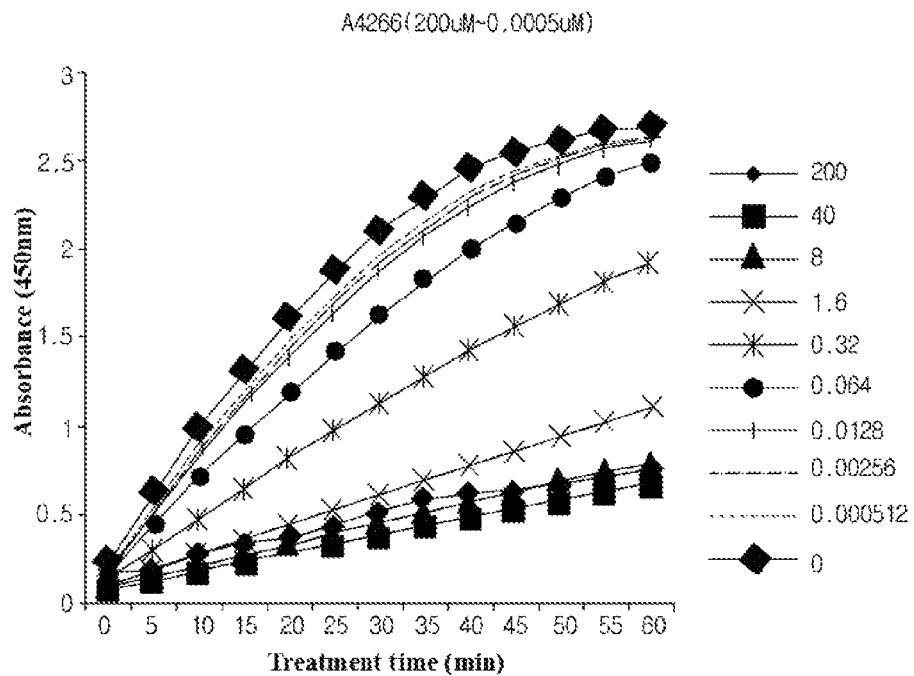
FIG. 7 shows the results measuring the change of absorbance according to the treatment time when the compound (A4266) prepared in Synthesis Example 2 was treated at various concentrations according to an example of the present invention for NamPT in Evaluation Example 1.
Figure 8:
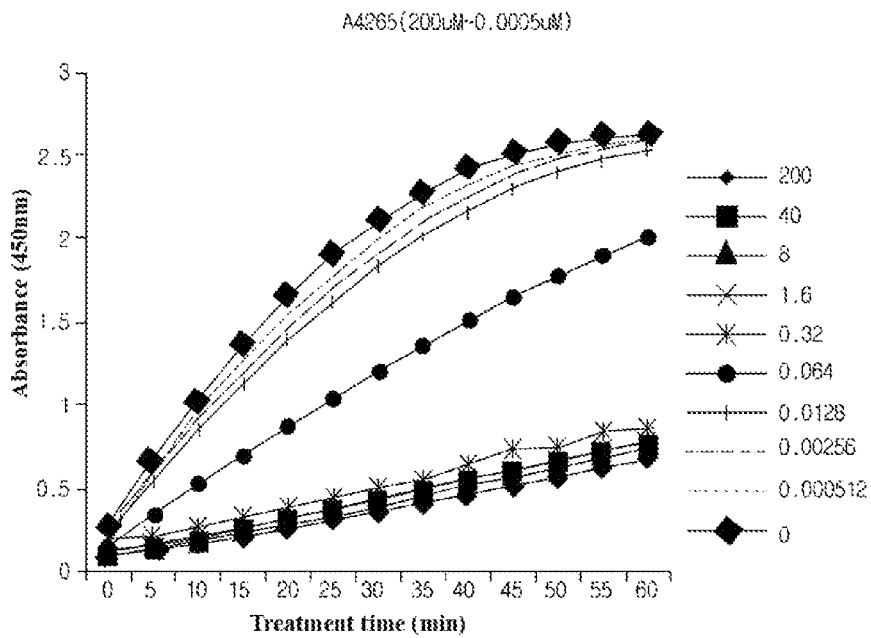
FIG. 8 shows the results measuring the change of absorbance according to the treatment time when the compound (A4265) prepared in Synthesis Example 3 was treated at various concentrations according to an example of the present invention for NamPT in Evaluation Example 1.
Figure 9:
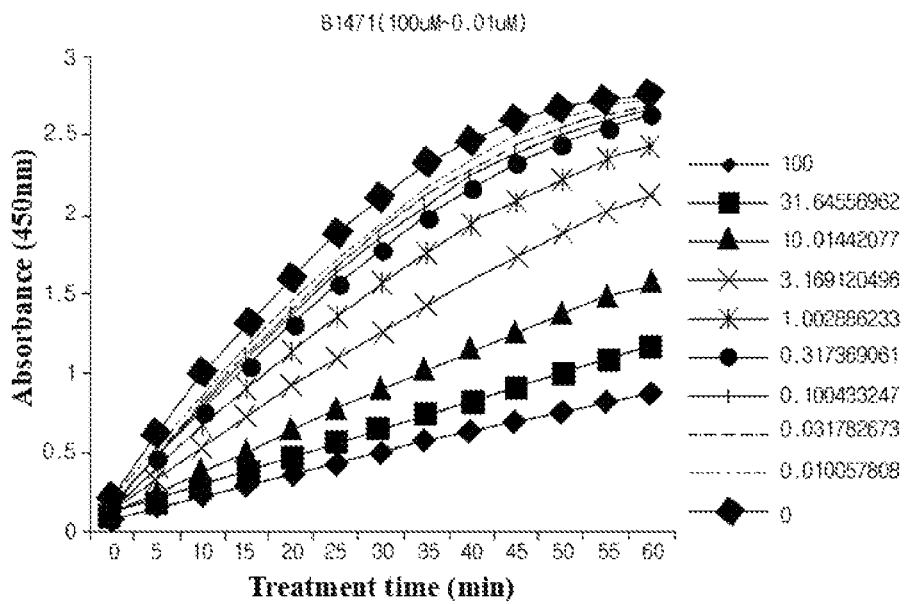
FIG. 9 shows the results measuring the change of absorbance according to the treatment time when the compound (B1471) prepared in Synthesis Example 4 was treated at various concentrations according to an example of the present invention for NamPT in Evaluation Example 1.
Figure 10:
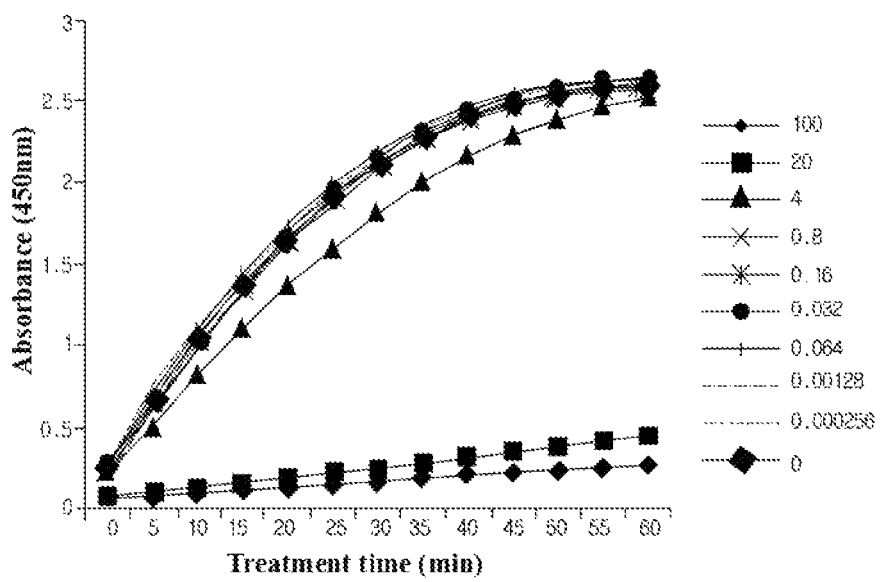
FIG. 10 shows the results measuring the change of absorbance according to the treatment time when the compound (FK866) prepared in Comparative Example 1 was treated at various concentrations according to an example of the present invention for NamPT in Evaluation Example 1.
Figure 11:
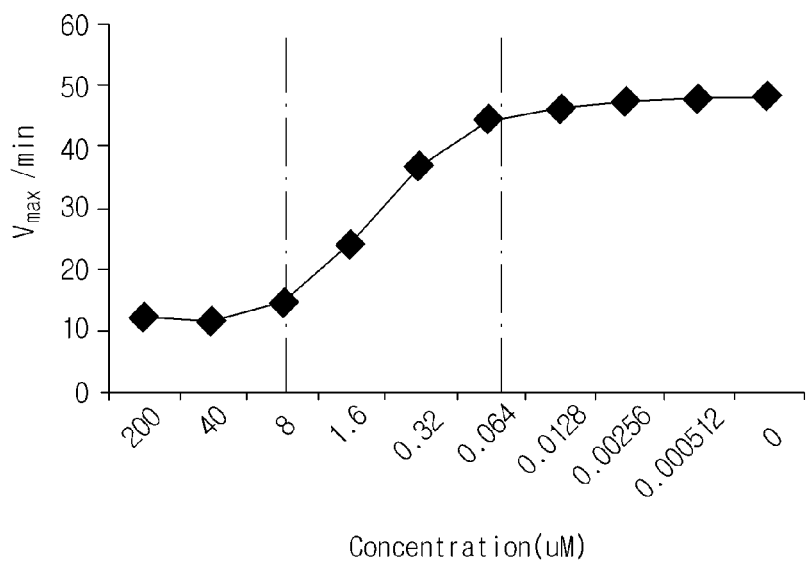
FIG. 11 is a graph showing the change in Vmax/min according to the treatment concentration of the A4276 compound according to the results of FIG. 6 in Evaluation Example 1.
Figure 12:
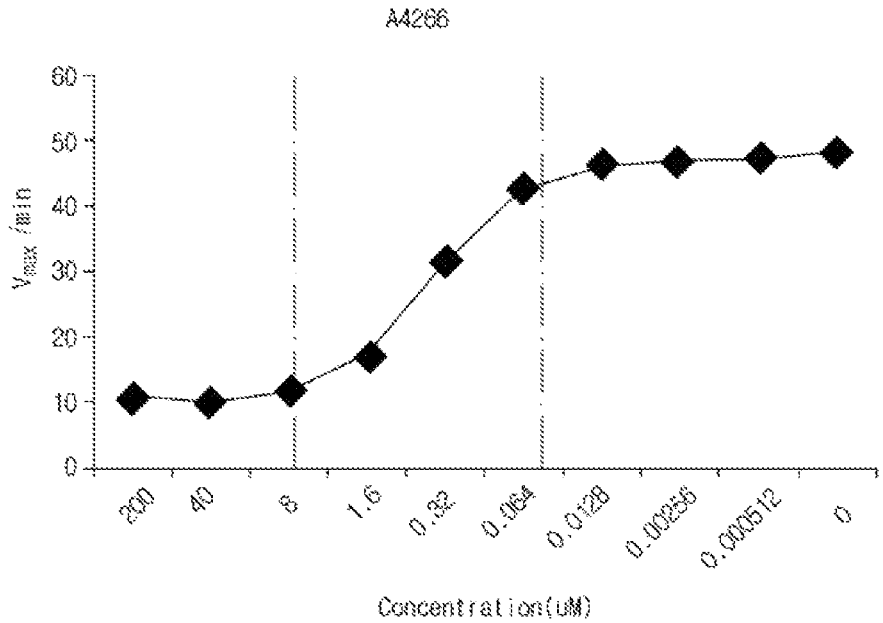
FIG. 12 is a graph showing the change in Vmax/min according to the treatment concentration of the A4266 compound according to the results of FIG. 7 in Evaluation Example 1.
Figure 13:
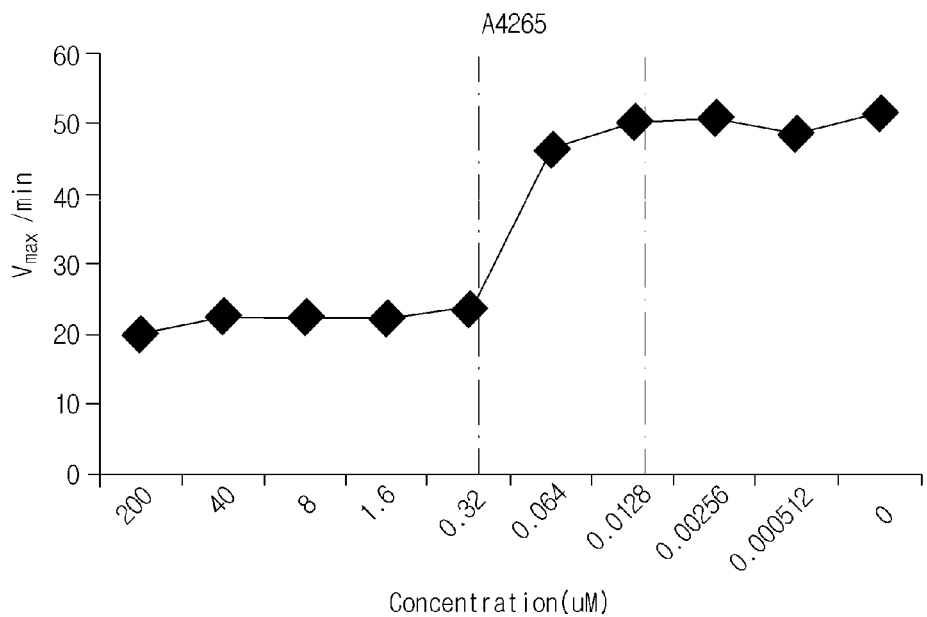
FIG. 13 is a graph showing the change in Vmax/min according to the treatment concentration of the A4265 compound according to the results of FIG. 8 in Evaluation Example 1.
Figure 14:
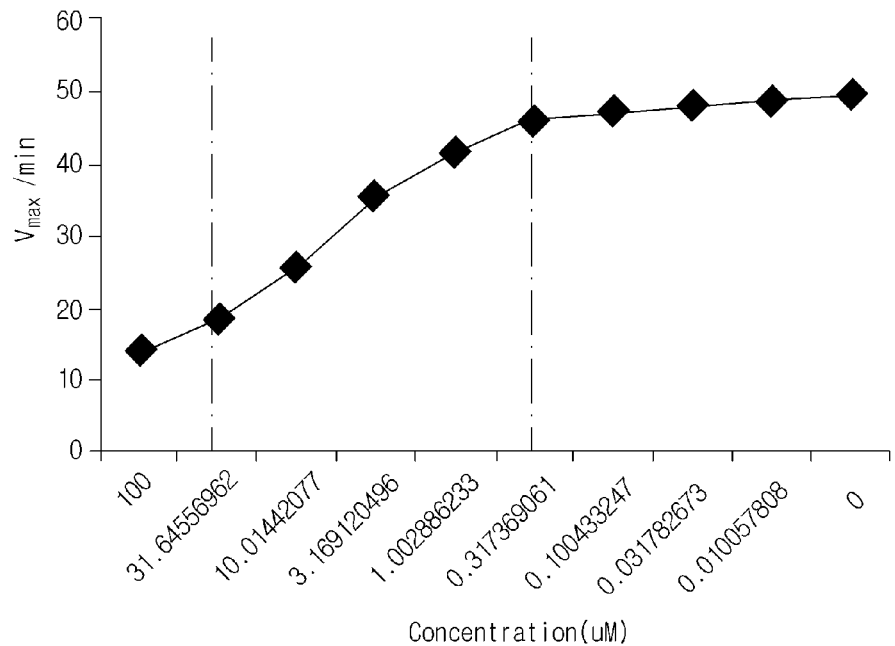
FIG. 14 is a graph showing the change in Vmax/min according to the treatment concentration of the A1471 compound according to the results of FIG. 9 in Evaluation Example 1.
Figure 15:
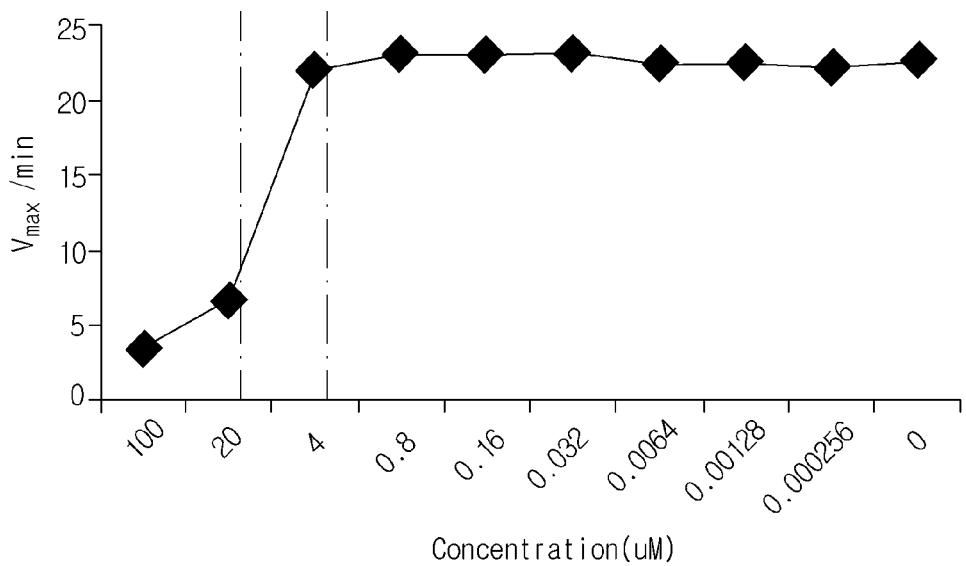
FIG. 15 is a graph showing the change in Vmax/min according to the treatment concentration of the FK866 compound according to the results of FIG. 10 in Evaluation Example 1.
Figure 16:
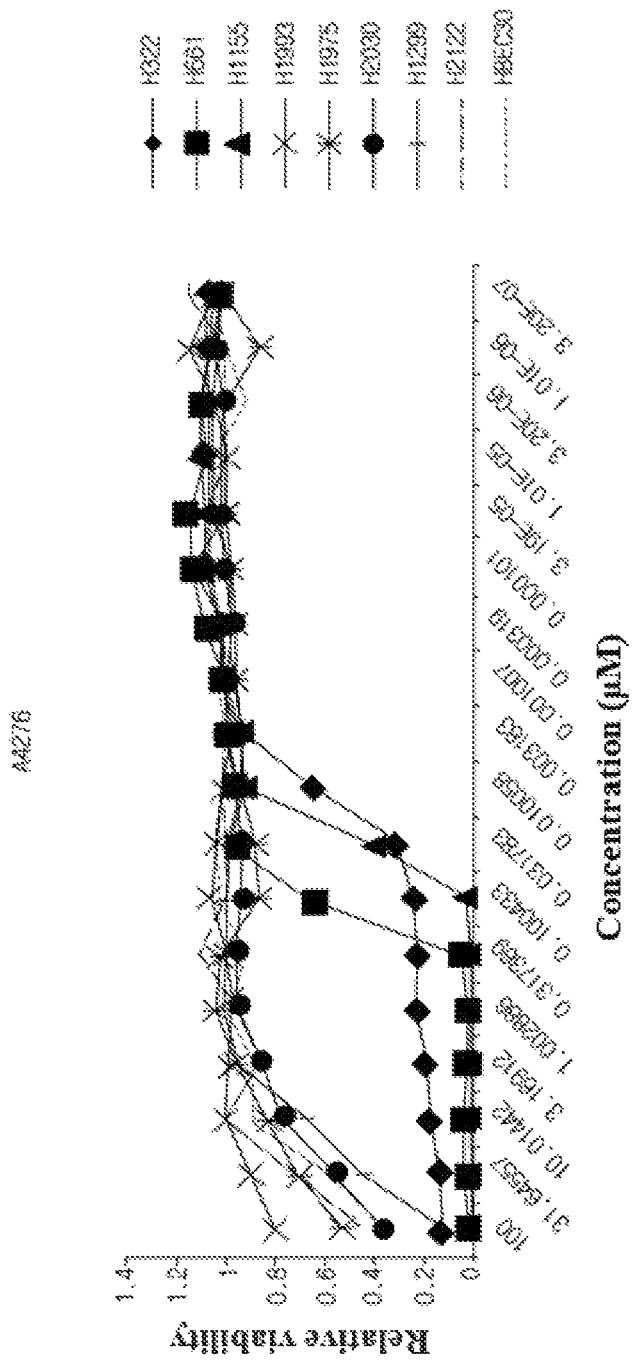
FIG. 16 shows the result of measuring the change in the viability of the cancer cell line according to concentration after treating the compound (A4276) prepared in Synthesis Example 1 at various concentrations according to an example of the present invention for various cancer cell lines in Evaluation Example 2.
Figure 17:
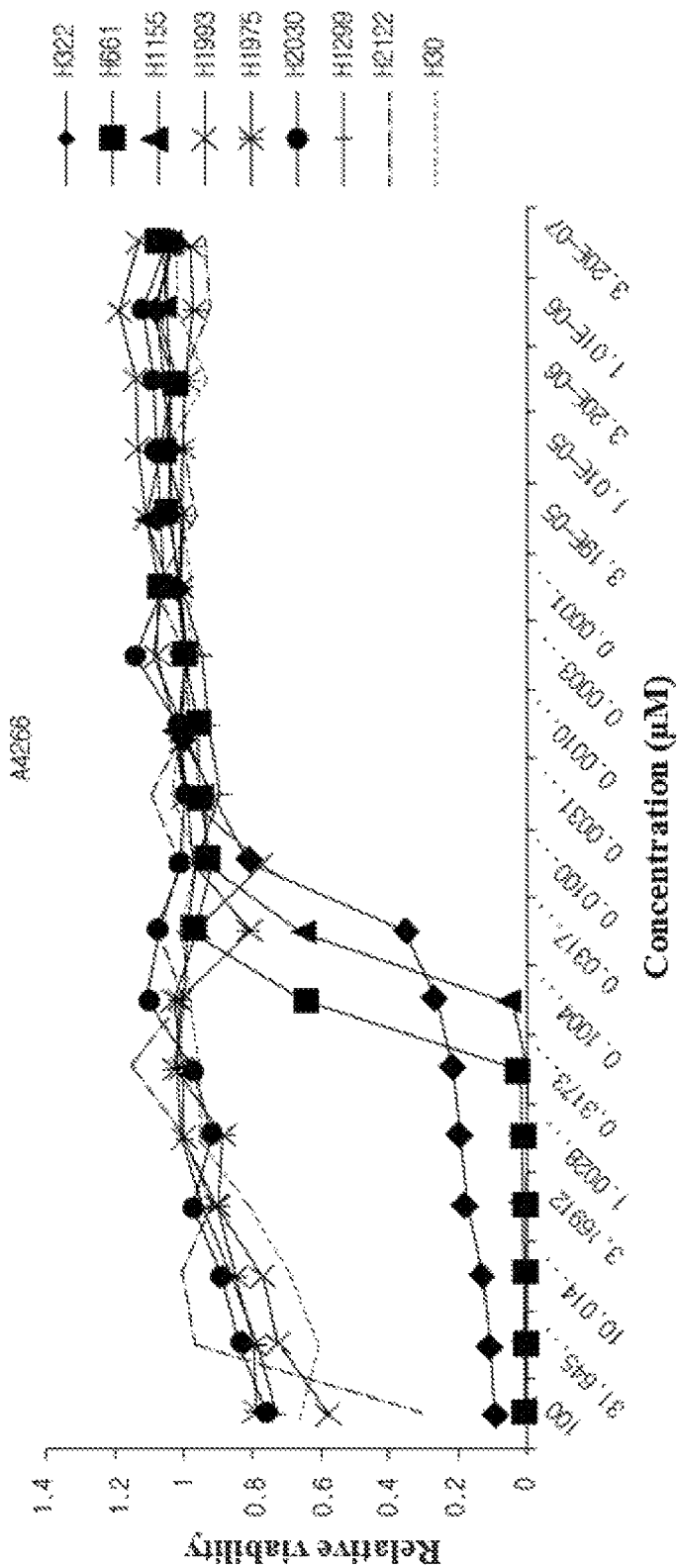
FIG. 17 shows the result of measuring the change in the viability of the cancer cell line according to concentration after treating the compound (A4266) prepared in Synthesis Example 2 at various concentrations according to an example of the present invention for various cancer cell lines in Evaluation Example 2.
Figure 18:
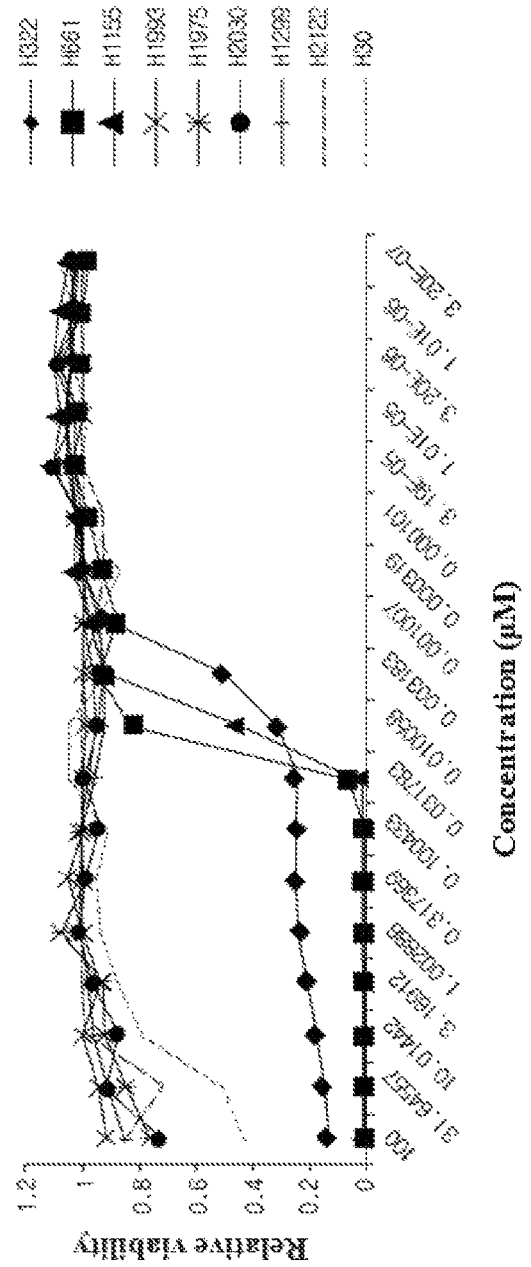
FIG. 18 shows the result of measuring the change in the viability of the cancer cell line according to concentration after treating the compound (A4265) prepared in Synthesis Example 3 at various concentrations according to an example of the present invention for various cancer cell lines in Evaluation Example 2.
Figure 19:
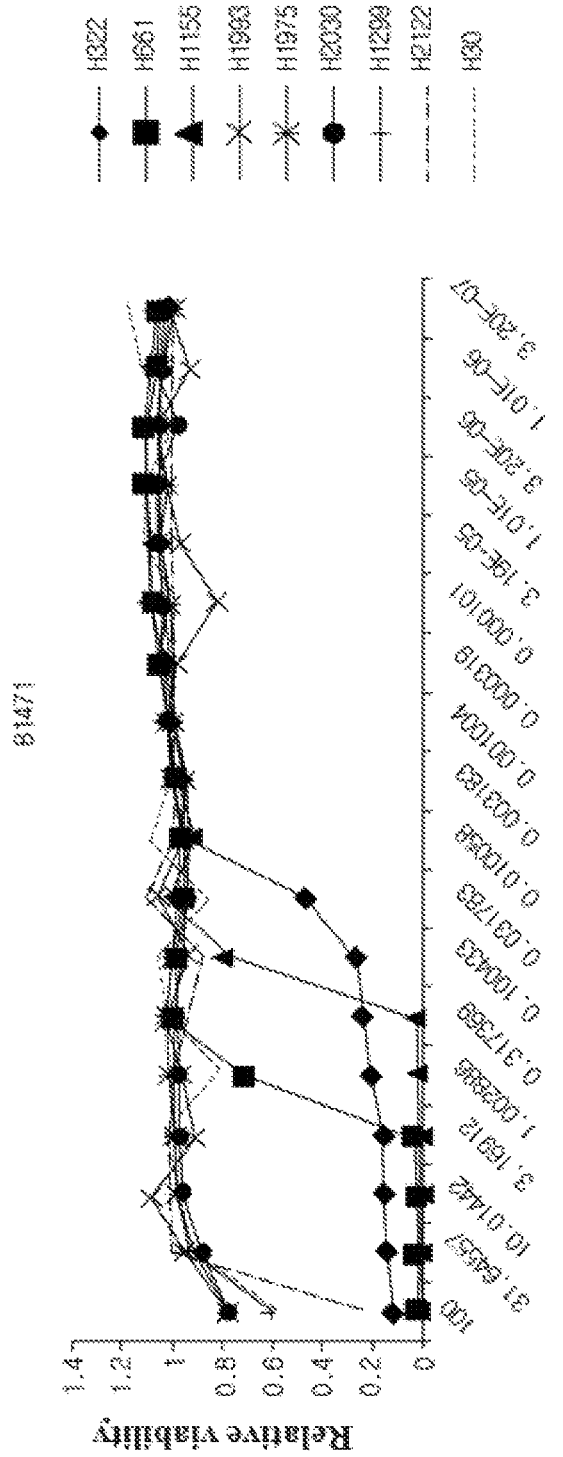
FIG. 19 shows the result of measuring the change in the viability of the cancer cell line according to concentration after treating the compound (B1471) prepared in Synthesis Example 4 at various concentrations according to an example of the present invention for various cancer cell lines in Evaluation Example 2.

Nicotinic acid (2.44 mmol), (4-(5-ethylbenzo[d]oxazol-2-yl)phenyl)methanamine (2.44 mmol), EDC (1-(3-dimethylaminopropyl)-3-ethylcarbodiimide hydrochloride, 4.87 mmol), HOBt (1-hydroxybenzotriazole monohydrate, 4.87 mmol) and DIPEA (N,N-diisopropylethylamine, 7.31 mmol) were dissolved in DMF (dimethylformamide, 10 ml) and refluxed overnight at room temperature. Thereafter, the reaction mixture was transferred to a separate funnel, followed by the addition of an aqueous solution of $NH_4Cl$ and three extractions with EA (ethyl acetate). The extract was dried with $Na_2SO_4$ and concentrated under reduced pressure. The reaction residue was purified by flash column chromatography (5% methanol in dichloromethane) and then dried in a vacuum pump to prepare a final compound (hereinafter referred to as "Drug 3"). NMR spectrum of N-(4-(5-ethylbenzo[d]oxazol-2-yl)benzyl)nicotinamide prepared as described above is shown in FIG. 5.

Synthesis Example 34 to 39

According to the above Reaction Scheme 3, acid (2.44 mmol) and amine (2.44 mmol) of the following Table 3, EDC (1-(3-dimethylaminopropyl)-3-ethylcarbodiimide hydrochloride, 4.87 mmol), HOBt (1-Hydroxybenzotriazole monohydrate, 4.87 mmol) and DIPEA (N,N-diisopropylethylamine, 7.31 mmol) were dissolved in DMF (dimethylformamide, 10 ml) and refluxed overnight at room temperature. Thereafter, the reaction mixture was transferred to a separate funnel, followed by the addition of an aqueous solution of $NH_4Cl$ and three extractions with EA (ethyl acetate). The extract was dried with $Na_2SO_4$ and concentrated under reduced pressure. The reaction residue was purified by flash column chromatography (5% methanol in dichloromethane) and dried in a vacuum pump to produce the final compound shown in Table 4 below.

TABLE 3

| Synthesis Example | Acid | Amine |
|---|---|---|
| Synthesis Example 34 | nicotinic acid | 4-(6-nitrobenzo[d]oxazol-2-yl)phenyl)methanamine |
| Synthesis Example 35 | nicotinic acid | (4-(5-phenylbenzo[d]oxazol-2-yl)phenyl)methanamine |
| Synthesis Example 36 | nicotinic acid | (4-(6-tert-butylbenzo[d]oxazol-2-yl)phenyl)methanamine |
| Synthesis Example 37 | nicotinic acid | (4-(5-methylbenzo[d]oxazol-2-yl)phenyl)methanamine |

TABLE 3-continued

| Synthesis Example | Acid | Amine |
|---|---|---|
| Synthesis Example 38 | nicotinic acid | 4-(6-ethylbenzo[d]oxazol-2-yl)benzylamine |
| Synthesis Example 39 | benzoic acid | 4-(6-methylbenzo[d]oxazol-2-yl)benzylamine |

TABLE 4

| Synthesis Example | Compound name | Final Compound | $^1$H NMR spectrum (400 MHz, DMSO-d6): |
|---|---|---|---|
| Synthesis Example 34 | A4261 | N-(4-(6-nitrobenzo[d]oxazol-2-yl)benzyl)nicotinamide | δ 9.35 (t, J = 5.3 Hz, 1H), 9.05 (s, 1H), 8.70 (d, J = 1.5 Hz, 2H), 8.29 (d, J = 8.7 Hz, 1H), 8.25-8.17 (m, 3H), 7.97 (d, J = 8.8 Hz, 1H), 7.58 (d, J = 7.9 Hz, 2H), 7.50 (dd, J = 7.2, 5.0 Hz, 1H), 4.60 (d, J = 5.4 Hz, 2H) |
| Synthesis Example 35 | A4262 | N-(4-(5-phenylbenzo[d]oxazol-2-yl)benzyl)nicotinamide | δ 9.33 (t, J = 5.5 Hz, 1H), 9.06 (s, 1H), 8.70 (d, J = 3.3 Hz, 1H), 8.23 (d, J = 7.9 Hz, 1H), 8.17 (d, J = 8.1 Hz, 2H), 8.02 (s, 1H), 7.82 (d, J = 8.5 Hz, 1H), 7.73-7.64 (m, 3H), 7.55 (d, J = 8.0 Hz, 2H), 7.53-7.41 (m, 3H), 7.35 (t, J = 7.3 Hz, 1H), 4.59 (d, J = 5.5 Hz, 2H) |
| Synthesis Example 36 | A4263 | N-(4-(6-(tert-butyl)benzo[d]oxazol-2-yl)benzyl)nicotinamide | δ 9.32 (t, J = 5.3 Hz, 1H), 9.05 (s, 1H), 8.70 (d, J = 3.4 Hz, 1H), 8.23 (d, J = 7.9 Hz, 1H), 8.12 (d, J = 8.0 Hz, 2H), 7.74 (s, 1H), 7.66 (d, J = 8.4 Hz, 1H), 7.51 (dd, J = 15.4, 7.9 Hz, 3H), 7.43 (d, J = 8.2 Hz, 1H), 4.57 |

TABLE 4-continued

| Synthesis Example | Compound name | Final Compound | ¹H NMR spectrum (400 MHz, DMSO-d6): |
|---|---|---|---|
| | | | (d, J = 5.5 Hz, 2H), 1.32 (s, 9H) |
| Synthesis Example 37 | A4275 | N-(4-(5-methylbenzo[d]oxazol-2-yl)benzyl)nicotinamide | δ 9.36 (t, J = 5.5 Hz, 1H), 9.09 (s, 1H), 8.76-8.73 (m, 1H), 8.27 (d, J = 7.9 Hz, 1H), 8.17 (d, J = 8.1 Hz, 2H), 7.65 (d, J = 8.3 Hz, 1H), 7.61-7.51 (m, 4H), 7.24 (d, J = 8.2 Hz, 1H), 4.62 (d, J = 5.6 Hz, 2H), 2.45 (s, 3H) |
| Synthesis Example 38 | A4302 | N-(4-(6-ethylbenzo[d]oxazol-2-yl)benzyl)nicotinamide | δ 9.36-9.28 (s, 1H), 9.05 (s, 1H), 8.70 (s, 1H), 8.23 (d, J = 7.9 Hz, 1H), 8.12 (d, J = 7.8 Hz, 2H), 7.65 (d, J = 8.0 Hz, 1H), 7.59 (s, 1H), 7.56-7.48 (m, 3H), 7.22 (d, J = 8.1 Hz, 1H), 4.57 (d, J = 5.0 Hz, 2H), 2.72 (q, J = 7.4 Hz, 2H), 1.21 (t, J = 7.4 Hz, 3H) |
| Synthesis Example 39 | A4303 | N-(4-(6-(methylbenzobenzo[d]oxazol-2-yl)benzyl)benzamide | δ 9.13 (t, J = 5.5 Hz, 1H), 8.11 (d, J = 8.0 Hz, 2H), 7.89 (d, J = 7.4 Hz, 2H), 7.62 (d, J = 8.1 Hz, 1H), 7.58-7.42 (m, 5H), 7.19 (d, J = 8.0 Hz, 1H), 4.55 (d, J = 5.7 Hz, 2H), 2.43 (s, 2H) |

Synthesis Example 40 to 43

[Reaction Scheme 4]

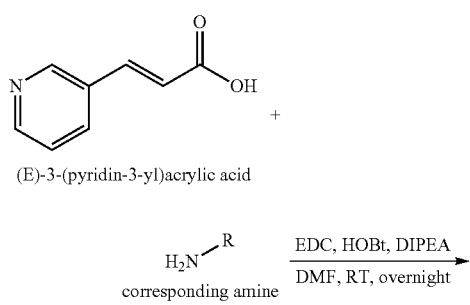

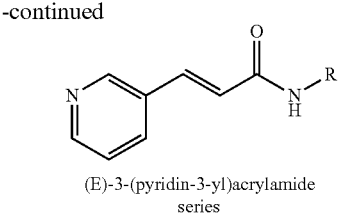

(E)-3-(pyridin-3-yl)acrylamide series

According to the Reaction Scheme 4, (E)-3-(pyridin-3-yl)acrylic acid (2.44 mmol), amine (2.44 mmol) of the following Table 5, EDC (1-(3-dimethylaminopropyl)-3-ethylcarbodiimide hydrochloride, 4.87 mmol), HOBt (1-hydroxybenzotriazole monohydrate, 4.87 mmol) and DIPEA (N,N-diisopropylethylamine, 7.31 mmol) were dissolved in DMF (dimethylformamide, 10 ml) and refluxed overnight at room temperature. Thereafter, the reaction mixture was transferred to a separate funnel, followed by the addition of an aqueous solution of NH₄Cl and three extractions with EA (ethyl acetate). The extract was dried with Na₂SO₄ and concentrated under reduced pressure. The reaction residue was purified by flash column chromatography (5% methanol in dichloromethane) and then dried in a vacuum pump to prepare the final compound shown in Table 6 below.

TABLE 5

| Synthesis Example | Amine |
|---|---|
| Synthesis Example 40 | 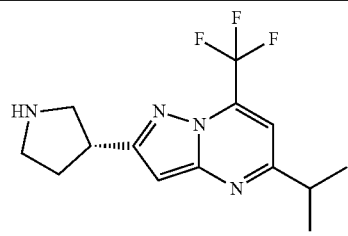 |
| Synthesis Example 41 | 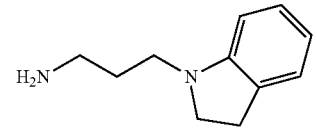 [SMILES: NCCCN1CCc2ccccc21] |

TABLE 5-continued

| Synthesis Example | Amine |
|---|---|
| Synthesis Example 42 | 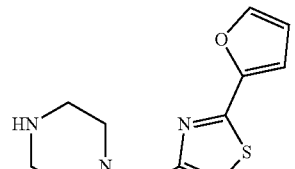 |
| Synthesis Example 43 | 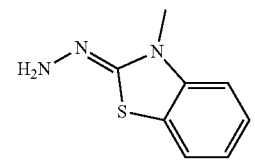 |

TABLE 6

| Synthesis Example | Compound name | Final Compound |
|---|---|---|
| Synthesis Example 40 | B1964 | 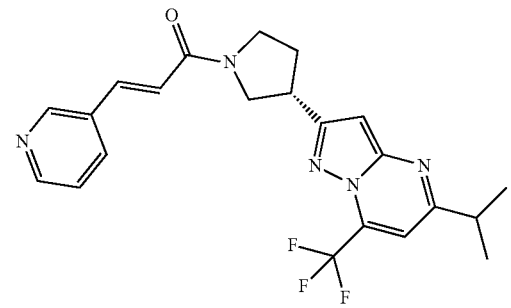<br>(S,E)-1-(3-(5-isopropyl-7-(trifluoromethyl)pyrazolo[1,5-a]pyrimidin-2-yl)pyrrolidin-1-yl)-3-(pyridin-3-yl)prop-2-en-1-one |
| Synthesis Example 41 | B1975 | 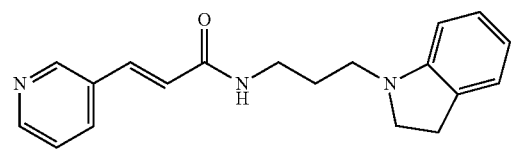<br>(E)-N-(3-(indolin-1-yl)propyl)-3-(pyridin-3-yl)acrylamide |

TABLE 6-continued

| Synthesis Example | Compound name | Final Compound |
|---|---|---|
| Synthesis Example 42 | B1976 | 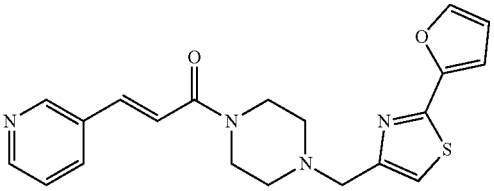<br>(E)-1-(4-((2-(furan-2-yl)thiazol-4-yl)methyl)piperazin-1-yl)-3-(pyridin-3-yl)prop-2-en-1-one |
| Synthesis Example 43 | B1983 | 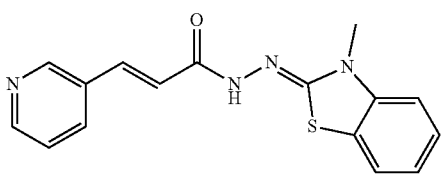<br>(2E,N'Z)-N'-(3-methylbenzo[d]thiazol-2(3H)-ylidene)-3-(pyridin-3-yl)acrylohydrazide |

[Synthesis Example 44] Preparation of B1386

N-methyl isonicotinamide and 4-(iminomethyl)benzene-1,3-diol represented by the following Chemical Formulae were mixed at a weight ratio of 1:1.

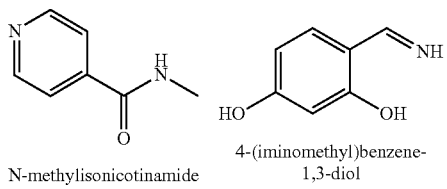

[Synthesis Example 45] Preparation of B1387

N-methyl isonicotinamide and 4-chloro-2-(iminomethyl) phenol represented by the following Chemical Formulae were mixed at a weight ratio of 1:1.

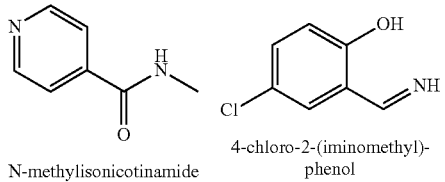

[Synthesis Example 46] Preparation of B1467

N,4-dimethylbenzamide and 4-(iminomethyl)benzene-1,3-diol represented by the following Chemical Formulae were mixed at a weight ratio of 1:1.

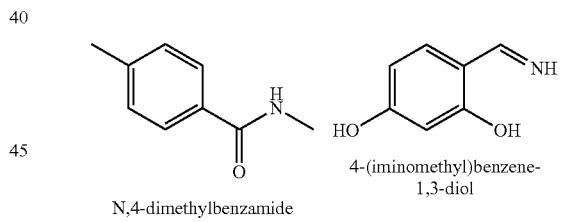

[Comparative Example 1] Preparation of N-[4-(1-benzoyl-4-piperidinyl) butyl]-3-(3-pyridinyl)-2E-propenamide

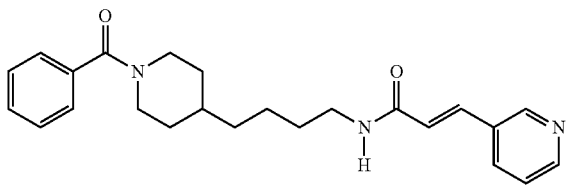 [SMILES: O=C(/C=C/c1cccnc1)NCCCCC1CCN(C(=O)c2ccccc2)CC1]

For comparison of the following effects with the compounds of the present invention, N-[4-(1-benzoyl-4-piperidinyl) butyl]-3-(3-pyridinyl)-2E-propenamide (hereinafter referred to as "FK866") which is represented by the above Chemical Formula and known as the NamPT inhibitor was prepared.

[Comparative Example 2] Preparation of N-(4-((3,5-difluorophenyl)sulfonyl)benzyl)imidazo[1,2-a]pyridine-6-carboxamide

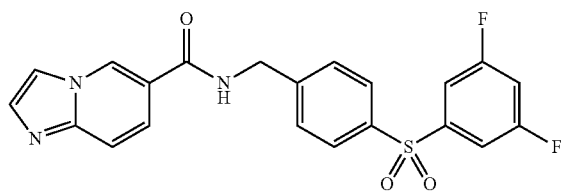 [SMILES: O=C(NCc1ccc(S(=O)(=O)c2cc(F)cc(F)c2)cc1)c1ccc2nccn2c1]

[Evaluation Example 1] NamPT Inhibitory Efficacy Evaluation

The effect of the compound prepared in the Synthesis Example 1 to 4 and the FK866 of the Comparative Example 1 on the substrate degradation rate by NAMPT enzyme (Vmax/min) was tested. First, in the step of synthesizing nicotinamide into NAD, the NamPT recombinant protein and the substrates PRPP and nicotinamide were added to the compounds of Synthesis Example 1 to 4 (A4276, A4266, A4265 and B1471) and the compound of Comparative Example 1 at various concentrations and reacted at 30° C. for 30 minutes. The OD value at 450 nm was measured at intervals of 5 minutes for 60 minutes using the conversion from WST-1 to WST-1 formazan by the produced NAD/NADH. The CycLex NAMPT colorimetric assay kit (CY-1251) was used as a measurement apparatus. The results are shown in FIG. 6 to FIG. 10. From these results, Vmax/min was calculated and the results are shown in FIG. 11 to FIG. 15.

As shown in FIG. 6 to FIG. 10, the compounds of the Synthesis Example 1 to 4 according to the present invention showed excellent NamPT inhibitory activity, and thus it is known that the compounds can be effectively used for the treatment of various diseases caused by NamPT, for example, cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosus, multiple sclerosis, psoriatic arthritis, ankylosing spondylitis, graft-versus-host disease, Alzheimer's disease, cerebrovascular accident, atherosclerosis, diabetes, glomerulonephritis and metabolic syndrome.

Furthermore, FK866 of Comparative Example 1 showed full inhibition capacity at 20 nM, indicating irreversible inhibition. On the other hand, it was confirmed that NamPT was not inhibited at the concentration of 4 nM diluted 5 times. Namely, it was found that FK866 had an irreversible inhibitory effect on the target enzyme in a narrow concentration range. In contrast, the compounds of the Synthesis Example 1 to 4 according to the present invention all exhibit increased or decreased inhibition capacity within a wide concentration range, and particularly, compounds of Synthesis Example 1 increase or decrease their inhibition capacity within a concentration of 75 times (FIG. 6), and all the compounds have higher slope at the maximum concentration than that of the FK866, indicating that the reversible inhibition was higher.

As shown in FIG. 11 to FIG. 15, it was found that the kinetic properties of the NamPT inhibition of the compounds of the Synthesis Example 1 to 4 according to the present invention contribute to increasing selectivity according to NAPRT expression by inducing a gradual decrease of NAD. It was known that this would be a favorable characteristic in the precise control of the drug dose for the safety margin in clinical practice.

[Evaluation Example 2] Therapeutic Effect of Cancer Cell Line

Various cancer cell lines including H322, H661, H1155, H1993, H1975, H2030, H1299, H2122 and HBEC30 were treated with various concentrations of the compounds of Synthesis Example 1 to 4 at various concentrations to determine the viability of the cell line according to the concentration and the results are shown in FIG. 16 to FIG. 19.

As shown in FIG. 16 to FIG. 19, all the compounds of the Synthesis Examples 1 to 4 have excellent therapeutic effects on various cancer cell lines. In the Synthesis Examples 1 to 4, the difference in LD50 values between the NAPRT positive cell line and the negative cell line was found to be at least 50 to at most 10,000 times. This indicates that the therapeutic window between NAPRT positive cells and negative cancer cells, including normal cells, is at least 5 to at most 1,000 times wider with compared to the FK866 of approximately 10 times difference.

[Evaluation Example 3] Therapeutic Effect of Cancer Cell Line

The H322, H661, H1155, H1299, H1975, H2030, H2122 and HBEC30 cell lines were treated with the compounds of the Synthesis Examples 1 to 46 at various concentrations for and $IC_{50}$ was measured and the results are shown in Table 7 below.

TABLE 7

| | $IC_{50}$ (μM) | | | | | | | | |
|---|---|---|---|---|---|---|---|---|---|
| | H322 | H661 | H1115 | H1299 | H1975 | H1993 | H2030 | H2122 | HBEC30 |
| | | | | NAPRT expression | | | | | |
| | negative | negative | negative | positive | positive | positive | positive | positive | positive |
| B1380 | 6.25 | 2.5 | | | | >12.5 | | >12.5 | >12.5 |
| B1386 | 1.56 | 7 | | | | >12.5 | | 12.5 | >12.5 |
| B1387 | 6.25 | 7 | | | | >12.5 | | 3.25 | >12.5 |
| B1416 | <1.56 | | | | | | | | |
| B1423 | 0.6 | >1 | 1 | >100 | >100 | >100 | >100 | >100 | >100 |
| B1467 | 3.125 | | | | | | | | |

TABLE 7-continued

| | IC$_{50}$(μM) | | | | | | | | |
|---|---|---|---|---|---|---|---|---|---|
| | H322 | H661 | H1115 | H1299 | H1975 | H1993 | H2030 | H2122 | HBEC30 |
| | | | | NAPRT expression | | | | | |
| | negative | negative | negative | positive | positive | positive | positive | positive | positive |
| B1468 | <0.024 | >1 | 3.16 | >100 | >100 | >100 | >100 | >100 | >100 |
| B1469 | 0.06 | | | | | | | | |
| B1470 | 0.06 | | | | | | | | |
| B1471 | <0.024 | 0.7 | >1 | 100 | >100 | >100 | >100 | >100 | >100 |
| B1472 | 0.3 | | | | | | | | |
| B1474 | 0.05 | | | | | | | | |
| B1477 | <0.024 | >1 | >1 | <100 | >100 | <100 | <100 | 31.6 | >100 |
| B1479 | 5 | | | | | | | | |
| B1484 | 0.05 | | | | | | | | |
| B1485 | 0.03 | | | | | | | | |
| B1523 | 1.56 | | | | | | | | |
| B1531 | 6.25 | | | | | | | | |
| B1716 | 12.5 | | | | | | | | |
| B1856 | 12.5 | | | | | | | | |
| B1857 | 10 | | | | | | | | |
| B1863 | 12.5 | | | | | | | | |
| B1866 | 10 | | | | | | | | |
| B1872 | 10 | | | | | | | | |
| B1873 | 5 | | | | | | | | |
| B1963 | 0.39 | | | | | | | | |
| B1964 | 0.2 | | | | | | | | |
| B1967 | 12.5 | | | | | | | | |
| B1975 | 1.2 | | | | | | | | |
| B1976 | 10 | | | | | | | | |
| B1977 | 6.25 | | | | | | | | |
| B1978 | 1.2 | | | | | | | | |
| B1979 | 0.78 | | | | | | | | |
| B1981 | 3.1 | | | | | | | | |
| B1982 | 12 | | | | | | | | |
| B1983 | 0.3 | | | | | | | | |
| Drug3 | 1 | <1 | <3.1 | | | | | | |
| A4276 | <0.03 | <0.3 | <0.03 | | | | | | |
| A4261 | 0.03 | <0.3 | <0.1 | | | | | | |
| A4262 | 0.03 | 30 | <0.1 | | | | | | |
| A4263 | <0.03 | 1 | <0.3 | | | | | | |
| A4265 | 0.003 | <0.03 | 0.01 | | | | | | |
| A4266 | 0.03 | 0.1 | 0.03 | | | | | | |
| A4275 | 0.03 | <0.3 | <0.3 | | | | | | |
| A4302 | 0.1 | 0.1 | <0.3 | | | | | | |
| A4303 | 10 | 10 | 10 | | | | | | |

As shown in Table 7, the compounds of Synthesis Examples 1 to 46 showed excellent therapeutic effect on all cancer cell lines, and particularly, the therapeutic effect was more excellent in cancer cells in which NAPRT expression was negative.

[Evaluation Example 4] Toxic Mechanism in Cancer Cell Lines

Figure 20:
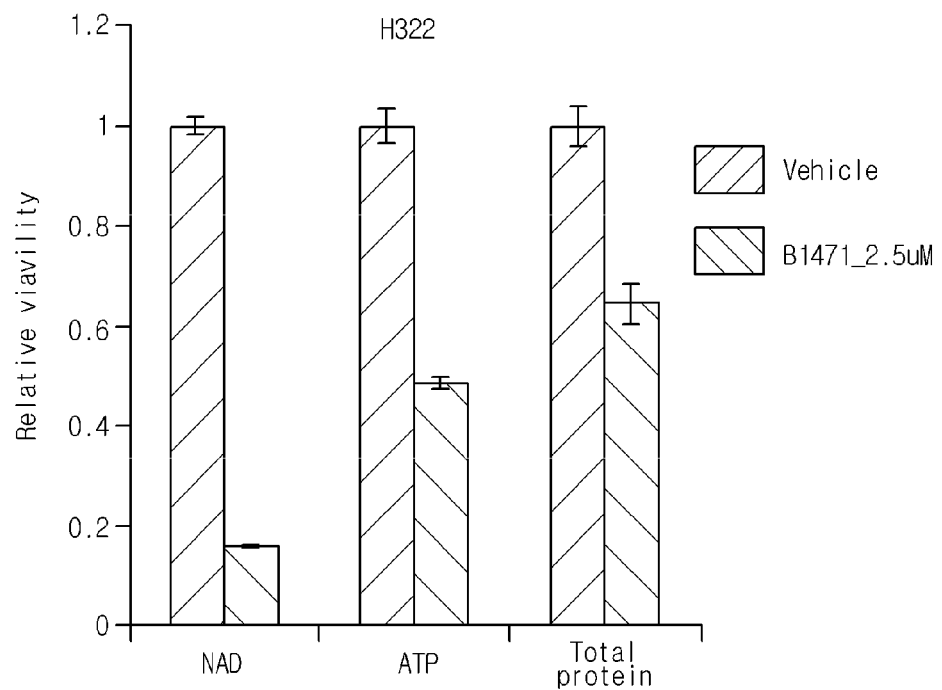
FIG. 20 is a graph showing changes in the content of intracellular NAD, ATP and total protein after treatment with 2.5 μM of the compound (B1471) prepared in Synthesis Example 4 according to an example of the present invention for the cancer cell line H322 in Evaluation Example 4.

To investigate the direct effect of the compound according to the present invention on the catalytic activity of NamPT enzyme, after treating H322 cell line with 2.5 μM of the compound of the Synthesis Example 4, the intracellular NAD, ATP and total protein was measured, with the results depicted in FIG. 20.

As shown in FIG. 20, the compound of Synthesis Example 4 of the present invention showed a decrease in the total amount of protein compared to the negative control, and in particular, the amount of ATP which is a NAD and NAD metabolite, was remarkably decreased.

As a result, the compound according to the present invention inhibited NamPT and the biosynthesis product thereof, NAD was decreased.

[Evaluation Example 5] Toxicity Assessment in Normal Cell Line

Figure 21:
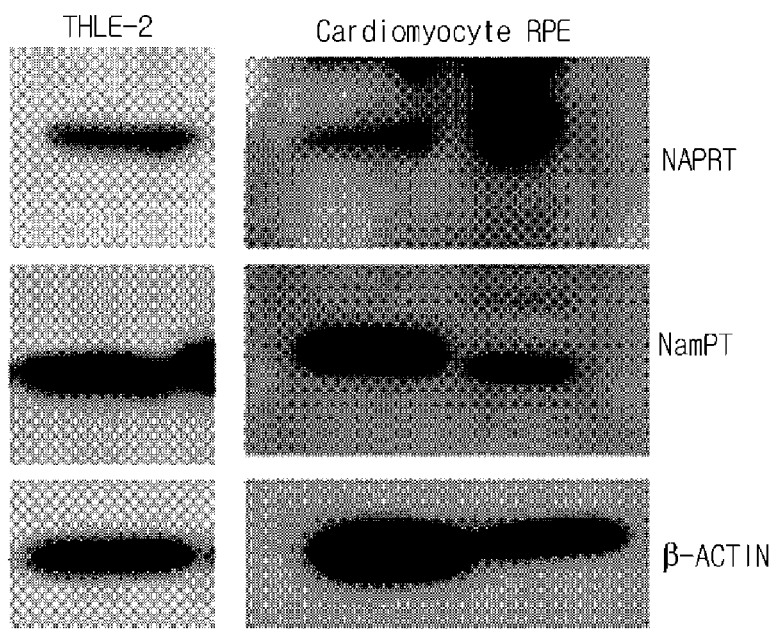
FIG. 21 shows the result analyzing expression level of NAPRT and NamPT by Western blot analysis using the cell lysate obtained after culturing primary cardiomyocyte, retinal pigment epithelium cell (RPE) and liver cell which are the normal cell line in Evaluation Example 5.

Primary cardiomyocyte (PromoCell # C-12810, Cardiomyocyte), retinal pigment epithelium cell (Lonza #194987, RPE) which are the normal cell line and liver cell (THLE-2) were cultured and the expression levels of NAPRT and NamPT were measured by Western blot using cell lysate and the results are shown in FIG. 21. In addition, the myocardial cells, retinal pigment epithelial cells and liver cells were treated with the compounds of Synthesis Examples 1 and 2 and Comparative Example 1, and the cell viability was evaluated. The results are shown in FIG. 22 to FIG. 24.

As shown in FIG. 21, normal cell lines normally express NAPRT and NamPT protein, and thus it was predicted that they would be resistant to NamPT inhibition.

Figure 22:
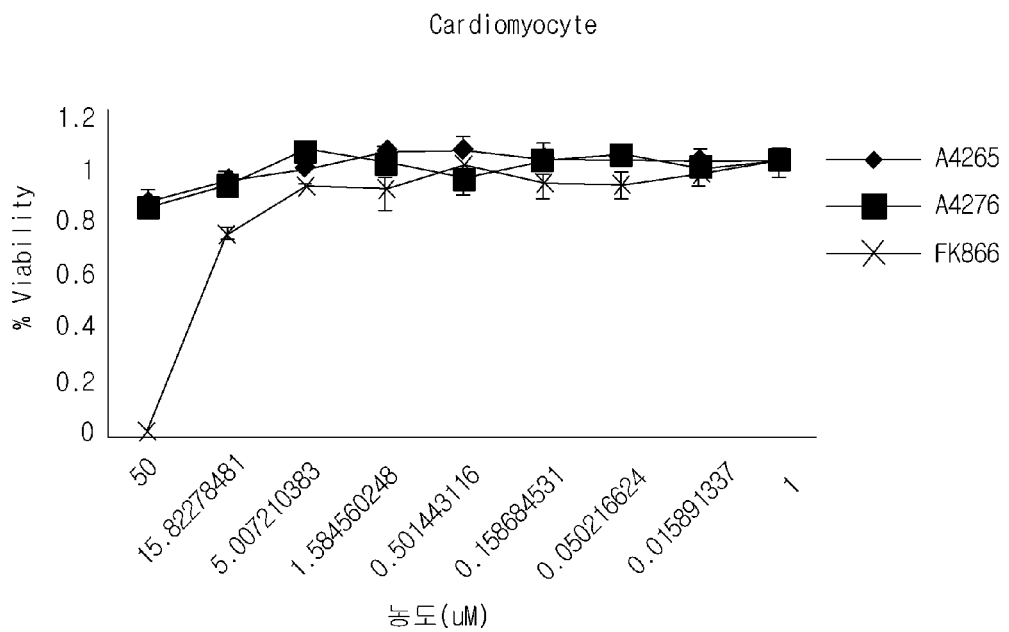
FIG. 22 shows the result measuring the change of the cell viability according to the concentration of the compounds (A4276, A4265) prepared in Synthesis Example 1 and 3, respectively and the compound (FK866) of Comparative Example 1 according to an example of the present invention for primary cardiomyocyte in Evaluation Example 5.
Figure 23:
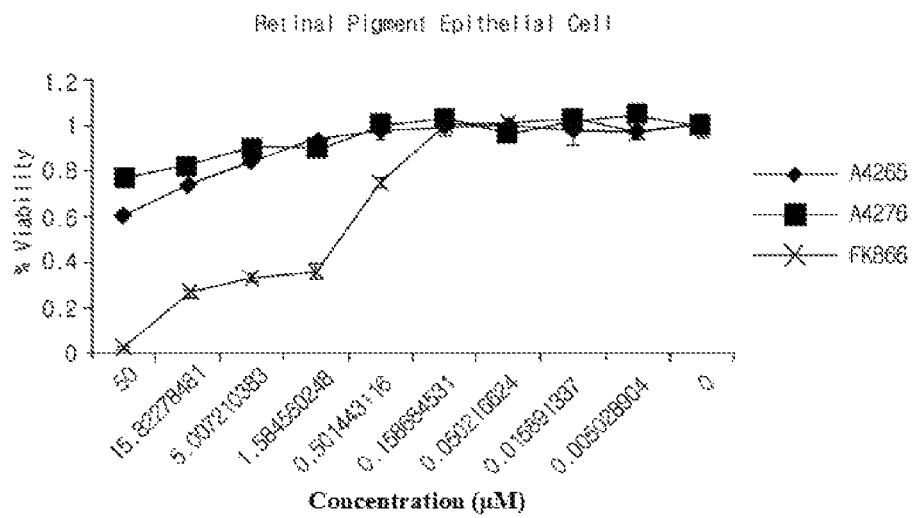
FIG. 23 shows the result measuring the change of the cell viability according to the concentration of the compounds (A4276, A4265) prepared in Synthesis Example 1 and 3, respectively and the compound (FK866) of Comparative Example 1 according to an example of the present invention for retinal pigment epithelium cell (RPE) in Evaluation Example 5.
Figure 24:
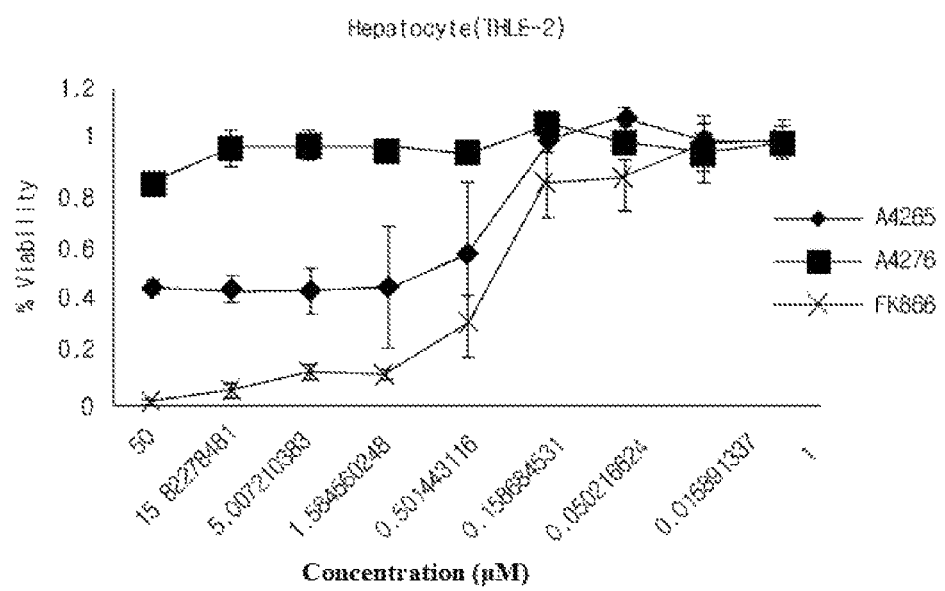
FIG. 24 shows the result measuring the change of the cell viability according to the concentration of the compounds (A4276, A4265) prepared in Synthesis Example 1 and 3, respectively and the compound (FK866) of Comparative Example 1 according to an example of the present invention for liver cell (THLE-2) in Evaluation Example 5.

As shown in FIG. 22 to FIG. 24, FK866 exhibited unpredictable cytotoxicity in THLE-2, Cardiomyocyte and RPE cells when treated at high concentrations, but the compounds of Synthesis Examples 1 and 2 of the present invention is confirmed not to cause cytotoxicity.

As a result, the compound of the present invention shows a specific killing effect only on cancer cells and does not show toxicity to normal cells.

[Evaluation Example 6] Toxicity Evaluation in Normal Cell Line

The normal liver cell lines THLE-2 and THLE-3 each were treated with the compounds of Synthesis Examples 4, 8 and 13 and Comparative Examples 1 and 2, and the cell viability was evaluated. The results are shown in FIG. 25 and FIG. 26.

Figure 25:
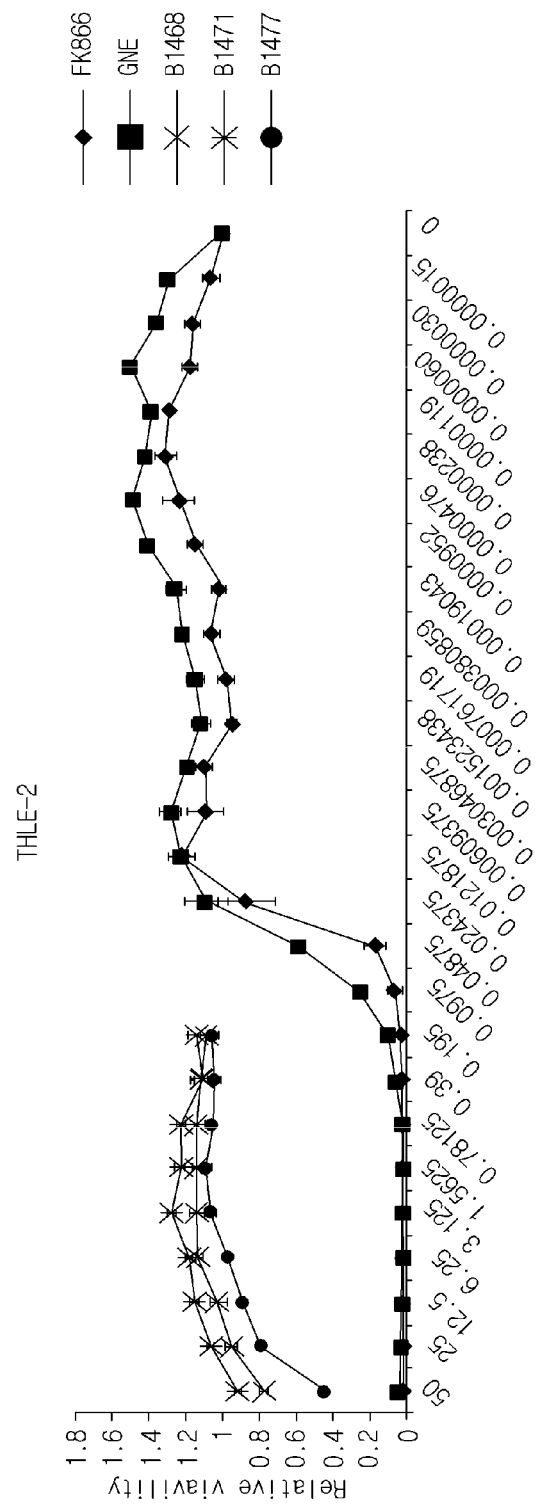
FIG. 25 shows the result measuring the change of the cell viability according to the concentration of the compounds (B1471, B1468, B1477) prepared in Synthesis Example 4, 8 and 13, respectively and the compound (FK866, GNE617) of Comparative Example 1 and 2 according to an example of the present invention for liver cell (THLE-2) in Evaluation Example 6.
Figure 26:
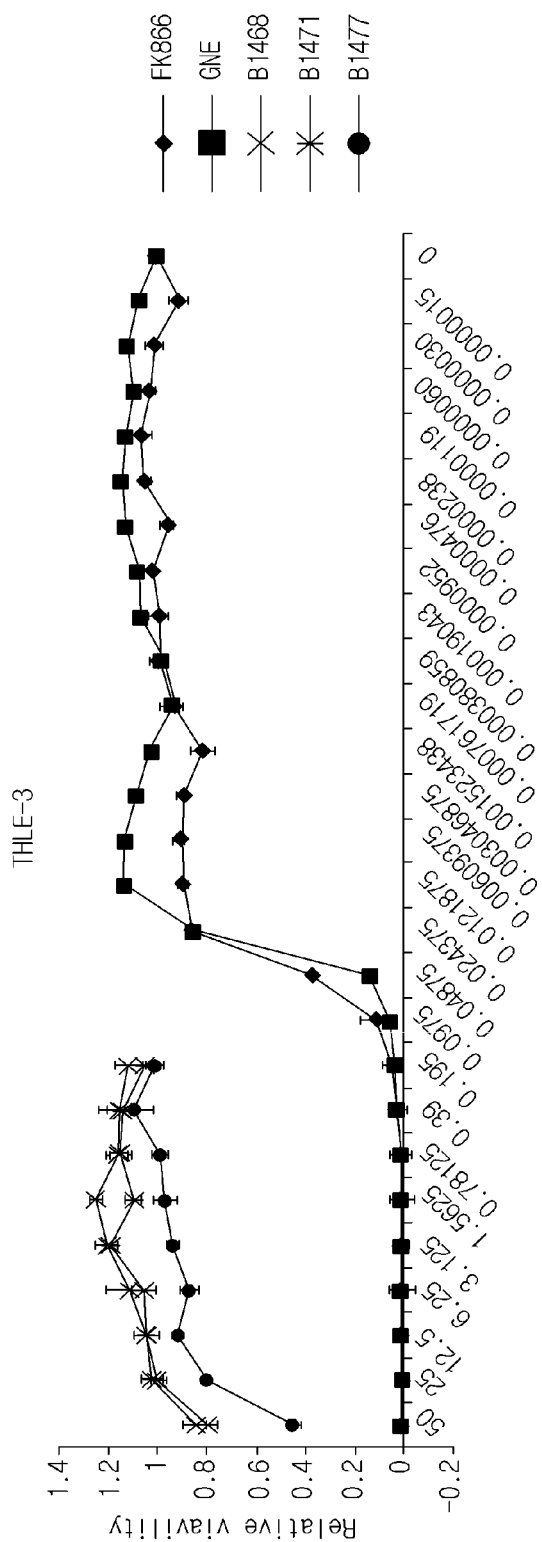
FIG. 26 shows the result measuring the change of the cell viability according to the concentration of the compounds (B1471, B1468, B1477) prepared in Synthesis Example 4, 8 and 13, respectively and the compound (FK866, GNE617) of Comparative Example 1 and 2 according to an example of the present invention for liver cell (THLE-3) in Evaluation Example 6.

As shown in FIG. 25 and FIG. 26, FK866 and GNE617 were toxic with an $IC_{50}$ value of about 0.05 μM, while the compounds of Synthesis Examples 4, 8 and 13 according to the present invention showed little toxicity even at very high concentrations of 50 μM.

As a result, it was found that the compound of the present invention showed a specific killing effect only on cancer cells and did not show toxicity to normal cells.

[Evaluation Example 7] Microsome Stability Evaluation

Metabolic stability was assessed using human liver microsomes and mouse liver microsomes. Specifically, pooled male mouse liver microsomes (in-house preparation per SOP), pooled human liver microsomes (XENOTECH; Batch No-H0630-1110189) were used. 100 μl reaction was performed with 1 μM of the compound prepared in the Synthesis Example 1 to 3 (A4276, A4266 or A4265) or the compound of Comparative Example 1 (FK866), 0.3 mg/ml microsomal protein and cofactor in the buffer (1 mM NADPH) and in addition, the mixture was incubated at different time points (0, 15, 30, 45, 60, and 90 minutes). The reaction was stopped by addition of acetonitrile (Telmesartin) containing the same volume of internal standard. The precipitated proteins were removed by centrifugation and the supernatant was analyzed by LC/MS-MS method. The percentage of the parent compound remaining after 30 minutes of reaction was quantified by the analysis using the equation, and the results are shown in Table 8 below.

Residual % parent compound=(peak area at time x/peak area at $TO$)×100.

The intrinsic clearance was calculated by the following equation.

TABLE 8

| Compound | Human(%) | Mouse(%) |
|---|---|---|
| A4265 | 81.11 ± 4.76 | 78.24 ± 6.49 |
| A4276 | 71.99 ± 3.86 | 60.69 ± 1.04 |
| A4266 | >99 | 89.3 ± 3.12 |
| FK866 | 25.48 ± 1.45 | 10.26 ± 0.91 |
| positive control (Buspirone) | 0.101 ± 0.028 | 3.189 ± 1.078 |

As shown in Table 8, when the compounds of the Synthesis Example 1 to 3 according to the present invention were treated, it was confirmed that the stability in human and mouse liver microsomes was remarkably superior to that of FK866 of Comparative Example 1.

[Evaluation Example 8] Evaluation of Cardiac Toxicity (hERG)

The hERG screening was performed by measuring the fluorescence polarization of the compound of Synthesis Example 1 to 3 and E4031 compound as a positive control using the high affinity red fluorescent hERG channel ligand tracer of the Korea Research Institute of Chemical Technology. The results are shown in Table 9 below. However, in this test method, when the inhibition rate by the 10 μM compound was at least 50, it was judged to be a substance which needs attention to hERG channel binding.

In addition, as the hERG K+ channel activity evaluation, the potential risk of log QT prolongation according to the dose used was evaluated by measuring the current inhibition according to the drug using a patch clamp technique and evaluating the $IC_{50}$. The results are shown in Table 10 below. However, $IC_{50}$ values for the hERG K+ channel by the patch fixation test method were not measured within the maximum concentration of 100 μM. In this test method, when the $IC_{50}$ value for hERG K+ channel was at least 10 μM, it was judged to be safe against cardiac toxicity.

TABLE 9

| Treatment | | Concentration (μM) | % inhibition capacity |
|---|---|---|---|
| positive control | E4031 | 10 | 87.7 ± 5.41 |
| compound | A4265 | 10 | 7.44 ± 3.12 |
| | A4266 | 10 | <1 |
| | A4276 | 10 | 12.0 ± 5.04 |

(However, % inhibition capacity in the Table 9 is expressed as mean±standard deviation.)

TABLE 10

| Compound | Concentration (μM) | $IC_{50}$(μM) |
|---|---|---|
| A4265 | 0.001, 0.01, 0.1, 1, 10, 100 | Predicted above 100 μM |
| A4266 | 0.001, 0.01, 0.1, 1, 10, 100 | Predicted above 100 μM |
| A4276 | 0.001, 0.01, 0.1, 1, 10, 100 | Predicted above 100 μM |

As shown in Table 9, it was confirmed that all the compounds of the Synthesis Example 1 to 3 according to the present invention were safe against inhibition of hERG channel activity due to protein binding.

In addition, as shown in Table 10, all the compounds of the Synthesis Example 1 to 3 according to the present invention had an $IC_{50}$ value of at least 100 μM and thus were safe for cardiac toxicity.

INDUSTRIAL APPLICABILITY

The compound of the present invention can be used as a nicotinamide phosphoribosyltransferase (NamPT) inhibitor, and further, a therapeutic agent for NamPT disease or cancer.

The invention claimed is:

1. A compound selected from a compound represented by following Chemical Formula 5, a pharmaceutically acceptable salt, an optical isomer, a hydrate and a solvate thereof:

[Chemical Formula 5]

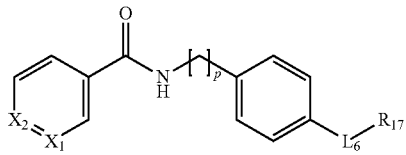

wherein in Chemical Formula 5,
$X_1$ is N;
$X_2$ is C(H);
p is an integer of 1 to 3;
$L_6$ is a direct bond; and
$R_{17}$ is represented by Chemical Formulae 3, a1 or a4:

[Chemcial Formula 3]

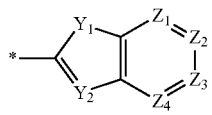

in Chemical Formula 3,
$Y_1$ is O;
$Y_2$ is N;
$Z_1$, $Z_2$ and $Z_4$ are C(H);
$R_{21}$ is hydrogen or $C_1$~$C_6$ alkyl group;
$Z_3$ is C($C_1$~$C_6$ alkyl;

[Chemical Formula a1]

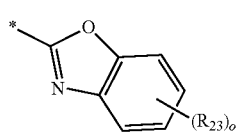

wherein in Chemical Formula a1,
* is a bonding site;
o is an integer of 0 to 2;
$R_{23}$ can be selected from the group consisting of halogen, nitro group, $C_6$~$C_{14}$ alkyl group, in case that the $R_{23}$ is plural, they can be the same as or different from each other;

[Chemical Formula a4]

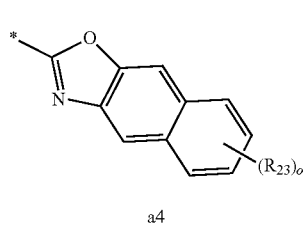

wherein in Chemical Formula a4,
* is a bonding site;
O is an integer of 0 or 2;
$R_{23}$ is selected from the group consisting of a halogen, a nitro group and $C_6$~$C_{14}$ aryl group, in case that the $R_{23}$ is plural, they can be the same as or different from each other.

2. The compound of claim 1, wherein the compound is selected from the group of following compounds:
4) N-(4-(5-methylbenzo[d]oxazol-2-yl)benzyl)nicotinamide;
5) N-(4-(5-ethylbenzo[d]oxazol-2-yl)benzyl)nicotinamide;
7) N-(4-(5-isopropylbenzo[d]oxazol-2-yl)benzyl)nicotinamide;
10) N-(4-(6-chlorobenzo[d]oxazol-2-yl)benzyl)nicotinamide;
11) N-(4-(6-nitrobenzo[d]oxazol-2-yl)benzyl)nicotinamide;
12) N-(4-(5-phenylbenzo[d]oxazol-2-yl)benzyl)nicotinamide;
13) N-(4-(naphtho[2,3-d]oxazol-2-yl)benzyl)nicotinamide.

3. A pharmaceutical composition for preventing or treating NamPT-related diseases, comprising the compound of claim 1 as an active ingredient.

4. The pharmaceutical composition of claim 3, wherein the NamPT-related diseases are selected from the group consisting of cancer, viral infection, human immunodeficiency virus, hepatitis virus, herpes virus, herpes simplex, inflammatory disorder, irritable bowel syndrome, inflammatory bowel disease, rheumatoid arthritis, asthma, chronic obstructive pulmonary disease, osteoarthritis, osteoporosis, dermatitis, atopic dermatitis, psoriasis, systemic lupus erythematosus, multiple sclerosis, psoriatic arthritis, ankylosing spondylitis, graft versus host disease, Alzheimer's disease, cerebrovascular accident, atherosclerosis, diabetes, glomerulonephritis and metabolic syndrome.

* * * * *